(12) United States Patent
Choi et al.

(10) Patent No.: US 7,622,442 B2
(45) Date of Patent: Nov. 24, 2009

(54) PROTEIN BELONGING TO THE TNF SUPERFAMILY INVOLVED IN SIGNAL TRANSDUCTION AND METHODS OF USE THEREOF

(75) Inventors: Yongwon Choi, New York, NY (US); Brian Wong, New York, NY (US); Regis Josien, New York, NY (US); Ralph Steinman, Westport, CT (US)

(73) Assignee: The Rockefeller University, New York, NY (US)

( * ) Notice: Subject to any disclaimer, the term of this patent is extended or adjusted under 35 U.S.C. 154(b) by 420 days.

(21) Appl. No.: 11/241,106

(22) Filed: Sep. 30, 2005

(65) Prior Publication Data

US 2006/0159654 A1 Jul. 20, 2006

Related U.S. Application Data

(60) Division of application No. 09/873,829, filed on May 9, 2002, now Pat. No. 7,063,960, which is a continuation-in-part of application No. 09/210,115, filed on Dec. 11, 1998, now abandoned, which is a continuation-in-part of application No. 09/034,099, filed on Mar. 3, 1998, now abandoned, which is a continuation-in-part of application No. 08/989,479, filed on Dec. 12, 1997, now abandoned.

(60) Provisional application No. 60/069,589, filed on Dec. 12, 1997.

(51) Int. Cl.
*A61K 38/17* (2006.01)
*A61K 38/19* (2006.01)
*C07K 14/00* (2006.01)
*C07K 14/52* (2006.01)

(52) U.S. Cl. .................. 514/12; 435/325; 530/351; 424/85.1

(58) Field of Classification Search .................. None
See application file for complete search history.

(56) References Cited

U.S. PATENT DOCUMENTS 5,843,678 A 12/1998 Boyle
6,242,213 B1 6/2001 Anderson

FOREIGN PATENT DOCUMENTS

WO WO 98/28424 7/1998

OTHER PUBLICATIONS

Locksley et al. The TNF and TNF receptor superfamilies: integrating mammalian biology. Cell. Feb. 23, 2001;104(4):487-501.*
Yan et al. Two-amino acid molecular switch in an epithelial morphogen that regulates binding to two distinct receptors. Science 290: 523-527, 2000.*
Szlosarek et al. Tumour necrosis factor alpha: a potential target for the therapy of solid tumours. Lancet Oncol. Sep. 2003;4(9):565-73.*
Roodman et al. RANK ligand as a therapeutic target for bone metastases and multiple myeloma. Cancer Treat Rev. Feb. 2008;34(1):92-101. Epub Oct 26, 2007.*
Amakawa et al., 1996, Cell 84:551-562.
Anderson et al., 1997, Nature 390:175-179.
Baldwin, 1996, Annu. Rev. Immunol. 14:649-683.
Barinaga, 1995, Science 274:724.
Berke, 1995, Cell 81:9-12.
Bjorck et al., 1997, Int. Immunol. 9:365-372.
Caux et al., 1994, J. Exp. Med. 180:1263-1272.
Caux et al., 1996, J. Exp. Med. 184:695-706.
Chinnaiyan et al., 1996, J. Biol. Chem. 271:4573-4576.
Chinnaiyan et al., 1997, Science 275:1122-5126.
Clark et al., 1994, Nature 367:425.
Eck et al., 1989, J. Biol. Chem. 264:17595-17605.
Flores-Romo et al., 1997, J. Exp. Med. 185:341-349.
Goillot et al., 1997, Proc. Ntl. Acad. Sci. 94:3302-3307.
Granelli-Piperno et al., 1995:, Proc. Natl. Acad. Sci. U:S.A. 92:10944-10948.
Hodge et al., 1996, Immunity, in press.
Kehrl et al., 1987, Science 238:1144.
Lacey et al., 1998, Cell 93:165-176.
Lee et al., 1997, Immunity, in press.
Liu et al., 1996, Cell 87:565-576.
Ludewig et al., 1995, Eur. J. Immunol. 25:1943-1950.
Minn et al., 1997, Nature 385:353-357.
Nacy et al., 1991, Curr. Opin. Immunol. 3:330-335.
Natoli et al., 1997, Science 275:200-203.
Park et al., 1996, Immunity 4:583-591.
Pitti et al., 1996, J. Biol. Chem. 271:12687-12690.
Rao, 1995, J. Leuko. Biol. 57:536-542.
Rothe et al., 1995, Science 269:1424-1427.
Service, 1996, Science 274:723-4.
Smith et al., 1990, Science 248:1019-1023.
Smith et al., 1994, Cell 76:959-962.
Steinman et al., 1990, Immunol. Rev. 156:25-37.

*Primary Examiner*—Daniel E. Kolker
*Assistant Examiner*—Gregory S Emch
(74) *Attorney, Agent, or Firm*—Drinker Biddle & Reath LLP

(57) ABSTRACT

A method of modulating immune response in an animal is disclosed. Such a method interacting the immature dendritic cells from the animal with an antigen ex vivo so that the immature dendritic cells present the antigen on their surfaces, inducing maturation of the immature dendritic cells ex vivo, and contacting the mature dendritic cells ex vivo with a modulator comprising TRANCE, conservative variants thereof, fragments thereof, analogs or derivatives thereof, or a fusion protein comprising the amino acid sequence of TRANCE, conservative variants thereof, or fragments thereof. After contacting the modulator ex vivo, the mature dendritic cells are introduced into the animal. As a result, immune response in the animal towards the antigen is modulated relative to the immune response against the antigen in an animal in which dendritic cells did not interact with the antigen ex vivo, and did not contact a modulator ex vivo. Preferably, the method of the present invention results in increasing immune response towards the antigen in the animal.

15 Claims, 26 Drawing Sheets

OTHER PUBLICATIONS

Steinman et al., 1991, Annu. Rev. Immunol. 9:271-296.
van Kooten et al., 1997, Curr. Opin. Immunol. 9:330-337.
Verheij et al., Nature 380:75-79.
Wang et al., 1995, J. Immunol. 155:3722-3725.
Wong et al., 1997, Semin. Immunol. 9:7-16.
Wong et al., 1997, J. Exp. Med. 186:2075-2080.
Wong et al., 1997, J. Biol. Chem. 272:25190-25194.
Wong et al., 1998, J. Biol. Chem. 273:28355-28359.
Wyllie, 1992, Cancer Metastasis Rev. 11:95-103.
Xia et al., 1995, Science 270:1326-1331.
Yang et al., 1997, Cell 89:1067-1076.
Yasuda et al., 1998, Proc. Natl. Acad. Sci. 95:3597-3602.
Young et al., 1995, J. Exp. Med. 182:1111-1119.
Young et al., 1996, J. Exp. Med. 183:7-11.
Zhen et al., 1995, Nature 337:348-351.

* cited by examiner

```
CAG ATG GAT CCT AAT AGA ATA TCA GAA GAT GGC ACT CAC TGC ATT TAT        48
Gln Met Asp Pro Asn Arg Ile Ser Glu Asp Gly Thr His Cys Ile Tyr
 1           5                  10                  15

AGA ATT TTG AGA CTC CAT GAA AAT GCA GAT TTT CAA GAC ACA ACT CTG        96
Arg Ile Leu Arg Leu His Glu Asn Ala Asp Phe Gln Asp Thr Thr Leu
             20                  25                  30

GAG AGT CAA GAT ACA AAA TTA ATA CCT GAT TCA TGT AGG AGA ATT AAA       144
Glu Ser Gln Asp Thr Lys Leu Ile Pro Asp Ser Cys Arg Arg Ile Lys
         35                  40                  45

CAG GCC TTT CAA GGA GCT GTG CAA AAG GAA TTA CAA CAT ATC GTT GGA       192
Gln Ala Phe Gln Gly Ala Val Gln Lys Glu Leu Gln His Ile Val Gly
     50                  55                  60

TCA CAG CAC ATC AGA GCA GAG AAA GCG ATG GTG GAT GGC TCA TGG TTA       240
Ser Gln His Ile Arg Ala Glu Lys Ala Met Val Asp Gly Ser Trp Leu
 65              70                  75                  80

GAT CTG GCC AAG AGG AGC AAG CTT GAA GCT CAG CCT TTT GCT CAT CTC       288
Asp Leu Ala Lys Arg Ser Lys Leu Glu Ala Gln Pro Phe Ala His Leu
             85                  90                  95

ACT ATT AAT GCC ACC GAC ATC CCA TCT GGT TCC CAT AAA GTG AGT CTG       336
Thr Ile Asn Ala Thr Asp Ile Pro Ser Gly Ser His Lys Val Ser Leu
        100                 105                 110

TCC TCT TGG TAC CAT GAT CGG GGG TGG GGT AAG ATC TCC AAC ATG ACT       384
Ser Ser Trp Tyr His Asp Arg Gly Trp Gly Lys Ile Ser Asn Met Thr
        115                 120                 125

TTT AGC AAT GGA AAA CTA ATA GTT AAT CAG GAT GGC TTT TAT TAC CTG       432
Phe Ser Asn Gly Lys Leu Ile Val Asn Gln Asp Gly Phe Tyr Tyr Leu
        130                 135                 140

TAT GCC AAC ATT TGC TTT CGA CAT CAT GAA ACT TCA GGA GAC CTA GCT       480
Tyr Ala Asn Ile Cys Phe Arg His His Glu Thr Ser Gly Asp Leu Ala
145                 150                 155                 160

ACA GAG TAT CTT CAA CTA ATG GTG TAC GTC ACT AAA ACC AGC ATC AAA       528
Thr Glu Tyr Leu Gln Leu Met Val Tyr Val Thr Lys Thr Ser Ile Lys
                165                 170                 175

ATC CCA AGT TCT CAT ACC CTG ATG AAA GGA GGA AGC ACC AAG TAT TGG       576
Ile Pro Ser Ser His Thr Leu Met Lys Gly Gly Ser Thr Lys Tyr Trp
        180                 185                 190

TCA GGG AAT TCT GAA TTC CAT TTT TAT TCC ATA AAC GTT GGT GGA TTT       624
Ser Gly Asn Ser Glu Phe His Phe Tyr Ser Ile Asn Val Gly Gly Phe
        195                 200                 205

TTT AAG TTA CGG TCT GGA GAG GAA ATC AGC ATC GAG GTC TCC AAC CCC       672
Phe Lys Leu Arg Ser Gly Glu Glu Ile Ser Ile Glu Val Ser Asn Pro
210                 215                 220

TCC TTA CTG GAT CCG GAT CAG GAT GCA ACA TAC TTT GGG GCT TTT AAA       720
Ser Leu Leu Asp Pro Asp Gln Asp Ala Thr Tyr Phe Gly Ala Phe Lys
225                 230                 235                 240
```

Figure 1

```
GTT CGA GAT ATA GAT TGA GCCCCAGTTT TTGGAGTGTT ATGTATTTCC      768
Val Arg Asp Ile Asp
        245

TGGATGTTTG GAAACATTTT TTAAAACAAG CCAAGAAAGA TGTATATAGG TGTGTGAGAC    828

TACTAAGAGG CATGGCCCAA CGGTACACGA CTCAGTATCC ATGCTCTTGA CCTTGTAGAG    888

AACACGCGTA TTTACAGCCA GTGGGAGATG TTAGACTCAT GGTGTGTTAC ACAATGGTTT    948

TTAAATTTTG TAATGAATTC CTAGAATTAA ACCAGATTGG AGCAATTACG GGTTGACCTT   1008

ATGAGAAACT GCATGTGGGC TATGGGAGGG GTTGGTCCCT GGTCATGTGC CCCTTCGCAG   1068

CTGAAGTGGA GAGGGTGTCA TCTAGCGCAA TTGAAGGATC ATCTGAAGGG GCAAATTCTT   1128

TTGAATTGTT ACATCATGCT GGAACCTGCA AAAATACTT TTTCTAATGA GGAGAGAAAA    1188

TATATGTATT TTTATATAAT ATCTAAAGTT ATATTTCAGA TGTAATGTTT TCTTTGCAAA   1248

GTATTGTAAA TTATATTTGT GCTATAGTAT TTGATTCAAA ATATTTAAAA ATGTCTTGCT   1308

GTTGACATAT TTAATGTTTT AAATGTACAG ACATATTTAA CTGGTGCACT TTGTAAATTC   1368

CCTGGGGAAA ACTTGCAGCT AAGGAGGGGA AAAAATGTTG TTTCCTAATA TCAAATGCAG   1428

TATATTTCTT CGTTCTTTTT AAGTTAATAG ATTTTTTCAG ACTTGTCAAG CCTGTGCAAA   1488

AAAATTAAAA TGGATGCCTT GAATAATAAG CAGGATGTTG GCCACCAGGT GCCTTTCAAA   1548

TTTAGAAACT AATTGACTTT AGAAAGCTGA CATTGCCAAA AAGGATACAT AATGGGCCAC   1608

TGAAATCTGT CAAGAGTAGT TATATAATTG TTGAACAGGT GTTTTTCCAC AAGTGCCGCA   1668

AATTGTACCT TTTTTTGTTT TTTCAAAAT AGAAAAGTTA TTAGTGGTTT ATCAGCAAAA    1728

AAGTCCAATT TTAATTTAGT AAATGTTATC TTATACTGTA CAATAAAAAC ATTGCCTTTG   1788

AATGTTAATT TTTTGGTACA AAAGTCGACG GCCGC                              1823
```

Figure 1 (continued)

```
Gln Met Asp Pro Asn Arg Ile Ser Glu Asp Gly Thr His Cys Ile Tyr
 1               5                  10                  15

Arg Ile Leu Arg Leu His Glu Asn Ala Asp Phe Gln Asp Thr Thr Leu
                20                  25                  30

Glu Ser Gln Asp Thr Lys Leu Ile Pro Asp Ser Cys Arg Arg Ile Lys
            35                  40                  45

Gln Ala Phe Gln Gly Ala Val Gln Lys Glu Leu Gln His Ile Val Gly
        50                  55                  60

Ser Gln His Ile Arg Ala Glu Lys Ala Met Val Asp Gly Ser Trp Leu
65                  70                  75                  80

Asp Leu Ala Lys Arg Ser Lys Leu Glu Ala Gln Pro Phe Ala His Leu
                85                  90                  95

Thr Ile Asn Ala Thr Asp Ile Pro Ser Gly Ser His Lys Val Ser Leu
                100                 105                 110

Ser Ser Trp Tyr His Asp Arg Gly Trp Gly Lys Ile Ser Asn Met Thr
            115                 120                 125

Phe Ser Asn Gly Lys Leu Ile Val Asn Gln Asp Gly Phe Tyr Tyr Leu
    130                 135                 140

Tyr Ala Asn Ile Cys Phe Arg His His Glu Thr Ser Gly Asp Leu Ala
145                 150                 155                 160

Thr Glu Tyr Leu Gln Leu Met Val Tyr Val Thr Lys Thr Ser Ile Lys
                165                 170                 175

Ile Pro Ser Ser His Thr Leu Met Lys Gly Gly Ser Thr Lys Tyr Trp
            180                 185                 190

Ser Gly Asn Ser Glu Phe His Phe Tyr Ser Ile Asn Val Gly Gly Phe
    195                 200                 205

Phe Lys Leu Arg Ser Gly Glu Glu Ile Ser Ile Glu Val Ser Asn Pro
    210                 215                 220

Ser Leu Leu Asp Pro Asp Gln Asp Ala Thr Tyr Phe Gly Ala Phe Lys
225                 230                 235                 240

Val Arg Asp Ile Asp  *
                245
```

Figure 2

```
CCCACGTCCC GGGGAGCCAC TGCCAGGACC TTTGTGAACC GGTCGGGGCG GGGGCCGTGG      60

CGGAGTCTGC TCGGCGGTGG GTGGCCCGAG AAGGGAGAGA ACGATCGCGG AGCAGGGCGC     120

CCGAACTCCG GGCGCCGCGC C ATG CGC CGG GCC AGC CGA GAC TAC GGC AAG      171
             Met Arg Arg Ala Ser Arg Asp Tyr Gly Lys
             250                             255

TAC CTG CGC AGC TCG GAA GAG ATG GGC AGC GGC CCC GGC GTC CCA CAC      219
Tyr Leu Arg Ser Ser Glu Glu Met Gly Ser Gly Pro Gly Val Pro His
         260                 265                 270

GAA GGT CCG CTG CAC CCC GCG CCT TCT GCA CCG GCT CCG GCG CCG CCA      267
Glu Gly Pro Leu His Pro Ala Pro Ser Ala Pro Ala Pro Ala Pro Pro
         275                 280                 285

CCC GCC GCC TCC CGC TCC ATG TTC CTG GCC CTC CTG GGG CTG GGA CTG      315
Pro Ala Ala Ser Arg Ser Met Phe Leu Ala Leu Leu Gly Leu Gly Leu
         290                 295                 300

GGC CAG GTG GTC TGC AGC ATC GCT CTG TTC CTG TAC TTT CGA GCG CAG      363
Gly Gln Val Val Cys Ser Ile Ala Leu Phe Leu Tyr Phe Arg Ala Gln
305                 310                 315                 320

ATG GAT CCT AAC AGA ATA TCA GAA GAC AGC ACT CAC TGC TTT TAT AGA      411
Met Asp Pro Asn Arg Ile Ser Glu Asp Ser Thr His Cys Phe Tyr Arg
         325                 330                 335

ATC CTG AGA CTC CAT GAA AAC GCA GGT TTG CAG GAC TCG ACT CTG GAG      459
Ile Leu Arg Leu His Glu Asn Ala Gly Leu Gln Asp Ser Thr Leu Glu
         340                 345                 350

AGT GAA GAC ACA CTA CCT GAC TCC TGC AGG AGG ATG AAA CAA GCC TTT      507
Ser Glu Asp Thr Leu Pro Asp Ser Cys Arg Arg Met Lys Gln Ala Phe
         355                 360                 365

CAG GGG GCC GTG CAG AAG GAA CTG CAA CAC ATT GTG GGG CCA CAG CGC      555
Gln Gly Ala Val Gln Lys Glu Leu Gln His Ile Val Gly Pro Gln Arg
         370                 375                 380

TTC TCA GGA GCT CCA GCT ATG ATG GAA GGC TCA TGG TTG GAT GTG GCC      603
Phe Ser Gly Ala Pro Ala Met Met Glu Gly Ser Trp Leu Asp Val Ala
385                 390                 395                 400

CAG CGA GGC AAG CCT GAG GCC CAG CCA TTT GCA CAC CTC ACC ATC AAT      651
Gln Arg Gly Lys Pro Glu Ala Gln Pro Phe Ala His Leu Thr Ile Asn
         405                 410                 415

GCT GCC AGC ATC CCA TCG GGT TCC CAT AAA GTC ACT CTG TCC TCT TGG      699
Ala Ala Ser Ile Pro Ser Gly Ser His Lys Val Thr Leu Ser Ser Trp
         420                 425                 430

TAC CAC GAT CGA GGC TGG GCC AAG ATC TCT AAC ATG ACG TTA AGC AAC      747
Tyr His Asp Arg Gly Trp Ala Lys Ile Ser Asn Met Thr Leu Ser Asn
         435                 440                 445

GGA AAA CTA AGG GTT AAC CAA GAT GGC TTC TAT TAC CTG TAC GCC AAC      795
Gly Lys Leu Arg Val Asn Gln Asp Gly Phe Tyr Tyr Leu Tyr Ala Asn
         450                 455                 460

ATT TGC TTT CGG CAT CAT GAA ACA TCG GGA AGC GTA CCT ACA GAC TAT      843
Ile Cys Phe Arg His His Glu Thr Ser Gly Ser Val Pro Thr Asp Tyr
465                 470                 475                 480
```

Figure 3

```
CTT CAG CTG ATG GTG TAT GTC GTT AAA ACC AGC ATC AAA ATC CCA AGT      891
Leu Gln Leu Met Val Tyr Val Val Lys Thr Ser Ile Lys Ile Pro Ser
            485                 490                 495

TCT CAT AAC CTG ATG AAA GGA GGG AGC ACG AAA AAC TGG TCG GGC AAT      939
Ser His Asn Leu Met Lys Gly Gly Ser Thr Lys Asn Trp Ser Gly Asn
            500                 505                 510

TCT GAA TTC CAC TTT TAT TCC ATA AAT GTT GGG GGA TTT TTC AAG CTC      987
Ser Glu Phe His Phe Tyr Ser Ile Asn Val Gly Gly Phe Phe Lys Leu
        515                 520                 525

CGA GCT GGT GAA GAA ATT AGC ATT CAG GTG TCC AAC CCT TCC CTG CTG     1035
Arg Ala Gly Glu Glu Ile Ser Ile Gln Val Ser Asn Pro Ser Leu Leu
    530                 535                 540

GAT CCG GAT CAA GAT GCG ACG TAC TTT GGG GCT TTC AAA GTT CAG GAC     1083
Asp Pro Asp Gln Asp Ala Thr Tyr Phe Gly Ala Phe Lys Val Gln Asp
545                 550                 555                 560

ATA GAC TGA GACTCATTTC GTGGAACATT AGCATGGATG TCCTAGATGT             1132
Ile Asp *
```

TTGGAAACTT CTTAAAAAAT GGATGATGTC TATACATGTG TAAGACTACT AAGAGACATG    1192

GCCCACGGTG TATGAAACTC ACAGCCCTCT CTCTTGAGCC CTGTACAGGT TGTGTATATG    1252

TAAAGTCCAT AGGTGATGTT AGATTCATGG TGATTACACA ACGGTTTTAC AATTTTGTAA    1312

TGATTTCCTA GAATTGAACC AGATTGGGAG AGGTATTCCG ATGCTTATGA AAAACTTACA    1372

CGTGAGCTAT GGAAGGGGGT CACAGTCTCT GGTCTAACCC CTGGACATGT GCCACTGAGA    1432

ACCTTGAAAT TAAGAGGATG CCATGTCATT GCATAGAAAT GATAGTGTGA AGGGTTAAGT    1492

TCTTTTGAAT TGTTACATTG CGCTGGGACC TGCAAATAAG TTCTTTTTTT CTAATGAGGA    1552

GAAAAATATA TGTATTTTTA TATAATGTCT AAAGTTATAT TTCAGGTGTA ATGTTTTCTG    1612

TGCAAAGTTT TGTAAATTAT ATTTGTGCTA TAGTATTTGA TTCAAAATAT TTAAAAATGT    1672

CTCACTGTTG ACATATTTAA TGTTTTAAAT GTACAGATGT ATTTAACTGG TGCACTTTGT    1732

AATTCCCCTG AAGGTACTCG TAGCTAAGGG GGCAGAATAC TGTTTCTGGT GACCACATGT    1792

AGTTTATTTC TTTATTCTTT TTAACTTAAT AGAGTCTTCA GACTTGTCAA AACTATGCAA    1852

GCAAAATAAA TAAATAAAAA TAAAATGAAT ACCTTGAATA ATAAGTAGGA TGTTGGTCAC    1912

CAGGTGCCTT TCAAATTTAG AAGCTAATTG ACTTTAGGAG CTGACATAGC CAAAAAGGAA    1972

CATAATAGGC TACTGAAATC TGTCAGGAGT ATTTATGCAA TTATTGAACA GGTGTCTTTT    2032

TTTACAAGAG CTACAAATTG TAAATTTTGG TTTCTTTTTT TTCCCATAGA AAATGTACTA    2092

TAGTTTATCA GCCAAAAAAC AATCCACTTT TTAATTTAGT GAAAGTTATT TTATTATACT    2152

GTACAATAAA AGCATTGTCT CTGAATGTTA ATTTTTTGGT ACAAAAAATA AATTTGTACG    2212

AAAAAAAAAA AAAAAAAAAA AAAAA                                         2237

Figure 3 (continued)

```
Met Arg Arg Ala Ser Arg Asp Tyr Gly Lys Tyr Leu Arg Ser Ser Glu
 1           5                  10                 15
Glu Met Gly Ser Gly Pro Gly Val Pro His Glu Gly Pro Leu His Pro
         20              25                  30
Ala Pro Ser Ala Pro Ala Pro Ala Pro Pro Ala Ala Ser Arg Ser
         35              40                  45
Met Phe Leu Ala Leu Leu Gly Leu Gly Leu Gly Gln Val Val Cys Ser
 50              55                  60
Ile Ala Leu Phe Leu Tyr Phe Arg Ala Gln Met Asp Pro Asn Arg Ile
 65              70                  75                  80
Ser Glu Asp Ser Thr His Cys Phe Tyr Arg Ile Leu Arg Leu His Glu
             85                  90                  95
Asn Ala Gly Leu Gln Asp Ser Thr Leu Glu Ser Glu Asp Thr Leu Pro
             100                 105                 110
Asp Ser Cys Arg Arg Met Lys Gln Ala Phe Gln Gly Ala Val Gln Lys
         115                 120                 125
Glu Leu Gln His Ile Val Gly Pro Gln Arg Phe Ser Gly Ala Pro Ala
 130                 135                 140
Met Met Glu Gly Ser Trp Leu Asp Val Ala Gln Arg Gly Lys Pro Glu
 145                 150                 155                 160
Ala Gln Pro Phe Ala His Leu Thr Ile Asn Ala Ala Ser Ile Pro Ser
             165                 170                 175
Gly Ser His Lys Val Thr Leu Ser Ser Trp Tyr His Asp Arg Gly Trp
             180                 185                 190
Ala Lys Ile Ser Asn Met Thr Leu Ser Asn Gly Lys Leu Arg Val Asn
         195                 200                 205
Gln Asp Gly Phe Tyr Tyr Leu Tyr Ala Asn Ile Cys Phe Arg His His
 210                 215                 220
Glu Thr Ser Gly Ser Val Pro Thr Asp Tyr Leu Gln Leu Met Val Tyr
 225                 230                 235                 240
Val Val Lys Thr Ser Ile Lys Ile Pro Ser Ser His Asn Leu Met Lys
             245                 250                 255
Gly Gly Ser Thr Lys Asn Trp Ser Gly Asn Ser Glu Phe His Phe Tyr
             260                 265                 270
Ser Ile Asn Val Gly Gly Phe Phe Lys Leu Arg Ala Gly Glu Glu Ile
             275                 280                 285
Ser Ile Gln Val Ser Asn Pro Ser Leu Leu Asp Pro Asp Gln Asp Ala
     290                 295                 300
Thr Tyr Phe Gly Ala Phe Lys Val Gln Asp Ile Asp *
 305                 310                 315
```

```
1    MRRASRDYGKYLRSSEEMGSGPGVPHEGPLHPAPSAPAPAPPPAASRSMFLALLGLGLGQ  mTRANCE

61   VVCSIALFLYFRAQMDPNRISEDSTHCFYRILRLHENAGLQDSTLESEDT--LPDSCRRM  mTRANCE
              .........G...I.........DF..T....Q..KLI......I  hTRANCE

119  KQAFQGAVQKELQHIVGPQRFSGAPAMMEGSWLDVAQRGKPEAQPFAHLTINAASIPSGS  mTRANCE
     .................S.HIRAEK..VD.....L.K.S.L.............TD.....  hTRANCE

*
179  HKVTLSSWYHDRGWAKISNMTLSNGKLRVNQDGFYYLYANICFRHHETSGSVPTDYLQLM  mTRANCE
     ...S..........G......F.....I.................DLA.E.....  hTRANCE

*
239  VYVVKTSIKIPSSHNLMKGGSTKNWSGNSEFHFYSINVGGFFKLRAGEEISIQVSNPSLL  mTRANCE
     ...T..........T........Y.....................S......E.......  hTRANCE

299  DPDQDATYFGAFKVQDID  316                                       mTRANCE
     ...............R...                                           hTRANCE
```

B

```
                                             B
120  QAFQGAVQKELQHIVG-PQRFSGAPAMMEGSWLDVAQRGKPEAQPFAHLTINA------  mTRANCE
101  QLHH--LQKELAELREFTEQSLKVSSFEKQIANDTI-SEFKEPRSVAHLTGNH------  mFasL
87   DLYP--RIEEVT-LRTSQDTISTVP--PKQSTPLIRGRPQKVAAHITGITRRSNSAL   mTRAIL
93   HPQRSNASRNLASTSQGPVAQSSREASSWMTILSPAADSTDPGVQQLPKEPETDLNPE  mLT-Beta
60   -----------RDEKPFNGLPLISSMAQTTLRSSQNSSDKPVAHVVANHQ------     mTNF-alpha B'       C'         C              D
172  ---ASIPSGSHKVT-LSSWYHD-RGWAKISNMTLSN-T-KLRVNQDGFYYLYANICFRHH  mTRANCE
152  ---------HSRSIPL-ENEDTY--GTALIKKVKYKK-ELVIKEALYFVYSKVYFRGQ   mFasL
142  I-PISKDAKT-LKQKIESWESSRKGHSFLNHVLFRN-E-ELVIEQELYTSQTYHFFYT   mTRAIL
153  LPANHLIAWMSKKQGL-SWEAKQE-EAFLRSGAQFSPTHHLALPDGVYYLHCHVGYFGR  mLT-Beta
101  ----------VEEQLEWLSQRA-NALLANMDLKDN-QLVVPADGLYLVYSQVLFKG     mTNF-alpha E                F
225  ETSGS------VPTDYLQLMVVVTSIKIPSSHNLMKGGSTKN------WSGNSEFHFY  mTRANCE
199  SQ---------NNQPLNHKVMRNSKY--PGDLVLMEKKLYYTTGQI------WAH     mFasL
198  BAEDASKMVSKDKVRIKDLVQYIYKYTSY--IDPIVLMKSAN-NSLWS-----RDALYGLF  mTRAIL
211  TPFPAG---RSRARSITLRSALYRAGGAY-GRKSPEILLEGAETVTPVVDPIEYGSL-WYT  mLT-Beta
147  GQE--------EYVLLTHTVS-RFAISY--QEKVNLLSAVK-SPCQKDTPEFAELKPWYE  mTNF-alpha G          H          I
273  SINVGGFFKLRAEEEISIQVSNPSLLDP-DQDATYFGAFKVQDID             mTRANCE
240  SYLGAVFNLTSADHIYVNISQLSLINFEESKTFFGLYKL                    mFasL
251  SIYQCCLLKKNDRIFVSVTNEHLMDLDQEASFFGAFLIN                    mTRAIL
266  BVGFGLASLQLRSGEPVYVNISHPDMVDYRRKTPEFGAVMVG                 mLT-Beta
195  PIYLGGVFQLEKGDRLSAEVNLPKYLDFAESGQVYFGVIAL                  mTNF-alpha
```

Figure 6

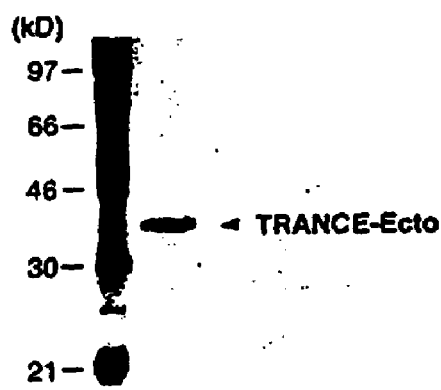
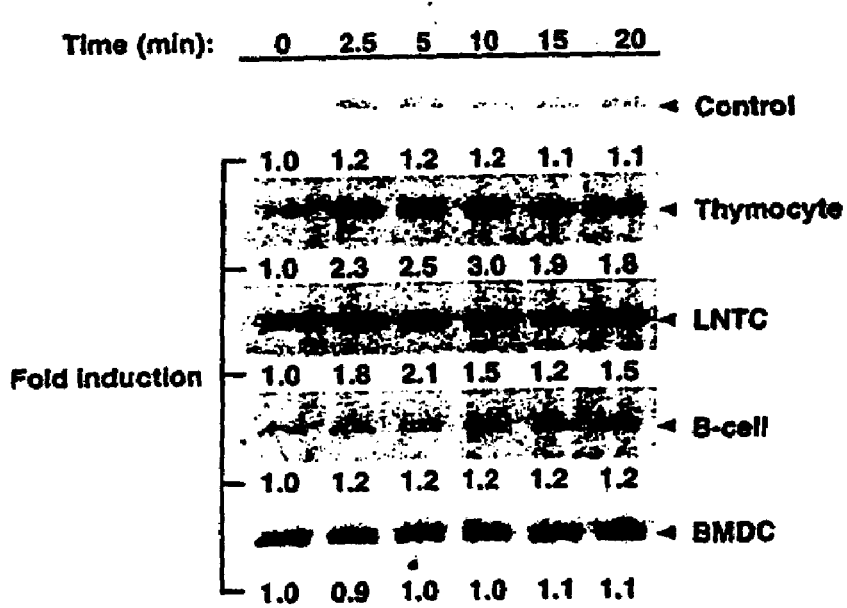
Figure 8

```
                          SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
         (A) LENGTH: 1823 base pairs
         (B) TYPE: nucleic acid
         (C) STRANDEDNESS: double
         (D) TOPOLOGY: linear (ii) MOLECULE TYPE: cDNA (iii) HYPOTHETICAL: NO (vi) ORIGINAL SOURCE:
         (A) ORGANISM: Homo sapiens (ix) FEATURE:
         (A) NAME/KEY: CDS
         (B) LOCATION: 1..738

(xi) SEQUENCE DESCRIPTION: SEQ ID NO: 1:

CAG ATG GAT CCT AAT AGA ATA TCA GAA GAT GGC ACT CAC TGC ATT TAT      48
Gln Met Asp Pro Asn Arg Ile Ser Glu Asp Gly Thr His Cys Ile Tyr
 1               5                  10                  15

AGA ATT TTG AGA CTC CAT GAA AAT GCA GAT TTT CAA GAC ACA ACT CTG      96
Arg Ile Leu Arg Leu His Glu Asn Ala Asp Phe Gln Asp Thr Thr Leu
                20                  25                  30

GAG AGT CAA GAT ACA AAA TTA ATA CCT GAT TCA TGT AGG AGA ATT AAA     144
Glu Ser Gln Asp Thr Lys Leu Ile Pro Asp Ser Cys Arg Arg Ile Lys
            35                  40                  45

CAG GCC TTT CAA GGA GCT GTG CAA AAG GAA TTA CAA CAT ATC GTT GGA     192
Gln Ala Phe Gln Gly Ala Val Gln Lys Glu Leu Gln His Ile Val Gly
        50                  55                  60

TCA CAG CAC ATC AGA GCA GAG AAA GCG ATG GTG GAT GGC TCA TGG TTA     240
Ser Gln His Ile Arg Ala Glu Lys Ala Met Val Asp Gly Ser Trp Leu
 65                 70                  75                  80

GAT CTG GCC AAG AGG AGC AAG CTT GAA GCT CAG CCT TTT GCT CAT CTC     288
Asp Leu Ala Lys Arg Ser Lys Leu Glu Ala Gln Pro Phe Ala His Leu
                85                  90                  95

ACT ATT AAT GCC ACC GAC ATC CCA TCT GGT TCC CAT AAA GTG AGT CTG     336
Thr Ile Asn Ala Thr Asp Ile Pro Ser Gly Ser His Lys Val Ser Leu
            100                 105                 110

TCC TCT TGG TAC CAT GAT CGG GGG TGG GGT AAG ATC TCC AAC ATG ACT     384
Ser Ser Trp Tyr His Asp Arg Gly Trp Gly Lys Ile Ser Asn Met Thr
        115                 120                 125

TTT AGC AAT GGA AAA CTA ATA GTT AAT CAG GAT GGC TTT TAT TAC CTG     432
Phe Ser Asn Gly Lys Leu Ile Val Asn Gln Asp Gly Phe Tyr Tyr Leu
```

```
                   130                 135                  140
TAT GCC AAC ATT TGC TTT CGA CAT CAT GAA ACT TCA GGA GAC CTA GCT       480
Tyr Ala Asn Ile Cys Phe Arg His His Glu Thr Ser Gly Asp Leu Ala
145                 150                 155                 160

ACA GAG TAT CTT CAA CTA ATG GTG TAC GTC ACT AAA ACC AGC ATC AAA       528
Thr Glu Tyr Leu Gln Leu Met Val Tyr Val Thr Lys Thr Ser Ile Lys
                    165                 170                 175

ATC CCA AGT TCT CAT ACC CTG ATG AAA GGA GGA AGC ACC AAG TAT TGG       576
Ile Pro Ser Ser His Thr Leu Met Lys Gly Gly Ser Thr Lys Tyr Trp
                180                 185                 190

TCA GGG AAT TCT GAA TTC CAT TTT TAT TCC ATA AAC GTT GGT GGA TTT       624
Ser Gly Asn Ser Glu Phe His Phe Tyr Ser Ile Asn Val Gly Gly Phe
            195                 200                 205

TTT AAG TTA CGG TCT GGA GAG GAA ATC AGC ATC GAG GTC TCC AAC CCC       672
Phe Lys Leu Arg Ser Gly Glu Glu Ile Ser Ile Glu Val Ser Asn Pro
        210                 215                 220

TCC TTA CTG GAT CCG GAT CAG GAT GCA ACA TAC TTT GGG GCT TTT AAA       720
Ser Leu Leu Asp Pro Asp Gln Asp Ala Thr Tyr Phe Gly Ala Phe Lys
225                 230                 235                 240

GTT CGA GAT ATA GAT TGA GCCCCAGTTT TTGGAGTGTT ATGTATTTCC              768
Val Arg Asp Ile Asp *
                245

TGGATGTTTG GAAACATTTT TTAAAACAAG CCAAGAAAGA TGTATATAGG TGTGTGAGAC      828

TACTAAGAGG CATGGCCCAA CGGTACACGA CTCAGTATCC ATGCTCTTGA CCTTGTAGAG      888

AACACGCGTA TTTACAGCCA GTGGGAGATG TTAGACTCAT GGTGTGTTAC ACAATGGTTT      948

TTAAATTTTG TAATGAATTC CTAGAATTAA ACCAGATTGG AGCAATTACG GGTTGACCTT     1008

ATGAGAAACT GCATGTGGGC TATGGGAGGG GTTGGTCCCT GGTCATGTGC CCCTTCGCAG     1068

CTGAAGTGGA GAGGGTGTCA TCTAGCGCAA TTGAAGGATC ATCTGAAGGG GCAAATTCTT     1128

TTGAATTGTT ACATCATGCT GGAACCTGCA AAAAATACTT TTTCTAATGA GGAGAGAAAA     1188

TATATGTATT TTTATATAAT ATCTAAAGTT ATATTTCAGA TGTAATGTTT CTTTGCAAA      1248

GTATTGTAAA TTATATTTGT GCTATAGTAT TTGATTCAAA ATATTTAAAA ATGTCTTGCT     1308

GTTGACATAT TTAATGTTTT AAATGTACAG ACATATTTAA CTGGTGCACT TGTAAATTC      1368

CCTGGGGAAA ACTTGCAGCT AAGGAGGGGA AAAAATGTTG TTTCCTAATA TCAAATGCAG     1428

TATATTTCTT CGTTCTTTTT AAGTTAATAG ATTTTTTCAG ACTTGTCAAG CCTGTGCAAA     1488

AAAATTAAAA TGGATGCCTT GAATAATAAG CAGGATGTTG GCCACCAGGT GCCTTTCAAA     1548

TTTAGAAACT AAATTGACTT TAGAAAGCTGA CATTGCCAAA AAGGATACAT AATGGGCCAC    1608

TGAAATCTGT CAAGAGTAGT TATATAATTG TTGAACAGGT GTTTTTCCAC AAGTGCCGCA     1668

AATTGTACCT TTTTTTGTTT TTTTCAAAAT AGAAAGTTA TTAGTGGTTT ATCAGCAAAA      1728

AAGTCCAATT TTAATTTAGT AAATGTTATC TTATACTGTA CAATAAAAAC ATTGCCTTTG     1788

AATGTTAATT TTTTGGTACA AAAGTCGACG GCCGC                                1823

(2) INFORMATION FOR SEQ ID NO: 2:

(i) SEQUENCE CHARACTERISTICS:
        (A) LENGTH: 245 amino acids
        (B) TYPE: amino acid
        (D) TOPOLOGY: linear (ii) MOLECULE TYPE: protein (xi) SEQUENCE DESCRIPTION: SEQ ID NO: 2:

Gln Met Asp Pro Asn Arg Ile Ser Glu Asp Gly Thr His Cys Ile Tyr
```

```
              1               5              10              15
Arg Ile Leu Arg Leu His Glu Asn Ala Asp Phe Gln Asp Thr Thr Leu
                20                  25                  30

Glu Ser Gln Asp Thr Lys Leu Ile Pro Asp Ser Cys Arg Arg Ile Lys
            35                  40                  45

Gln Ala Phe Gln Gly Ala Val Gln Lys Glu Leu Gln His Ile Val Gly
        50                  55                  60

Ser Gln His Ile Arg Ala Glu Lys Ala Met Val Asp Gly Ser Trp Leu
65                  70                  75                  80

Asp Leu Ala Lys Arg Ser Lys Leu Glu Ala Gln Pro Phe Ala His Leu
                85                  90                  95

Thr Ile Asn Ala Thr Asp Ile Pro Ser Gly Ser His Lys Val Ser Leu
                100                 105                 110

Ser Ser Trp Tyr His Asp Arg Gly Trp Gly Lys Ile Ser Asn Met Thr
            115                 120                 125

Phe Ser Asn Gly Lys Leu Ile Val Asn Gln Asp Gly Phe Tyr Tyr Leu
        130                 135                 140

Tyr Ala Asn Ile Cys Phe Arg His His Glu Thr Ser Gly Asp Leu Ala
145                 150                 155                 160

Thr Glu Tyr Leu Gln Leu Met Val Tyr Val Thr Lys Thr Ser Ile Lys
                165                 170                 175

Ile Pro Ser Ser His Thr Leu Met Lys Gly Gly Ser Thr Lys Tyr Trp
                180                 185                 190

Ser Gly Asn Ser Glu Phe His Phe Tyr Ser Ile Asn Val Gly Gly Phe
            195                 200                 205

Phe Lys Leu Arg Ser Gly Glu Glu Ile Ser Ile Glu Val Ser Asn Pro
        210                 215                 220

Ser Leu Leu Asp Pro Asp Gln Asp Ala Thr Tyr Phe Gly Ala Phe Lys
225                 230                 235                 240

Val Arg Asp Ile Asp
                245

(2) INFORMATION FOR SEQ ID NO: 3:

(i) SEQUENCE CHARACTERISTICS:
        (A) LENGTH: 2237 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: Mus musculus (ix) FEATURE:
        (A) NAME/KEY: CDS
        (B) LOCATION: 142..1092

(xi) SEQUENCE DESCRIPTION: SEQ ID NO: 3:

CCCACGTCCC GGGGAGCCAC TGCCAGGACC TTTGTGAACC GGTCGGGGCG GGGGCCGTGG     60

CGGAGTCTGC TCGGCGGTGG GTGGCCCGAG AAGGGAGAGA ACGATCGCGG AGCAGGGCGC    120

CCGAACTCCG GGCGCCGCGC C ATG CGC CGG GCC AGC CGA GAC TAC GGC AAG     171
               Met Arg Arg Ala Ser Arg Asp Tyr Gly Lys
                               250                 255

TAC CTG CGC AGC TCG GAA GAG ATG GGC AGC GGC CCC GGC GTC CCA CAC     219
Tyr Leu Arg Ser Ser Glu Glu Met Gly Ser Gly Pro Gly Val Pro His
```

-continued

```
                260                 265                 270
GAA GGT CCG CTG CAC CCC GCG CCT TCT GCA CCG GCT CCG GCG CCG CCA      267
Glu Gly Pro Leu His Pro Ala Pro Ser Ala Pro Ala Pro Ala Pro Pro
            275                 280                 285

CCC GCC GCC TCC CGC TCC ATG TTC CTG GCC CTC CTG GGG CTG GGA CTG      315
Pro Ala Ala Ser Arg Ser Met Phe Leu Ala Leu Leu Gly Leu Gly Leu
            290                 295                 300

GGC CAG GTG GTC TGC AGC ATC GCT CTG TTC CTG TAC TTT CGA GCG CAG      363
Gly Gln Val Val Cys Ser Ile Ala Leu Phe Leu Tyr Phe Arg Ala Gln
305                 310                 315                 320

ATG GAT CCT AAC AGA ATA TCA GAA GAC AGC ACT CAC TGC TTT TAT AGA      411
Met Asp Pro Asn Arg Ile Ser Glu Asp Ser Thr His Cys Phe Tyr Arg
                325                 330                 335

ATC CTG AGA CTC CAT GAA AAC GCA GGT TTG CAG GAC TCG ACT CTG GAG      459
Ile Leu Arg Leu His Glu Asn Ala Gly Leu Gln Asp Ser Thr Leu Glu
            340                 345                 350

AGT GAA GAC ACA CTA CCT GAC TCC TGC AGG AGG ATG AAA CAA GCC TTT      507
Ser Glu Asp Thr Leu Pro Asp Ser Cys Arg Arg Met Lys Gln Ala Phe
            355                 360                 365

CAG GGG GCC GTG CAG AAG GAA CTG CAA CAC ATT GTG GGG CCA CAG CGC      555
Gln Gly Ala Val Gln Lys Glu Leu Gln His Ile Val Gly Pro Gln Arg
            370                 375                 380

TTC TCA GGA GCT CCA GCT ATG ATG GAA GGC TCA TGG TTG GAT GTG GCC      603
Phe Ser Gly Ala Pro Ala Met Met Glu Gly Ser Trp Leu Asp Val Ala
385                 390                 395                 400

CAG CGA GGC AAG CCT GAG GCC CAG CCA TTT GCA CAC CTC ACC ATC AAT      651
Gln Arg Gly Lys Pro Glu Ala Gln Pro Phe Ala His Leu Thr Ile Asn
                405                 410                 415

GCT GCC AGC ATC CCA TCG GGT TCC CAT AAA GTC ACT CTG TCC TCT TGG      699
Ala Ala Ser Ile Pro Ser Gly Ser His Lys Val Thr Leu Ser Ser Trp
            420                 425                 430

TAC CAC GAT CGA GGC TGG GCC AAG ATC TCT AAC ATG ACG TTA AGC AAC      747
Tyr His Asp Arg Gly Trp Ala Lys Ile Ser Asn Met Thr Leu Ser Asn
            435                 440                 445

GGA AAA CTA AGG GTT AAC CAA GAT GGC TTC TAT TAC CTG TAC GCC AAC      795
Gly Lys Leu Arg Val Asn Gln Asp Gly Phe Tyr Tyr Leu Tyr Ala Asn
            450                 455                 460

ATT TGC TTT CGG CAT CAT GAA ACA TCG GGA AGC GTA CCT ACA GAC TAT      843
Ile Cys Phe Arg His His Glu Thr Ser Gly Ser Val Pro Thr Asp Tyr
465                 470                 475                 480

CTT CAG CTG ATG GTG TAT GTC GTT AAA ACC AGC ATC AAA ATC CCA AGT      891
Leu Gln Leu Met Val Tyr Val Val Lys Thr Ser Ile Lys Ile Pro Ser
            485                 490                 495

TCT CAT AAC CTG ATG AAA GGA GGG AGC ACG AAA AAC TGG TCG GGC AAT      939
Ser His Asn Leu Met Lys Gly Gly Ser Thr Lys Asn Trp Ser Gly Asn
            500                 505                 510

TCT GAA TTC CAC TTT TAT TCC ATA AAT GTT GGG GGA TTT TTC AAG CTC      987
Ser Glu Phe His Phe Tyr Ser Ile Asn Val Gly Gly Phe Phe Lys Leu
            515                 520                 525

CGA GCT GGT GAA GAA ATT AGC ATT CAG GTG TCC AAC CCT TCC CTG CTG     1035
Arg Ala Gly Glu Glu Ile Ser Ile Gln Val Ser Asn Pro Ser Leu Leu
            530                 535                 540

GAT CCG GAT CAA GAT GCG ACG TAC TTT GGG GCT TTC AAA GTT CAG GAC     1083
Asp Pro Asp Gln Asp Ala Thr Tyr Phe Gly Ala Phe Lys Val Gln Asp
545                 550                 555                 560

ATA GAC TGA GACTCATTTC GTGGAACATT AGCATGGATG TCCTAGATGT            1132
Ile Asp  *

TTGGAAACTT CTTAAAAAAT GGATGATGTC TATACATGTG TAAGACTACT AAGAGACATG  1192
```

-continued

```
GCCCACGGTG TATGAAACTC ACAGCCCTCT CTCTTGAGCC CTGTACAGGT TGTGTATATG    1252
TAAAGTCCAT AGGTGATGTT AGATTCATGG TGATTACACA ACGGTTTTAC AATTTTGTAA    1312
TGATTTCCTA GAATTGAACC AGATTGGGAG AGGTATTCCG ATGCTTATGA AAAACTTACA    1372
CGTGAGCTAT GGAAGGGGGT CACAGTCTCT GGTCTAACCC CTGGACATGT GCCACTGAGA    1432
ACCTTGAAAT TAAGAGGATG CCATGTCATT GCATAGAAAT GATAGTGTGA AGGGTTAAGT    1492
TCTTTTGAAT TGTTACATTG CGCTGGGACC TGCAAATAAG TTCTTTTTTT CTAATGAGGA    1552
GAAAAATATA TGTATTTTTA TATAATGTCT AAAGTTATAT TTCAGGTGTA ATGTTTTCTG    1612
TGCAAAGTTT TGTAAATTAT ATTTGTGCTA TAGTATTTGA TTCAAAATAT TTAAAAATGT    1672
CTCACTGTTG ACATATTTAA TGTTTTAAAT GTACAGATGT ATTTAACTGG TGCACTTTGT    1732
AATTCCCCTG AAGGTACTCG TAGCTAAGGG GGCAGAATAC TGTTTCTGGT GACCACATGT    1792
AGTTTATTTC TTTATTCTTT TTAACTTAAT AGAGTCTTCA GACTTGTCAA ACTATGCAA     1852
GCAAATAAA TAAATAAAAA TAAAATGAAT ACCTTGAATA ATAAGTAGGA TGTTGGTCAC     1912
CAGGTGCCTT TCAAATTTAG AAGCTAATTG ACTTTAGGAG CTGACATAGC CAAAAGGAA     1972
CATAATAGGC TACTGAAATC TGTCAGGAGT ATTTATGCAA TTATTGAACA GGTGTCTTTT    2032
TTTACAAGAG CTACAAATTG TAAATTTTGG TTTCTTTTTT TTCCCATAGA AATGTACTA     2092
TAGTTTATCA GCCAAAAAAC AATCCACTTT TTAATTTAGT GAAAGTTATT TTATTATACT    2152
GTACAATAAA AGCATTGTCT CTGAATGTTA ATTTTTTGGT ACAAAAAATA AATTTGTACG    2212
AAAAAAAAAA AAAAAAAAA AAAA                                           2237
```

(2) INFORMATION FOR SEQ ID NO: 4:

(i) SEQUENCE CHARACTERISTICS:
      (A) LENGTH: 316 amino acids
      (B) TYPE: amino acid
      (D) TOPOLOGY: linear (ii) MOLECULE TYPE: protein (xi) SEQUENCE DESCRIPTION: SEQ ID NO: 4:

```
Met Arg Arg Ala Ser Arg Asp Tyr Gly Lys Tyr Leu Arg Ser Ser Glu
 1               5                  10                  15

Glu Met Gly Ser Gly Pro Gly Val Pro His Glu Gly Pro Leu His Pro
             20                  25                  30

Ala Pro Ser Ala Pro Ala Pro Ala Pro Pro Ala Ala Ser Arg Ser
         35                  40                  45

Met Phe Leu Ala Leu Leu Gly Leu Gly Leu Gly Gln Val Val Cys Ser
 50                  55                  60

Ile Ala Leu Phe Leu Tyr Phe Arg Ala Gln Met Asp Pro Asn Arg Ile
 65                  70                  75                  80

Ser Glu Asp Ser Thr His Cys Phe Tyr Arg Ile Leu Arg Leu His Glu
                 85                  90                  95

Asn Ala Gly Leu Gln Asp Ser Thr Leu Glu Ser Glu Asp Thr Leu Pro
            100                 105                 110

Asp Ser Cys Arg Arg Met Lys Gln Ala Phe Gln Gly Ala Val Gln Lys
        115                 120                 125

Glu Leu Gln His Ile Val Gly Pro Gln Arg Phe Ser Gly Ala Pro Ala
    130                 135                 140

Met Met Glu Gly Ser Trp Leu Asp Val Ala Gln Arg Gly Lys Pro Glu
145                 150                 155                 160

Ala Gln Pro Phe Ala His Leu Thr Ile Asn Ala Ala Ser Ile Pro Ser
```

```
                165                 170                 175
Gly Ser His Lys Val Thr Leu Ser Ser Trp Tyr His Asp Arg Gly Trp
            180                 185                 190

Ala Lys Ile Ser Asn Met Thr Leu Ser Asn Gly Lys Leu Arg Val Asn
            195                 200                 205

Gln Asp Gly Phe Tyr Tyr Leu Tyr Ala Asn Ile Cys Phe Arg His His
            210                 215                 220

Glu Thr Ser Gly Ser Val Pro Thr Asp Tyr Leu Gln Leu Met Val Tyr
225                 230                 235                 240

Val Val Lys Thr Ser Ile Lys Ile Pro Ser Ser His Asn Leu Met Lys
            245                 250                 255

Gly Gly Ser Thr Lys Asn Trp Ser Gly Asn Ser Glu Phe His Phe Tyr
            260                 265                 270

Ser Ile Asn Val Gly Gly Phe Phe Lys Leu Arg Ala Gly Glu Glu Ile
            275                 280                 285

Ser Ile Gln Val Ser Asn Pro Ser Leu Leu Asp Pro Asp Gln Asp Ala
            290                 295                 300

Thr Tyr Phe Gly Ala Phe Lys Val Gln Asp Ile Asp
305                 310                 315

(2) INFORMATION FOR SEQ ID NO: 5:

(i) SEQUENCE CHARACTERISTICS:
        (A) LENGTH: 279 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
         (A) ORGANISM: Mus musculus (xi) SEQUENCE DESCRIPTION: SEQ ID NO: 5:

Met Gln Gln Pro Met Asn Tyr Pro Cys Pro Gln Ile Phe Trp Val Asp
1               5                   10                  15

Ser Ser Ala Thr Ser Ser Trp Ala Pro Pro Gly Ser Val Phe Pro Cys
            20                  25                  30

Pro Ser Cys Gly Pro Arg Gly Pro Asp Gln Arg Arg Pro Pro Pro Pro
            35                  40                  45

Pro Pro Pro Val Ser Pro Leu Pro Pro Ser Gln Pro Leu Pro Leu
50                  55                  60

Pro Pro Leu Thr Pro Leu Lys Lys Lys Asp His Asn Thr Asn Leu Trp
65                  70                  75                  80

Leu Pro Val Val Phe Phe Met Val Leu Val Ala Leu Val Gly Met Gly
            85                  90                  95

Leu Gly Met Tyr Gln Leu Phe His Leu Gln Lys Glu Leu Ala Glu Leu
            100                 105                 110

Arg Glu Phe Thr Asn Gln Ser Leu Lys Val Ser Ser Phe Glu Lys Gln
            115                 120                 125

Ile Ala Asn Pro Ser Thr Pro Ser Glu Lys Lys Glu Pro Arg Ser Val
            130                 135                 140

Ala His Leu Thr Gly Asn Pro His Ser Arg Ser Ile Pro Leu Glu Trp
145                 150                 155                 160

Glu Asp Thr Tyr Gly Thr Ala Leu Ile Ser Gly Val Lys Tyr Lys Lys
            165                 170                 175
```

```
Gly Gly Leu Val Ile Asn Glu Thr Gly Leu Tyr Phe Val Tyr Ser Lys
            180                 185                 190

Val Tyr Phe Arg Gly Gln Ser Cys Asn Asn Gln Pro Leu Asn His Lys
            195                 200                 205

Val Tyr Met Arg Asn Ser Lys Tyr Pro Glu Asp Leu Val Leu Met Glu
            210                 215                 220

Glu Lys Arg Leu Asn Tyr Cys Thr Thr Gly Gln Ile Trp Ala His Ser
225                 230                 235                 240

Ser Tyr Leu Gly Ala Val Phe Asn Leu Thr Ser Ala Asp His Leu Tyr
            245                 250                 255

Val Asn Ile Ser Gln Leu Ser Leu Ile Asn Phe Glu Glu Ser Lys Thr
            260                 265                 270

Phe Phe Gly Leu Tyr Lys Leu
            275

(2) INFORMATION FOR SEQ ID NO: 6:

(i) SEQUENCE CHARACTERISTICS:
        (A) LENGTH: 291 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
         (A) ORGANISM: Mus musculus (xi) SEQUENCE DESCRIPTION: SEQ ID NO: 6:

Met Pro Ser Ser Gly Ala Leu Lys Asp Leu Ser Phe Ser Gln His Phe
1                   5                   10                  15

Arg Met Met Val Ile Cys Ile Val Leu Leu Gln Val Leu Leu Gln Ala
            20                  25                  30

Val Ser Val Ala Val Thr Tyr Met Tyr Phe Thr Asn Glu Met Lys Gln
            35                  40                  45

Leu Gln Asp Asn Tyr Ser Lys Ile Gly Leu Ala Cys Phe Ser Lys Thr
50                  55                  60

Asp Glu Asp Phe Trp Asp Ser Thr Asp Gly Ile Leu Asn Arg Pro
65                  70                  75                  80

Cys Leu Gln Val Lys Arg Gln Leu Tyr Gln Leu Ile Glu Glu Val Thr
            85                  90                  95

Leu Arg Thr Phe Gln Asp Thr Ile Ser Thr Val Pro Glu Lys Gln Leu
            100                 105                 110

Ser Thr Pro Pro Leu Pro Arg Gly Gly Arg Pro Gln Lys Val Ala Ala
            115                 120                 125

His Ile Thr Gly Ile Thr Arg Arg Ser Asn Ser Ala Leu Ile Pro Ile
            130                 135                 140

Ser Lys Asp Gly Lys Thr Leu Gly Gln Lys Ile Glu Ser Trp Glu Ser
145                 150                 155                 160

Ser Arg Lys Gly His Ser Phe Leu Asn His Val Leu Phe Arg Asn Gly
            165                 170                 175

Glu Leu Val Ile Glu Gln Glu Gly Leu Tyr Tyr Ile Tyr Ser Gln Thr
            180                 185                 190

Tyr Phe Arg Phe Gln Glu Ala Glu Asp Ala Ser Lys Met Val Ser Lys
            195                 200                 205
```

```
Asp Lys Val Arg Thr Lys Gln Leu Val Gln Tyr Ile Tyr Lys Tyr Thr
    210                 215                 220
Ser Tyr Pro Asp Pro Ile Val Leu Met Lys Ser Ala Arg Asn Ser Cys
225                 230                 235                 240
Trp Ser Arg Asp Ala Glu Tyr Gly Leu Tyr Ser Ile Tyr Gln Gly Gly
                245                 250                 255
Leu Phe Glu Leu Lys Lys Asn Asp Arg Ile Phe Val Ser Val Thr Asn
                260                 265                 270
Glu His Leu Met Asp Leu Asp Gln Glu Ala Ser Phe Phe Gly Ala Phe
                275                 280                 285
Leu Ile Asn
    290

(2) INFORMATION FOR SEQ ID NO: 7:

(i) SEQUENCE CHARACTERISTICS:
        (A) LENGTH: 306 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Mus musculus (xi) SEQUENCE DESCRIPTION: SEQ ID NO: 7:

Met Gly Thr Arg Gly Leu Gln Gly Leu Gly Arg Pro Gln Gly Arg
1               5                   10                  15
Gly Cys Leu Leu Leu Ala Val Ala Gly Ala Thr Ser Leu Val Thr Leu
                20                  25                  30
Leu Leu Ala Val Pro Ile Thr Val Leu Ala Val Leu Ala Leu Val Pro
                35                  40                  45
Gln Asp Gln Gly Arg Arg Val Glu Lys Ile Ile Gly Ser Gly Ala Gln
    50                  55                  60
Ala Gln Lys Arg Leu Asp Asp Ser Lys Pro Ser Cys Ile Leu Pro Ser
65                  70                  75                  80
Pro Ser Ser Leu Ser Glu Thr Pro Asp Pro Arg Leu His Pro Gln Arg
                85                  90                  95
Ser Asn Ala Ser Arg Asn Leu Ala Ser Thr Ser Gln Gly Pro Val Ala
                100                 105                 110
Gln Ser Ser Arg Glu Ala Ser Ala Trp Met Thr Ile Leu Ser Pro Ala
            115                 120                 125
Ala Asp Ser Thr Pro Asp Pro Gly Val Gln Gln Leu Pro Lys Gly Glu
        130                 135                 140
Pro Glu Thr Asp Leu Asn Pro Glu Leu Pro Ala Ala His Leu Ile Gly
145                 150                 155                 160
Ala Trp Met Ser Gly Gln Gly Leu Ser Trp Glu Ala Ser Gln Glu Glu
                165                 170                 175
Ala Phe Leu Arg Ser Gly Ala Gln Phe Ser Pro Thr His Gly Leu Ala
                180                 185                 190
Leu Pro Gln Asp Gly Val Tyr Tyr Leu Tyr Cys His Val Gly Tyr Arg
            195                 200                 205
Gly Arg Thr Pro Pro Ala Gly Arg Ser Arg Ala Arg Ser Leu Thr Leu
    210                 215                 220
Arg Ser Ala Leu Tyr Arg Ala Gly Gly Ala Tyr Gly Arg Gly Ser Pro
```

```
225                 230                 235                 240
Glu Leu Leu Leu Glu Gly Ala Glu Thr Val Thr Pro Val Val Asp Pro
                245                 250                 255

Ile Gly Tyr Gly Ser Leu Trp Tyr Thr Ser Val Gly Phe Gly Gly Leu
            260                 265                 270

Ala Gln Leu Arg Ser Gly Glu Arg Val Tyr Val Asn Ile Ser His Pro
        275                 280                 285

Asp Met Val Asp Tyr Arg Arg Gly Lys Thr Phe Phe Gly Ala Val Met
    290                 295                 300

Val Gly
305

(2) INFORMATION FOR SEQ ID NO: 8:

(i) SEQUENCE CHARACTERISTICS:
        (A) LENGTH: 235 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
         (A) ORGANISM: Mus musculus (xi) SEQUENCE DESCRIPTION: SEQ ID NO: 8:

Met Ser Thr Glu Ser Met Ile Arg Asp Val Glu Leu Ala Glu Ala
1               5                   10                  15

Leu Pro Gln Lys Met Gly Gly Phe Gln Asn Ser Arg Arg Cys Leu Cys
            20                  25                  30

Leu Ser Leu Phe Ser Phe Leu Leu Val Ala Gly Ala Thr Thr Leu Phe
        35                  40                  45

Cys Leu Leu Asn Phe Gly Val Ile Gly Pro Gln Arg Asp Glu Lys Phe
    50                  55                  60

Pro Asn Gly Leu Pro Leu Ile Ser Ser Met Ala Gln Thr Leu Thr Leu
65                  70                  75                  80

Arg Ser Ser Ser Gln Asn Ser Ser Asp Lys Pro Val Ala His Val Val
                85                  90                  95

Ala Asn His Gln Val Glu Glu Gln Leu Glu Trp Leu Ser Gln Arg Ala
            100                 105                 110

Asn Ala Leu Leu Ala Asn Gly Met Asp Leu Lys Asp Asn Gln Leu Val
        115                 120                 125

Val Pro Ala Asp Gly Leu Tyr Leu Val Tyr Ser Gln Val Leu Phe Lys
    130                 135                 140

Gly Gln Gly Cys Pro Asp Tyr Val Leu Leu Thr His Thr Val Ser Arg
145                 150                 155                 160

Phe Ala Ile Ser Tyr Gln Glu Lys Val Asn Leu Leu Ser Ala Val Lys
                165                 170                 175

Ser Pro Cys Pro Lys Asp Thr Pro Glu Gly Ala Glu Leu Lys Pro Trp
            180                 185                 190

Tyr Glu Pro Ile Tyr Leu Gly Gly Val Phe Gln Leu Glu Lys Gly Asp
        195                 200                 205

Gln Leu Ser Ala Glu Val Asn Leu Pro Lys Tyr Leu Asp Phe Ala Glu
    210                 215                 220

Ser Gly Gln Val Tyr Phe Gly Val Ile Ala Leu
225                 230                 235
```

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (ix) FEATURE:
        (A) NAME/KEY: CDS
        (B) LOCATION: 1..738

(xi) SEQUENCE DESCRIPTION: SEQ ID NO: 9:

ATGAAGATCC TGACCGAGCG                                              20

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (ix) FEATURE:
        (A) NAME/KEY: CDS
        (B) LOCATION: 1..738

(xi) SEQUENCE DESCRIPTION: SEQ ID NO: 10:

TACTTGCGCT GAGGAGGAGC                                               20

(2) INFORMATION FOR SEQ ID NO: 11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (ix) FEATURE:
        (A) NAME/KEY: CDS
        (B) LOCATION: 1..738

(xi) SEQUENCE DESCRIPTION: SEQ ID NO: 11:

CCTGAGACTC CATGAAAACG C                                           21

(2) INFORMATION FOR SEQ ID NO: 12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (ix) FEATURE:
            (A) NAME/KEY: CDS
            (B) LOCATION: 1..738

(xi) SEQUENCE DESCRIPTION: SEQ ID NO: 12:

TAACCCTTAG TTTTCCGTTG C                                             21

(2) INFORMATION FOR SEQ ID NO: 13:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (ix) FEATURE:
            (A) NAME/KEY: CDS
            (B) LOCATION: 1..738

(xi) SEQUENCE DESCRIPTION: SEQ ID NO: 13:

ACCCAGATGG ACTTCTGTGG                                               20

(2) INFORMATION FOR SEQ ID NO: 14:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (ix) FEATURE:
            (A) NAME/KEY: CDS
            (B) LOCATION: 1..738

(xi) SEQUENCE DESCRIPTION: SEQ ID NO: 14:

TTTCCTTCGA CGTGCTAACG                                               20

(2) INFORMATION FOR SEQ ID NO: 15:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(iii) HYPOTHETICAL: NO (xi) SEQUENCE DESCRIPTION: SEQ ID NO: 15:

GTAATGATCA GTCAACGGGG GAC                                           23

(2) INFORMATION FOR SEQ ID NO: 16:

(i) SEQUENCE CHARACTERISTICS:
            (A) LENGTH: 24 base pairs
            (B) TYPE: nucleic acid
            (C) STRANDEDNESS: single

```
        (D) TOPOLOGY: linear (ii) MOLECULE TYPE: other nucleic acid
         (A) DESCRIPTION: /desc = "primer"

(iii) HYPOTHETICAL: NO (xi) SEQUENCE DESCRIPTION: SEQ ID NO: 16:

CCAGCAAGCT TGCAACCTTA ACCA                                            24

(2) INFORMATION FOR SEQ ID NO: 17:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "primer"

(iii) HYPOTHETICAL: NO (xi) SEQUENCE DESCRIPTION: SEQ ID NO: 17:

GTGGCAACTG GACTTCCAGC G                                               21

(2) INFORMATION FOR SEQ ID NO: 18:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "primer"

(iii) HYPOTHETICAL: NO (xi) SEQUENCE DESCRIPTION: SEQ ID NO: 18:

GCGTTGACTC GAAGGCTCCC G                                               21
```

PROTEIN BELONGING TO THE TNF SUPERFAMILY INVOLVED IN SIGNAL TRANSDUCTION AND METHODS OF USE THEREOF

DOMESTIC PRIORITY CLAIM

The priority is claimed of U.S. Provisional Application No. 60/069,589 filed on Dec. 12, 1997, which is hereby incorporated by reference herein in its entirety.

CROSS REFERENCE TO RELATED APPLICATION

This Application is a divisional of U.S. application Ser. No. 09/873,829, filed May 9, 2002, which is a Continuation-In-Part of U.S. application Ser. No. 09/210,115, filed Dec. 11, 1998, now abandoned, which is a Continuation-In-Part of U.S. application Ser. No. 09/034,099, filed Mar. 3, 1998, now abandoned, which is a Continuation-In-Part of U.S. application Ser. No. 08/989,479, now abandoned, and U.S. Provisional Patent Application 60/069,589, both filed Dec. 12, 1997, all of which are herein incorporated by reference in their entireties.

GOVERNMENT RIGHTS CLAUSE

The research leading to the present invention was supported in part with National Institutes of Health MSTP Grant GM07739 and National Institutes of Health Grant Nos: CA525133, AI13013 and AI13672. The government may have rights in the invention.

FIELD OF INVENTION

The present invention relates to the identification and characterization of a protein belonging to the TNF superfamily which is involved in signal transduction, nucleic acids which encode the protein, and uses for the nucleic acids, the protein, and products derived therefrom, such as antibodies and pharmaceutical compositions. In particular, the protein of the present invention is involved in the modulation of the survivability of mature dendritic cells of the immune system. As a result, the present invention has numerous uses including, but not limited to, modulating immune response to an antigen, diagnosing immune system related conditions, and treating immune system related conditions.

BACKGROUND OF THE INVENTION

Mature dendritic cells are specialized cells that play a role in immune response. They develop from pluripotent hemopoietic stem cells located in bone marrow, and function to present antigens on their surface in order to activate T cells and generate an immune response to a particular antigen. Major Histocompatibility Complex (MHC) proteins, such as Class I MHC molecules and Class II MHC molecules, are involved in the presentation of an antigen on the surface of a mature dendritic cell. The activation of T cells involves a costimulatory process. One signal is from the antigen bound to the MHC molecule on the surface of the mature dendritic cell. This complex interacts with the T cell receptor complex on the surface of the T cell. The other signal results from molecules produced by the mature dendritic cell, which bind to receptors on the T cell. The T cell becomes activated upon receiving both signals, and undergoes an autocrine process wherein it separates from the mature dendritic cell and simultaneously secretes a growth factor like IL-2 along with cell-surface receptors that bind to it. The binding of IL-2 to its receptor stimulates the T cell to proliferate, so long as it has already encountered its specific antigen.

Once the T cell disengages from the mature dendritic cell, another T cell can bind the MHC-antigen complex on the surface of the mature dendritic cell, and be activated. Hence, the longer an antigen presenting mature dendritic cell can survive, the greater the number of T cells it can activate, and the immune response to the specific antigen will be more efficient. However, pluripotent hematopoietic stem cells are constantly undergoing differentiation, and new dendritic cells are constantly being produced. In order to maintain and develop the immune system, mature dendritic cells ultimately undergo apoptosis, wherein its nucleus shrinks and condenses, and the cell shrivels and dies. Newly produced mature dendritic cells are constantly replacing these dead and dying mature dendritic cells.

Members of the tumor necrosis factor (TNF) superfamily can regulate apoptosis in addition to an array of other biological effects, such as cell proliferation, and differentiation. The TNF superfamily currently includes TNF, LT-α, LT-β, FasL, CD40L, CD30L, CD27L, 4-1BBL, OX40L (1) and TRAIL/APO-2L (2, 3) which exhibit the highest homology between their C-terminal, receptor binding domains. The superfamily members are type II membrane proteins that act in an autocrine, paracrine or endocrine manner either as integral membrane proteins or as proteolytically processed soluble effectors. Despite the functional redundancy of this family, specificity may be accomplished by coordinating the spatial and temporal expression of TNF-related ligands and their receptors, and by restricting the expression of signal transduction molecules to specific cell types. TNF receptors interact with a family of molecules called TRAFs (TNF receptor associated proteins) that act as adaptors for the downstream signaling events. Hence, binding of a TNF cytokine to its cognate receptor, which is interacting with TRAF, leads to the activation of several signal transduction pathways, including the activation of the cascade of caspase/ICE-like proteases, which are responsible for apoptosis. Also activated is the nuclear factor-κB (NF-κB) family of transcription factors, which inhibit apoptosis, and mitogen activated protein kinases including the c-Jun N-terminal protein kinases (JNK) and the extracellularly-regulated kinases (ERK).

Moreover, the TNF receptor family can also regulate apoptosis by modulating the expression of the proto-oncogene bcl-2 to produce Bcl-2 and Bcl-2 related proteins. Bcl-2 can suppress apoptosis in the cell by altering transmembrane conductance in mitochondria and preventing the activation of the caspase/ICE-like proteases.

As explained above, the longer an antigen presenting mature dendritic cell can survive, the greater the number of T cells it can activate, and the immune response to the specific antigen will be more efficient. Accordingly, there is a need to be able to increase the active life of antigen presenting mature dendritic cells, and to inhibit apoptosis in such cells.

There is a further need to exploit the increased survivability of antigen presenting dendritic cells to modulate the immune response to an antigen. For example, such increased survivability can be used to diagnose and treat immune system related conditions.

Such increases in mature dendritic cell survivability can also be used to modulate T cell activation in an animal, and thereby modulate the immune response to an antigen.

The citation of any reference herein should not be construed as an admission of such reference as prior art.

SUMMARY OF THE INVENTION

The present invention relates to a novel TNF superfamily member membrane bound protein designated TNF-Related Activation Induced Cytokine, hereinafter referred to as "TRANCE." TRANCE is selectively expressed on T cells, and its receptor, hereinafter referred to as "TRANCE-R", has been detected on the surface of mature dendritic cells located in lymphoid tissues, such as the lymph node and thymus. It has been determined that the interaction of TRANCE with TRANCE-R on the surface of a mature dendritic cell results in the upregulation of the expression by the cell of the $Bcl-x_L$ protein. This protein, related to Bcl-2, suppresses apoptosis in the cell by altering transmembrane conductance in mitochondria and preventing the activation of the caspase/ICE-like proteases. Hence, the exposure of an a mature dendritic cell to TRANCE will increase its life span.

Thus, in a first embodiment, the present invention relates to an isolated nucleic acid molecule comprising the DNA sequence set forth in FIG. 1 (SEQ ID NO:1), or degenerate variants thereof, which correspond to the human TRANCE gene, degenerate variants thereof, fragments thereof, or analogs or derivatives thereof. Moreover, this embodiment extends to an isolated nucleic acid molecule hybridizable to the isolated nucleic acid molecule of FIG. 1 (SEQ ID NO:1), or degenerate variants thereof, under standard hybridization conditions. Yet further, the invention includes isolated nucleic acid molecules that encode polypeptides having an amino acid sequence as set forth in FIG. 2 (SEQ ID NO:2), which is the amino acid sequence of human TRANCE, as well as conservative variants thereof.

In another embodiment, the present invention relates to an isolated nucleic acid molecule comprising the DNA sequence set forth in FIG. 3 (SEQ ID NO: 3), degenerate variants thereof, which correspond to the murine TRANCE gene, degenerate variants thereof, fragments thereof, or analogs or derivatives thereof. Furthermore, this embodiment also includes an isolated nucleic acid molecule hybridizable to the nucleic acid molecule of FIG. 3 (SEQ ID NO:3), or degenerate variants thereof, under standard hybridization conditions. Likewise included are nucleic acids molecules that encode the murine TRANCE protein, having an amino acid sequence as set forth in FIG. 4 (SEQ ID NO:4), as well as conservative variants thereof.

Naturally, the present invention extends to the amino acid sequences of human and murine TRANCE, conservative variants thereof, and fragments of human and murine TRANCE, and conservative variants thereof, wherein the human TRANCE corresponds to the amino acid sequence as set forth in FIG. 2 (SEQ ID NO:2), and the murine TRANCE corresponds to the amino acid sequence as set forth in FIG. 4 (SEQ ID NO:4).

Also included in the present invention are detectably labeled nucleic acids hybridizable to an isolated nucleic acid having a DNA sequence as set forth in FIG. 1 (SEQ ID NO:1), FIG. 3 (SEQ ID NO:3), degenerate variants thereof or fragments thereof.

In addition, the present invention also includes antibodies wherein TRANCE, conservative variants thereof, or a fragment thereof, is the immunogen used in production of the antibodies. These antibodies can be monoclonal or polyclonal. Moreover, the antibodies can be "chimeric" as, for example, they may comprise protein domains from anti-TRANCE antibodies raised against TRANCE in different species.

Moreover, the present invention includes an antibody of TRANCE detectably labeled so that its bonding to TRANCE can be detected. Such detectable labels include enzymes conjugated to the antibody, such as alkaline phosphatase or peroxidase, or radioactive isotopes incorporated into the structure of the antibody.

A further embodiment of the present invention extends to an expression vector containing a nucleic acid molecule which encodes TRANCE, degenerate variants or fragments the isolated nucleic acid molecule, or an isolated nucleic acid hybridizable to the nucleic acid molecule which encodes TRANCE or degenerate variants thereof, under standard hybridization conditions, operatively associated with a promoter. With this expression vector, one may transfect or transform a unicellular host which can then produce TRANCE. The method for expressing TRANCE comprises introducing an expression vector of the present invention into a host cell in a culture to cause a unicellular host into which the vector is introduced, to express an isolated nucleic acid molecule comprising a DNA sequence of SEQ ID NOS: 1 or 3, degenerate variants thereof, fragments thereof, or analogs or derivatives thereof, and thereby produce TRANCE, conservative variants thereof, fragments thereof, or analogs or derivatives thereof, and then recover the TRANCE from the unicellular host, the culture, or both. In one embodiment, an expression vector may comprise the isolated nucleic acid molecule comprising the DNA sequence set forth in FIG. 1 (SEQ ID NO:1), degenerate variants thereof, fragments thereof, or analogs or derivatives thereof, operatively associated with a promoter. In another embodiment, the expression vector comprises the nucleic acid molecule comprising the DNA sequence of FIG. 3 (SEQ ID NO:3), degenerate variants thereof, fragments thereof, or analogs or derivatives thereof, operatively associated with a promoter. An expression vector can be introduced into numerous types of unicellular hosts in order to produce TRANCE, including, but not limited to mammalian cells, insect cells, and bacterial cells.

An expression vector of the present invention can employ numerous promoters to express TRANCE. The promoters applicable to the present invention, include, but are not limited to early promoters of hCMV, early promoters of SV40, early promoters of adenovirus, early promoters of vaccinia, early promoters of polyoma, late promoters of SV40, late promoters of adenovirus, late promoters of vaccinia, late promoters of polyoma, the lac the trp system, the TAC system, the TRC system, the major operator and promoter regions of phage lambda, control regions of fd coat protein, 3-phosphoglycerate kinase promoter, acid phosphatase promoter, or promoters of yeast α mating factor.

As explained above, unicellular hosts can be transformed with an expression of an isolated nucleic acid molecule of the invention. Such unicellular hosts include, but are not limited to, *E. coli, Pseudonomas, Bacillus, Strepomyces*, yeast, CHO, R1.1, B-W, L-M, COS1, COS7, BSC1, BSC40, BMT10 and Sf9 cells. Moreover, mammalian cells can be used as a unicellular host.

The present invention also includes a mammalian cell containing an isolated nucleic acid encoding TRANCE, examples of which are described herein, wherein the isolated nucleic acid sequence is modified in vitro to permit higher expression of a TRANCE polypeptide in the cell by means of a homologous recombinational event, which comprises inserting an expression regulatory sequence, such as a promoter, in functional proximity to the TRANCE polypeptide encoding sequence. In such a cell, the expression regulatory sequence can be a TRANCE promoter and the homologous recombinational event replaces a mutant TRANCE promoter.

However, numerous promoters described herein can also be inserted in such a cell and result in higher expression of TRANCE.

Also included in the present invention are nucleic acid fragments of the isolated nucleic acid molecule of the present invention, degenerate variants thereof, and isolated nucleic acid molecules which hybridize to such fragments or degenerate variants thereof, under standard hybridization conditions. Such fragments may also be inserted into expression vectors and operatively associated with a promoter, which in turn, can be used to cause a host cell in which the vector is introduced to express and thereby produce such fragments of TRANCE.

Accordingly, a method for producing TRANCE fragments is included in the present invention, wherein this method comprises the steps of introducing an expression vector of the present invention containing a fragment of an isolated nucleic acid molecule encoding TRANCE operatively associated with a promoter into a unicellular host in a culture to cause the host cell into which the expression vector is introduced to express the isolated nucleic acid molecule and thereby produce a TRANCE, a conservative variant thereof, a fragment thereof, or analog or derivative thereof, and then recovering the TRANCE from the unicellular host, its culture, or both. Examples of unicellular host cells which can be used in this embodiment of the present invention are described above. In one embodiment, the nucleic acid fragment is from the isolated nucleic acid molecule comprising a DNA sequence as set forth in FIG. 1 (SEQ ID NO:1), and the nucleic acid fragment encodes an active peptide fragment of TRANCE. In another embodiment, the nucleic acid fragment is from the isolated nucleic acid molecule comprising a DNA sequence as forth in FIG. 3 (SEQ ID NO:3), and the nucleic acid fragment encodes an active peptide fragment of TRANCE. The expression vectors of the present invention can be successfully introduced into numerous types of host cells in order to produce TRANCE fragments, including, but not limited to, mammalian cells, insect cells, and bacterial cells.

The present invention further comprises a modulator of immune response in a mammal. The modulator can be a polypeptide having an amino acid sequence as set forth in FIG. 2 (SEQ ID NO:2), conservative variants thereof or a fragment thereof, or a polypeptide having an amino acid sequence as set forth in FIG. 4 (SEQ ID NO:4), conservative variants thereof or a fragment thereof. The modulator can also be an analog or derivative of a polypeptide having an amino acid sequence as set forth in FIG. 2 (SEQ ID NO:2), conservative variants thereof or a fragment thereof, or an analog or derivative of a polypeptide having an amino acid residue sequence as set forth in FIG. 4 (SEQ ID NO:4), or conservative variants thereof, or a fragment thereof. Moreover, the modulator can be a fusion protein comprising an amino acid sequence as set forth in FIG. 2 (SEQ ID NO:2), conservative variants thereof or a fragment thereof, or an amino acid sequence as set forth in FIG. 4 (SEQ ID NO:4), conservative variants thereof, or a fragment thereof. Other forms of the modulator include an anti-sense TRANCE nucleic acid comprising at least one phosphodiester analog bond, and an antibody, wherein its immunogen is selected from the group consisting of a polypeptide having an amino acid sequence as set forth in FIG. 2 (SEQ ID NO:2), conservative variants thereof, or a fragment thereof, a polypeptide having an amino acid sequence as set forth in FIG. 4 (SEQ ID NO:4), conservative variants thereof, or a fragment thereof, an analog or derivative of a polypeptide having an amino acid sequence as set forth in FIG. 2 (SEQ ID NO:2), conservative variants thereof, or a fragment thereof, an analog or derivative of a polypeptide having an amino acid sequence as set forth in FIG. 4 (SEQ ID NO:4), conservative variants thereof or a fragment thereof, a fusion protein wherein its amino acid sequence comprises an amino acid sequence as set forth in FIG. 2 (SEQ ID NO:2), conservative variants thereof, or a fragment thereof, and a fusion protein wherein its amino acid sequence comprises the amino acid sequence set forth FIG. 4 (SEQ ID NO:4), conservative variants thereof, or a fragment thereof.

Moreover, also included in the present invention are analogs or derivatives of TRANCE, wherein a water soluble polymer is conjugated to a TRANCE protein. An example of such a polymer is polyethylene glycol. Moreover, an analog or derivative of a TRANCE protein can be mono-, di-, tri- or tetrapegylated. Moreover, pegylation of TRANCE to from a TRANCE analog or derivative can occur at the N terminus, such that TRANCE is N-terminal monopegylated.

The function of the modulators is to modulate the life span of mature dendritic cells, and hence modulate immune response in the mammal. In particular, exposure of mature dendritic cells to a modulator which is an agonist of TRANCE, such as a polypeptide having an amino acid sequence as set forth in FIG. 2 (SEQ ID NO:2), FIG. 4 (SEQ ID NO:4), conservative variants thereof or a fragment thereof, an analog or derivative of a polypeptide having an amino acid sequence as set forth in FIG. 2 (SEQ ID NO:2), FIG. 4 (SEQ ID NO:4), conservative variants thereof or a fragment thereof, a fusion protein wherein its amino acid sequence comprises the amino acid sequence of FIG. 2 (SEQ ID NO:2), FIG. 4 (SEQ ID NO:4), or conservative variants thereof or a fragment thereof, causes the upregulation of expression of $Bcl-x_L$, which inhibits apoptosis. As a result, mature dendritic cells have a greater active life span than mature dendritic cells not exposed to TRANCE or an agonist modulator thereof, and hence can activate a greater number of T cells than are activated by mature dendritic cells not exposed to a TRANCE agonist modulator.

Also disclosed are TRANCE antagonist modulators which function to decrease the active life span of mature dendritic cells. In particular, these modulators can form a complex with TRANCE on the surface of T cells and prohibit TRANCE from interacting with TRANCE-R. TRANCE antagonist modulators can also form a complex with TRANCE mRNA, and prevent its translation. As a result, the signal transduction of TRANCE is blocked, the upregulation of the expression of $Bcl-x_L$ in mature dendritic cells does not occur, and apoptosis of the cell is not inhibited. Hence, these mature dendritic cells activate less T cells than are activated by mature dendritic cells exposed to TRANCE, and the immune response in the mammal is decreased. The TRANCE antagonist modulators comprise an anti-sense TRANCE nucleic acid comprising at least one phosphodiester analog bond, or an antibody, wherein its immunogen is selected from the group consisting of a polypeptide having an amino acid sequence as set forth in FIG. 2 (SEQ ID NO:2), conservative variants thereof, or fragment thereof, a polypeptide having an amino acid sequence as set forth in FIG. 4 (SEQ ID NO:4), conservative variants thereof or a fragment thereof, an analog or derivative of a polypeptide having an amino acid sequence as set forth in FIG. 2 (SEQ ID NO:2), conservative variants thereof or a fragment thereof, an analog or derivative of a polypeptide having an amino acid sequence as set forth in FIG. 4 (SEQ ID NO:4), conservative variants thereof or a fragment thereof, a fusion protein wherein its amino acid sequence comprises the amino acid sequence of FIG. 2 (SEQ ID NO:2), conservative variants thereof or a fragment thereof, and a fusion protein containing the amino acid sequence of FIG. 4 (SEQ ID NO:4), conservative variants thereof, or a fragment thereof.

The present invention also comprises a TRANCE agonist pharmaceutical composition comprising a modulator which is an agonist of TRANCE, and a pharmaceutically acceptable carrier thereof. The TRANCE agonist modulator comprises a polypeptide comprising an amino acid sequence as set forth in FIG. 2 (SEQ ID NO:2), FIG. 4 (SEQ ID NO:4), conservative variants thereof or a fragment thereof, an analog or derivative of a polypeptide having an amino acid sequence as set forth in FIG. 2 (SEQ ID NO:2), FIG. 4 (SEQ ID NO:4), conservative variants thereof or a fragment thereof, a fusion protein wherein its amino acid sequence comprises the amino acid sequence of FIG. 2 (SEQ ID NO:2), FIG. 4 (SEQ ID NO:4), or conservative variants thereof or a fragment thereof.

As explained above, it has been determined that exposure of an antigen presenting mature dendritic cell to TRANCE causes upregulation of the expression of Bcl-$x_L$, and inhibits apoptosis in a mature dendritic cell. Hence, a TRANCE agonist pharmaceutical composition can be used in a method for treating an immune system related condition in a mammal, wherein the method for treating an immune system related comprises the steps of exposing at least one mature dendritic cell of the mammal to an antigen so that the at least one mature dendritic cell can present the antigen on its surface, and administering to the mammal a therapeutically effective amount of the TRANCE agonist pharmaceutical composition. The exposure of the at least one mature dendritic cell to the antigen can occur in vivo, wherein the antigen is administered to an animal, or ex vivo, wherein the at least one mature dendritic cell is removed from the mammal and exposed to an antigen in a medium which permits the presentation of the antigen on the surface of the at least one mature dendritic cell. The at least one mature dendritic cell presenting the antigen on its surface is then reintroduced into the mammal prior to the administration of a TRANCE agonist pharmaceutical composition. This method increases the active life of a mature dendritic cell presenting an the antigen on its surface. As a result, the number of T cells activated against the antigen presented on the surface of the mature dendritic cell is increased, which results in an increase in a mammal's immune response to the antigen.

The antigen used in this method can be selected from the group consisting of a pathogen or a fragment thereof, a virus or a fragment thereof, and a tumor, or a fragment thereof. The immune system related conditions treated with this method include, but are not limited to viruses which include, but are not limited to adenoviruses, and viruses related to cancer such as HIV, Papillomavirus, Hepatitis-B, Epstein-Barr virus, and cancer itself.

Moreover, the present invention also includes a TRANCE antagonist pharmaceutical composition, which comprises the modulator which is an antagonist of TRANCE and a pharmaceutically acceptable carrier thereof. The modulator which is an antagonist of TRANCE is selected from the group consisting the anti-sense TRANCE nucleic acid comprising at least one phosphodiester analog bond, or an antibody having an immunogen selected from the group consisting of the polypeptide having an amino acid sequence as set forth in FIG. 2 (SEQ ID NO:2) or a fragment thereof, the polypeptide having an amino acid sequence as set forth in FIG. 4 (SEQ ID NO:4) or a fragment thereof an analog or derivative of the polypeptide having an amino acid sequence as set forth in FIG. 2 (SEQ ID NO:2) or a fragment thereof, the analog or derivative of the polypeptide having an amino acid sequence as set forth in FIG. 4 (SEQ ID NO:4) or a fragment thereof, the fusion protein containing the amino acid sequence of FIG. 2 (SEQ ID NO:2), or a fragment thereof, and the fusion protein containing the amino acid sequence of FIG. 4 (SEQ ID NO:4), or a fragment thereof.

Yet further provided in the present invention is a TRANCE antagonist pharmaceutical composition which modulates immune response in a mammal by preventing the upregulation of the expression of Bcl-$x_L$ so that apoptosis is not inhibited in mature dendritic cells. As a result, the life span of mature dendritic cells of a mammal whose immune system is exposed to a TRANCE antagonist pharmaceutical composition is decreased relative to the life span of mature dendritic cells in a mammal whose immune system is not exposed to a TRANCE antagonist pharmaceutical composition. The TRANCE antagonist pharmaceutical composition comprises a modulator which is an antagonist of TRANCE, and is selected from the group consisting of an anti-sense TRANCE nucleic acid comprising at least one phosphodiester analog bond, and an antibody, wherein the immunogen of the antibody is selected from the group consisting of the polypeptide having an amino acid sequence as set forth in FIG. 2 (SEQ ID NO:2) or a fragment thereof, the polypeptide having an amino acid sequence as set forth in FIG. 4 (SEQ ID NO:4) or a fragment thereof, the analog or derivative of the polypeptide having an amino acid sequence as set forth in FIG. 2 (SEQ ID NO:2) or a fragment thereof, the analog or derivative of the polypeptide having an amino acid sequence as set forth in FIG. 4 (SEQ ID NO:4) or a fragment thereof, the fusion protein containing the amino acid sequence of FIG. 2 (SEQ ID NO:), or a fragment thereof, and the fusion protein containing the amino acid sequence of FIG. 4 (SEQ ID NO:4), or active fragment thereof, and a pharmaceutically acceptable carrier thereof.

Moreover, disclosed herein is a method for treating an immune system related condition in a mammal with the TRANCE antagonist pharmaceutical composition, wherein the method comprises administering to the mammal a therapeutically effective amount of the TRANCE antagonist pharmaceutical composition. As a result, the signal transduction of TRANCE from the surface of a T cell is blocked, such that TRANCE can not interact with TRANCE-R, the upregulation of expression of Bcl-$x_L$ in mature dendritic cells does not occur, and apoptosis is not inhibited. An a immune system related condition treated with this method involves overexpression of TRANCE on the surface of T cells, and the life span of mature dendritic cells is of such a length as to be detrimental to the mammal. One example of such a condition is an autoimmune disease, such as rheumatoid arthritis. Another example involves hypersensitivity to an allergen so that the mammal's immune response towards an allergen is less sever. As a result, this method of the present invention can be used in induce anergy in the mammal towards the allergen.

In yet another embodiment, the present invention can be used to diagnose an immune system related condition in a mammal, such as a human. As disclosed herein, TRANCE is a member of the TNF superfamily of proteins, and the exposure of mature dendritic cells to TRANCE ultimately increases the life span of such cells. Hence, just as in the case of other TNF receptor superfamily proteins such as CD40L, wherein its under expression results in an immune system related condition called Hyper IGM syndrome, the under expression of TRANCE can also result in an immune system related condition. Moreover, Autoimmune Human Lymphoproliferative Syndrome (ALPS) is a condition caused by a mutation in the TNF receptor superfamily protein Fas, such that the protein is not expressed, or is expressed in a mutated form with either no activity or decreased activity relative to the wild type Fas protein. Consequently, the under expression or lack of expression of TRANCE in a mammal results in an immune system related condition. Hence, the present invention provides a method for diagnosing such an immune system related condition in a mammal such as a human, wherein the method comprises the steps of removing a bodily sample from the mammal, assaying the bodily sample to determine whether TRANCE is expressed in the sample. The bodily sample can be blood or lymphoid tissue such as lymph node tissue, spleen tissue or thymus tissue.

Such a lack of expression, or under expression, can result from a nonsense mutation in the gene or cDNA encoding TRANCE whereby TRANCE mRNA is not translated, or it is mutated, and the protein product produced from its translation is nonfunctional, or has decreased function. Hence, the isolated nucleic acids of the present invention which encode TRANCE, and the amino acid sequences of TRANCE disclosed in the present invention, can be used for diagnosing an immune system related condition in the mammal, such as autoimmune disease.

Antibodies to the modulators are also encompassed within the scope of the present invention. In particular, these antibodies can be monoclonal or polyclonal. Moreover, chimeric antibodies made against the modulator from at least two species are included in the present invention.

Yet still another embodiment of the present invention is a method of gene therapy for modulating levels of expression of a TRANCE protein in a mammal. Since T cells, like mature dendritic cells, originate from pluripotent hematopoietic stem cells, and are constantly being produced to replace cells which die from apoptosis, an alteration of the TRANCE gene in a pluripotent stem cell, or the addition of copies of the TRANCE gene operatively associated with a promoter to the genome of the stem cell will modulate the level of expression of TRANCE on the surface of T cells. The method for accomplishing such modulation comprises the steps of removing at least one hematopoietic stem cell from the mammal destroying remaining hematopoietic stem cells in the mammal, transfecting the at least one hematopoietic stem cell with a vector containing a nucleic acid molecule which encodes a TRANCE protein such that the nucleic acid molecule becomes incorporated into the genome of the hematopoietic stem cell forming a transfected hematopoietic stem cell, and introducing the transfected hematopoietic stem into the mammal so that the transfected hematopoietic stem cell can self replicate and differentiate within the mammal. In one embodiment, the nucleic acid which encodes TRANCE has a nucleotide sequence as set forth in FIG. 1 (SEQ ID NO:1).

The present invention further extends to a method for modulating immune response to an antigen in an animal so that the animal's immune system can effectively and efficiently destroy the antigen. More specifically, such a method of the present invention comprises the steps of interacting immature dendritic cells from the animal with an antigen ex vivo, so that the cells present the antigen on their surfaces, inducing maturation of the dendritic cells ex vivo, contacting the mature dendritic cells with a modulator of immune response ex vivo, and introducing the mature dendritic cells into the animal. Contacting the antigen presenting mature dendritic cells with TRANCE or a TRANCE agonist ex vivo increases the in vivo survivability of the mature dendritic cells upon their introduction into the animal. As a result, the antigen presenting dendritic cells that have had ex vivo interaction with the antigen, and contact with TRANCE or a TRANCE agonist activate a greater number of T cells in vivo, than can mature dendritic cells for which the method of the present invention was not performed. Consequently, the immune response towards the antigen in an animal for which the present invention was performed is modulated relative to the immune response towards the antigen in an animal in which the method of the present invention was not performed. In a preferred embodiment, the method for modulating immune response involves increasing the immune response to the antigen in the animal. Preferably, the immature dendritic cells of the animal comprise bone marrow derived immature dendritic cells.

Furthermore, the present invention extends to numerous means of interacting immature dendritic cells with an antigen ex vivo, pursuant to a method of modulating immune response as set forth above. For example, immature dendritic cells can be transfected with an expression vector comprising a nucleic acid which encodes the antigen, operatively associated with a promoter. Upon expression of the nucleic acid sequence, the antigen is produced within immature dendritic cells, and then presented on their surfaces. All of the expression vectors and promoters set forth above and having applications in the expression of TRANCE, conservative variants thereof, fragments thereof, or analogs or derivatives thereof, have applications in this aspect of the invention.

In another example of interacting immature dendritic cells with the antigen, immature dendritic cells can be pulsed with the antigen ex vivo. In this type of interaction, the antigen is taken up by the immature dendritic cells, proteolytically processed therein, and presented on the surface of the immature dendritic cells.

Moreover, examples of such antigens against which immune response can be increased include pathogens, or fragments thereof, viruses or fragments thereof, or tumors, or viruses thereof, to name only a few.

Furthermore, examples of modulators having applications in a method for modulating immune response in an animal towards an antigen comprise:
a) a polypeptide having an amino acid sequence of FIG. 2 (SEQ ID NO:2), FIG. 4 (SEQ ID NO:4), conservative variants thereof, or fragments thereof;
b) an analog or derivative of a polypeptide having an amino acid sequence set forth in FIG. 2 (SEQ ID NO:2), FIG. 4 (SEQ ID NO:4), conservative variants thereof, or fragments thereof, or
c) a fusion protein having an amino acid sequence comprising an amino acid sequence set forth in FIG. 2 (SEQ ID NO:2), FIG. 4 (SEQ ID NO:4), conservative variants thereof, or fragments thereof.

Moreover, numerous methods, encompassed by the present invention, are available for introducing dendritic cells which had previously interacted with the antigen, and contacted a TRANCE agonist, into an animal. For example, such dendritic cells can be subcutaneously injected into the animal.

Naturally, methods of modulating immune response to an antigen in a mammal as set forth above extends to mammals, and particularly, humans.

Furthermore, the present invention extends to a method for increasing the viability of a dendritic cell, comprising contacting the dendritic cell with an isolated TRANCE comprising an amino acid sequence of SEQ ID NO:2, conservative variants thereof, fragments thereof, or analogs or derivatives thereof, wherein said dendritic cell is contacted by said isolated TRANCE has an increased viability relative to control dendritic cell not contacted with said isolated TRANCE. In a particular embodiment of the invention, the dendritic cell is contacted with the TRANCE protein while in an immature state. Also, such contact can occur in vitro or in vivo.

Likewise, the present invention extends to a method of increasing viability of a dendritic cell, comprising contacting the dendritic cell with an isolated TRANCE comprising an amino acid sequence of SEQ ID NO:4, conservative variants thereof, fragments thereof, or analogs or derivatives thereof, wherein said dendritic cell contacted by isolated TRANCE has an increased viability relative to a control dendritic cell not contacted with said isolated TRANCE, and such contact can occur in vitro or in vivo.

Moreover, the present invention extends to a method of increasing viability of a dendritic cell, comprising pulsing the dendritic cell with an isolated TRANCE comprising an amino acid sequence of SEQ ID NO:2, conservative variants thereof, fragments thereof, or analogs or derivatives thereof, and pulsing the dendritic cell with an isolated protein which is a member of the Tumor Necrosis Factor (TNF) superfamily of proteins, such that the dendritic cell comprises an increased viability relative to a control dendritic cell not pulsed with TRANCE and the protein. Optionally, the pulsing steps of the invention can occur simultaneously.

In another embodiment, the invention comprises a method of increasing viability of a dendritic cell, comprising pulsing the dendritic cell with isolated TRANCE comprising an amino acid sequence of SEQ ID NO:4, conservative variants thereof, fragments thereof, or analogs or derivatives thereof, and pulsing the dendritic cell with an isolated protein which is a member of the TNF superfamily of proteins, such that the pulsed dendritic cell comprises an increased viability relative to a control dendritic cell not pulsed with isolated TRANCE and the isolated protein. Also, such pulsing of the cell can occur simultaneously.

Numerous proteins well known to the skilled artisan are members of the TNF superfamily, which is explained and described throughout the instant Specification. Particular examples of such proteins include, but certainly are not limited to, CD40L or TNF-α.

The present invention further extends to a method for increasing viability of a dendritic cell of an animal in vivo, comprising:
  Removing an immature dendritic cell from the animal;
  pulsing the immature dendritic cell with an isolated TRANCE comprising an amino acid sequence of SEQ ID NO:2, conservative variants thereof, fragments thereof, or analogs or derivatives thereof;
  inducing the immature dendritic cell to mature; and
  reintroducing the mature dendritic cell into the animal.

Optionally, the dendritic cells can be washed after the pulsing step, and prior to reintroducing them to the animal. Once in the animal, cells which have been treated in this matter will have an increased viability, i.e., a greater life span that dendritic cells which have not been treated according to the teachings of the invention. Furthermore, various forms of TRANCE, including murine TRANCE comprising an amino acid sequence of SEQ ID NO:4, conservative variants thereof, fragments thereof, or analogs or derivatives thereof, have applications in the invention.

Furthermore, the instant invention also enables one of ordinary skill in the art to increase an animal's immune response toward a particular antigen, and thus has applications in treating an immune system related condition. In particular, the present invention extends to a method for increasing immune response in an animal towards an antigen, comprising the steps of:
  Removing an immature dendritic cell from the animal;
  pulsing the immature dendritic cell with an isolated TRANCE comprising an amino acid sequence of SEQ ID NO:2, conservative variants thereof, fragments thereof, or analogs or derivatives thereof;
  pulsing the immature dendritic cell with the antigen;
  inducing the immature dendritic cell to mature; and
  reintroducing the mature dendritic cell into the animal.

Naturally, other TRANCE proteins, such as murine TRANCE comprising an amino acid sequence of SEQ ID NO:4, conservative variants thereof, fragments thereof, or analogs or derivatives thereof, have applications herein.

In a particular embodiment of the invention, the dendritic cells which have been pulsed can be washed prior to reintroduction into the animal.

In addition, numerous antigens can be used in this embodiment of the invention. Examples include, a pathogen, or a fragment thereof, a virus, or a fragment thereof or a tumor, or a fragment thereof. Hence, this aspect of the invention can be readily used to treat an immune system related condition, such as cancer of HIV, because it increases the animal's immune response to an antigen that is associated with the immune system related condition. Hence, such conditions can be readily treated with the invention. Hence, naturally, antigens have applications herein include
  a) a pathogen, or a fragment thereof;
  b) a virus, or a fragment thereof; and
  c) a tumor, or a fragment thereof.

Another embodiment involves Applicants' discovery of a synergistic cooperativity between TRANCE and a protein which is a member of the TNF superfamily in increasing the viability, e.g., the life span of a dendritic cell. In particular, the present invention extends to a method for increasing immune response in an animal towards an antigen, comprising the steps of:
  Removing an immature dendritic cell from the animal;
  pulsing the immature dendritic cell with an isolated TRANCE comprising an amino acid sequence of SEQ ID NO:2, conservative variants thereof, fragments thereof, or analogs or derivatives thereof;
  pulsing the immature dendritic cell with an isolated protein of the TNF superfamily;
  pulsing the immature dendritic cell with the antigen;
  inducing the immature dendritic cell to mature; and
  reintroducing the mature dendritic cell into the animal.

As explained, above, numerous TRANCE proteins, including TRANCE comprising an amino acid sequence of SEQ ID NO:4, conservative variants thereof, fragments thereof, or analogs or derivatives thereof, have applications herein.

Moreover, numerous proteins of the TNF superfamily, which is clearly described herein, have applications in the invention. Particular examples of such proteins comprise TNF-α and CD40L, to name only a few.

23. The method of claim 22, further comprising the step of washing the dendritic cell before reintroducing the dendritic cell into the animal.

Naturally, antigens having applications in the invention include:
  a) a pathogen, or a fragment thereof;
  b) a virus, or a fragment thereof; or
  c) a tumor, or a fragment thereof.

Thus the instant invention readily permits one of ordinary skill in the art to treat an immune system related condition, which is associated with a particular antigen. In particular, the pulsing step of the invention would including pulsing the dendritic cell with an antigen associated with a particular immune system related condition. Thus when the dendritic cell is reintroduced into the animal, the animal's immune response to the particular antigen is increased relative to the immune response in an animal whose dendritic cells were not treated according to the teachings of the invention.

Accordingly, it is an object of the present invention to provide an isolated nucleic acid sequence which encodes a TRANCE protein or a fragment thereof, and degenerate variants of such isolated nucleic acids. Disclosed herein are isolated nucleic acid sequences which encode murine TRANCE and human TRANCE.

It is a further object of the present invention to provide an amino acid sequence for human and murine TRANCE, a conservative variant thereof or a fragment thereof, having utility in a pharmaceutical composition which can modulate immune response in a mammal, or procedure intended to diagnose an immune system related condition in a mammal.

It is a further object of the present invention is to provide an expression vector which can be used to produce TRANCE, a conservative variant thereof, a fragment thereof, or an analog or derivative thereof in a cell, wherein the expression vector comprises the isolated nucleic acid sequence of the present invention which encodes TRANCE, operatively associated with a promoter. A cell transfected with this vector can be made to produce TRANCE, or a fragment thereof, which have applications as described above.

Yet another object of the present invention is to provide a fusion protein containing a TRANCE, a conservative variant thereof, a fragment thereof, or analog or derivative thereof, linked to a different protein, or a fragment of a different protein.

It is a further object of the present invention to provide antibodies to the TRANCE and its subunits, and methods for their preparation, including recombinant means. Such antibodies include polyclonal, monoclonal and chimeric antibodies.

Yet still another object of the present invention is to provide a modulator of immune response in mammal, wherein this modulator regulates the life span of mature dendritic cells, and hence T cell activation. In particular, one object is to provide a TRANCE agonist modulator can bind to TRANCE-R on the surface of a mature dendritic cells and signal the cell, resulting in an upregulation of expression of Bcl-$x_L$ in the cell. This protein inhibits apoptosis and hence prolongs the life span of the mature dendritic cells of the mammal. As a result, the number of T cells activated by a mature dendritic cell exposed to the TRANCE agonist modulator is greater than the number of T cells activated by a mature dendritic cell not exposed to the TRANCE agonist modulator. Hence, immune response is increased.

Yet another object of the present invention is to provide a TRANCE antagonist modulator which can either bind to TRANCE on the surface of a T cell and prevent its binding to TRANCE-R on a mature dendritic cell, or binds to TRANCE mRNA, preventing its function, i.e., translation. The antagonist TRANCE modulator can be an antibody having an TRANCE or a fragment thereof as an immunogen. Moreover, an analog or derivative of TRANCE, and a TRANCE fusion protein can also serve as an immunogen. The antibody of the present invention which is a TRANCE antagonist modulator can be a polyclonal, monoclonal or chimeric antibody, the production of which are all disclosed infra. A TRANCE antagonist modulator can also be an anti-sense nucleic acid molecule having at least phosphodiester analog bond which is complement to TRANCE mRNA such that the anti-sense molecule of the present invention can bind to TRANCE mRNA and prevent its function.

It is a still further object of the present invention to provide pharmaceutical compositions for use in therapeutic methods wherein the pharmaceutical compositions comprise, or are derived from, TRANCE modulators of the present invention, along with a pharmaceutically acceptable carrier. In particular, these pharmaceutical compositions of the present invention can be used to modulate the life span of mature dendritic cells in a mammal. Moreover, they can also be used to modulate T cell activation in a mammal, and hence immune response in a mammal. The present invention disclosed a pharmaceutical composition comprising a TRANCE agonist modulator, as described above, and a pharmaceutically acceptable carrier thereof. Moreover, the present invention discloses a pharmaceutical composition comprising a TRANCE antagonist modulator as described above, and a pharmaceutically acceptable carrier thereof.

It is a still further object of the present invention to provide a method to modulate immune response in a mammal, and in particular, to modulate the life span of mature dendritic cells in the mammal, and hence modulate T cell activation in the mammal. In one such method, a therapeutically effective amount of the pharmaceutical composition comprising the TRANCE agonist modulator is administered to a mammal, along with an antigen. The antigen can be a virus, or a fragment thereof, a pathogen or a fragment thereof, or a tumor, or a fragment thereof. This method can be used to increase immune response against such an antigen. Hence, conditions such as a virus like an adenovirus or HIV, cancer or an infection, can be treated with the method of the invention.

Yet still another object of the present invention is to utilize the pharmaceutical composition invention containing a TRANCE antagonist modulator to treat an immune system related condition, such as autoimmune disease. This method comprises administering to a mammal a therapeutically effective amount of the pharmaceutical composition having the TRANCE antagonist modulator. As a result, the life span of mature dendritic cells of the mammal, and hence its immune response, is decreased. Such a method can also be used to treat a mammal suffering from hypersensitivity to an allergen, whereby this method induces anergy in the mammal towards the allergen.

Another object of the present invention is to provide a method of diagnosing an immune system related condition in a mammal. This method comprises assaying a bodily sample of mammal to determine whether TRANCE is expressed therein. The bodily sample can be blood, or lymphoid tissue, such as lymph node, spleen or thymus tissue. The nucleic acids and antibodies of the present inventions have utility in such an assay.

Also, another object is the use of the present invention in a gene therapy method to modulate the expression of TRANCE in the mammal. The method involves removing a hematopoietic stem cell from a mammal, and destroying all remaining hematopoietic stem cells in the mammal. The stem cell removed is transfected with the expression vector of the present invention, and then reintroduced into the mammal. As a result, the animal will ultimately be repopulated with T cells which express TRANCE.

Still yet another object of the present invention is to increase immune response in an animal against a particular antigen. An increase can result via in vivo contact between a dendritic cell of the animal previously exposed to a particular antigen, and a modulator of immune response, such as a TRANCE agonist described above. Also, immune response against a particular antigen can be increased via ex vivo contact between a modulator of immune response, such as a TRANCE agonist, and a dendritic cell previous exposed to the particular antigen ex vivo.

Still yet another object of the invention is to utilize the heretofore unknown cooperativity between TRANCE and a protein of the TNF superfamily to increase the viability of dendritic cells, and thus increase an animals immune response towards a particular antigen relative to a control animal whose dendritic cells were not pulsed with TRANCE and a member of the TNF superfamily, such as CD40L and TNF-α.

Other objects and advantages will become apparent to those skilled in the art from a review of the ensuing description which proceeds with reference to the following illustrative drawings.

DESCRIPTION OF THE DRAWINGS

FIG. 1. The cDNA nucleic acid molecule encoding human TRANCE (SEQ ID NO:1).

FIG. 2. The amino acid sequence of human TRANCE (SEQ ID NO:2).

FIG. 3. The cDNA nucleic acid molecule encoding murine TRANCE (SEQ ID NO:3).

FIG. 4. The amino acid sequence of murine TRANCE (SEQ ID NO:4).

FIG. 5A. Differential screening of the 8-50.51 gene fragment and Nur77 cDNA with probes from TCR-stimulated KMls8.3.5.1 (KMls8.3.5.1+) and TCR-stimulated KIT50.1.9.1 (KIT50.1.9.1+).

FIG. 5B. Northern analysis of the TRANCE transcript in control, unstimulated (−) and TCR-stimulated (+) KMls8.3.5.1 or KIT50.1.9.1 using 8-50.51 cDNA as a probe. GAPDH was used as a control for poly A(+) RNA loading.

FIG. 6. Sequence analysis of the TRANCE gene.

FIG. 6A. The predicted amino acid sequence of the full length mouse TRANCE protein (mTRANCE) (SEQ ID NO:4) compared with the extracellular domain of human TRANCE (hTRANCE) (SEQ ID NO:2). Dots indicate shared identity between the mouse and human protein and dashes indicate gaps between regions of homology. The transmembrane domain is underlined. Residues labeled with an asterisk (*) indicate a potential N-linked glycosylation sites. The numbers in the left-hand column indicate the amino acid residue positions in the mTRANCE protein. Genbank accession numbers: mTRANCE, AF013170; hTRANCE (partial), AF013171.

FIG. 6B. Amino acid alignment of murine TRANCE (SEQ ID NO:4) with other murine members of the TNF superfamily, such as mFasL (SEQ ID NO:5), mTRAIL (SEQ ID NO:6), mLT-Beta (SEQ ID NO:7), and mTNF-alpha (SEQ ID NO:8). Bars represent the β sheets as estimated from the TNF crystal structure (31). Shaded residues are those that match the consensus sequence. The numbers in the left-hand column indicate the residue positions from the full length protein sequences. Dashes indicate gaps between regions of homology FIG. 7. Expression and regulation of TRANCE.

FIG. 8. Characterization of the recombinant TRANCE-Ecto protein.

FIG. 8A. SDS-PAGE and Coomassie Brilliant Blue staining of purified TRANCE-Ecto. Molecular weight markers are indicated on the left of the figure.

FIG. 8B. JNK activation by TRANCE. Cells were purified as described in the Materials and Methods and stimulated with 500 ng/mL of purified TRANCE-Ecto in 10% glycerol/PBS for the indicated amount of time on M2 coated plates. As a negative control, thymocytes were treated with an equivalent volume of a 10% glycerol/PBS solution on M2 coated plates (control). JNK activation was assessed by incorporation of P-ATP into purified GST-c-Jun(1-79). The band intensities were quantified by phosphoimaging and presented as the fold induction over the unstimulated samples (0 min).

FIG. 10A. BMDC were cultured in complete medium in the presence or absence of recombinant TRANCE (1 μg/mL) for 48 hours then visualized under an inverted light microscope.

FIG. 10B. Duplicate wells containing 3×10$^4$ BMDC were cultured with increasing doses of recombinant TRANCE in complete medium in flat-bottom 96-well plates. The percentage of cell survival was assessed 48 h later by trypan blue exclusion. The average of three experiments, and the SEMs, are shown.

FIG. 10C. 3×10$^4$ BMDC were cultured in complete medium in the presence or absence of recombinant TRANCE (1 μg/mL) or mCD8-CD40L (1/1000 of the culture supernatants). Cell viability was assessed daily by trypan blue exclusion. Representative data of three independent experiments are shown.

FIG. 10D 3×10$^4$ GM-CSF and IL-4 stimulated human monocyte-derived DC were cultured for 2 days in monocyte conditioned medium (MCM) to generate mature DC (26). Thereafter, DCs were cultured in the presence or absence of recombinant TRANCE (1 μg/mL) and cell viability was assessed each day by trypan blue exclusion.

FIG. 10E 50 μg of protein extracted from BMDC cultured for 24 h as described in FIG. 2C were analyzed for Bcl-2 and Bcl-$x_L$ protein expression by western-blot analysis. Basal levels of Bcl-2 and Bcl-xL were determined in day 8 BMDC (0 hr).

FIG. 11A. 2.5×10$^3$ BMDC were cultured with increasing doses of TRANCE in a final volume of 100 μl in triplicate in flat-bottom 96-well plates. After 48 hours 10$^5$ purified allogeneic T cells in 100 μl were added in each well and $^3$[H]-Thymidine incorporation was assessed after 3 days of culture. One experiment of 3 are shown.

FIG. 11B. 2.5×10$^4$ BMDC were cultured in the presence of or the absence of TRANCE or CD40L for 48 h. After washing and counting the cells, dilutions of live cells were, cultured with 10$^5$ purified allogeneic T cells and $^3$[H]-Thymidine incorporation was assessed after 3 days of culture.

FIG. 11C. BMDC were cultured in complete medium for 24 h in the presence (solid lines) or absence (dotted lines) of soluble FLAG-TRANCE (1 μg/mL) and analyzed for the indicated surface markers expression by FACS after gating the live cells. Similar results were obtained after 48 h of culture.

Figure 5:
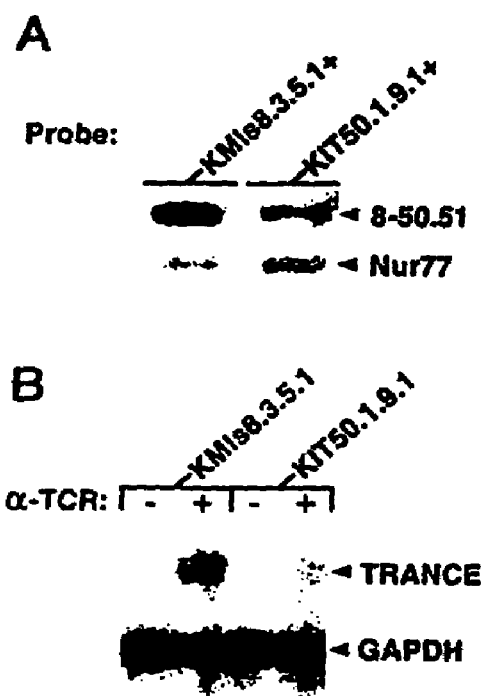
FIG. 5. Identification of a gene defective in KIT50.1.9.1.

Representative results of two independent experiments are shown. (B) The GAPDH signal was used to control for the amount of input RNA and to quantify the relative expression of cytokine mRNA by phosphorimaging.

DETAILED DESCRIPTION

As noted above, the present invention discloses an isolated nucleic acid molecules, or degenerate variants thereof, which encode TRANCE. Examples include an isolated nucleic acid molecule comprising a DNA sequence as set forth in FIG. 1 (SEQ ID NO: 1), degenerate variants thereof, fragments thereof, or analogs or derivatives thereof. This molecule corresponds to an isolated nucleic acid molecule which encodes human TRANCE. Also disclosed herein is an isolated nucleic acid molecule having a DNA sequence as set forth in FIG. 3 (SEQ ID NO:3), degenerate variants thereof, fragments thereof, or analogs or derivatives thereof, or, which corresponds to a isolated nucleic acid molecule which encodes murine TRANCE Moreover, nucleic acids hybridizable under standard hybridization conditions to an isolated nucleic acid molecule comprising a DNA sequence as set forth in FIG. 1 (SEQ ID NO:1) or FIG. 3 (SEQ ID NO:3), or degenerate variants thereof, are also included in the present invention.

Applicants have discovered that TRANCE is expressed on the surface of T cells, and that mature dendritic cells of the immune system have a surface receptor, TRANCE-R. When the T cell interacts with a mature dendritic cell presenting an antigen, TRANCE interacts with TRANCE-R. This interaction causes an upregulation of the expression of Bcl-$x_L$ in the mature dendritic cell, which inhibits apoptosis. As a result, the life span of the mature dendritic cell is increased.

As used herein, the term "TRANCE" refers to an integral membrane bound protein on the surface of T cells, which has been described [Wong et al. *J. Bio. Chem* 272:25190-25194 (1997); this publication is specifically incorporated by reference in its entirety].

The term "TRANCE-R" refers to a TRANCE receptor located on the surface of mature dendritic cells.

An "agonist" of TRANCE according to the invention is a compound that (i) binds to TRANCE-R on the surface of mature dendritic cells; and (ii) activates signal transduction with the mature dendritic cell causing the upregulation of the expression of Bcl-$x_L$ in the mature dendritic cell, which inhibits apoptosis in the cell. The activity of a TRANCE agonist can be evaluated in vitro by numerous methods, including, and by no means limited to, determining the life span of a mature dendritic cell exposed to the agonist and comparing it with the life span of a mature dendritic cell not exposed to the agonist. A TRANCE agonist is expected to increase the life span of mature dendritic cells, and thus be useful in a treatment regimen for immune system related conditions, such as HIV or cancer.

An "antagonist" of TRANCE according to the invention is a compound that blocks TRANCE (or a TRANCE agonist) signal transduction. In one embodiment, the antagonist is an anti-TRANCE antibody which binds to TRANCE on the surface of T cells, and prevents the interaction of TRANCE with TRANCE-R on the surface of mature dendritic cells. In another embodiment, the TRANCE antagonist is an antisense TRANCE nucleic acid comprising at least one phosphodiester analog bond. A TRANCE antagonist is expected to prevent the upregulation of expression of Bcl-$x_L$ in mature dendritic cells so that apoptosis is not inhibited in the cells. As a result, the life span of mature dendritic cells exposed to a TRANCE antagonist are decreased relative to the life span of mature dendritic cells which can interact with TRANCE. Moreover, this decrease in life span results in a decrease in T cell activation, and hence a decrease in immune response.

Also, the term "pulsed" or "pulsing a cell" refer to permitting a cell in cell medium to make contact with a molecule in the cell medium, such as a protein, for a predetermined period of time.

As used herein, the phrase "conservative variant" refers to a protein having at least one amino acid residue of its sequence be mutated to a another amino acid residue having chemical properties similar to the original amino acid residue.

As used herein, the phrase "TNF-Superfamily" or TNF-family, or TNF cytokine family refer to a family of proteins that can regulate apoptosis in addition to an array of other biological effects, such as cell proliferation, and differentiation. Examples of proteins of the TNF-superfamily include, but are not limited to, TNF, LT-α, LT-β, FasL, CD40L, CD30L, CD27L, 4-1BBL, OX40L (1) and TRAIL/APO-2L. Members of the family exhibit the highest homology between their C-terminal, receptor binding domains. The superfamily members are type II membrane proteins that act in an autocrine, paracrine or endocrine manner either as integral membrane proteins or as proteolytically processed soluble effectors.

Isolated TRANCE Protein and Fragments Thereof

Also included in the present invention are amino acid sequences of TRANCE or fragments thereof. In one embodiment of the present invention, human TRANCE is a polypeptide comprising an amino acid sequence as set forth in FIG. 2 (SEQ ID NO:2), murine TRANCE is a polypeptide comprising the amino acid sequence of FIG. 4 (SEQ ID NO:4) or conservative variants thereof. A polypeptide having an amino acid sequence as set forth in FIG. 2 (SEQ ID NO:2) or conservative variants thereof corresponds to human TRANCE.

Anti-TRANCE Antibodies

The present invention also includes antibodies having TRANCE, or a fragment thereof, as an immunogen.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No.

4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

Moreover, the antibodies to TRANCE included in the present invention are detectably labeled in order permit their use in numerous diagnostic assays, such as immunoassays, which are explained herein. Such detectable labels include, but are not limited to, conjugation of the TRANCE antibody to alkaline phosphatase, peroxidase, or the integration of radioactive isotopes into the structure of the antibody.

Expression of TRANCE in Expression Vectors of the Present Invention

According to the present invention, unicellular hosts can be transfected with an expression vector of the present invention. An expression vector of the present invention can comprise an isolated nucleic acid molecule encoding TRANCE, or degenerate variants thereof, operatively associated with a promoter. Such cells can be used to produce TRANCE for use in the elucidation of the molecular genetics of the TRANCE gene, and in the treatment of immune system related conditions.

An isolated nucleic acid molecule comprising a DNA sequence as set forth in FIG. 1 (SEQ ID NO:1), FIG. 3 (SEQ ID NO:3), or degenerate variants thereof, or an isolated nucleic acid molecule which is hybridizable to an isolated nucleic acid comprising a DNA sequence as set forth in FIG. 1 (SEQ ID NO:1), FIG. 3 (SEQ ID NO:3) or degenerate variants thereof, under standard hybridization conditions, can also be used in an expression vector of the present invention.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Clotting A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A DNA sequence is "operatively associated" to an expression control sequence when the expression control sequence controls and regulates the transcription and translation of that DNA sequence. The term "operatively associated" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8). Preferably a minimum length for a hybridizable nucleic acid is at least about 10 nucleotides; preferably at least about 20 nucleotides; and more preferably the length is at least about 30 nucleotides.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667).

Accordingly, the term "sequence similarity" in all its grammatical forms refers to the degree of identity or correspondence between nucleic acid or amino acid sequences of proteins that do not share a common evolutionary origin (see Reeck et al., supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refers to similar or homologous sequences, whether the exact position is identical or different from the molecule to which the similarity or homology is measured. Thus, the term "corresponding to" refers to the sequence similarity, and not the numbering of the amino acid residues or nucleotide bases.

A gene encoding TRANCE, whether genomic DNA or cDNA, can be isolated from any source, particularly from a human cDNA or genomic library. Methods for obtaining these genes are well known in the art, as described above (see, e.g., Sambrook et al., 1989, supra). Accordingly, any animal cell potentially can serve as the nucleic acid source for the molecular cloning of these genes. The DNA may be obtained by standard procedures known in the art from cloned DNA (e.g., a DNA "library"), and preferably is obtained from a cDNA library prepared from tissues with high level expression of the protein (e.g., a T cell cDNA library, since these are the cells that evidence highest levels of expression of TRANCE), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

Moreover, the promoter of the expression vector of the present invention can also includes immediate early promoters of hCMV, early promoters of SV40, early promoters of adenovirus, early promoters of vaccinia, early promoters of polyoma, late promoters of SV40, late promoters of adenovirus, late promoters of vaccinia, late promoters of polyoma, the lac the trp system, the TAC system, the TRC system, the major operator and promoter regions of phage lambda, control regions of fd coat protein, 3-phosphoglycerate kinase promoter, acid phosphatase promoter, or promoters of yeast α mating factor.

The necessary transcriptional and translational signals can be provided on a recombinant expression vector, or they may be supplied by the native gene encoding a TRANCE and/or its flanking regions.

Expression elements of vectors vary in their strengths and specificities. Depending on the host-vector system utilized, any one of a number of suitable transcription and translation elements may be used.

TRANCE proteins of the invention, fragments thereof, conservative variants thereof, or analogs, derivatives, or fusion proteins thereof, may be expressed chromosomally, after integration of the coding sequence by recombination. In this regard, any of a number of amplification systems may be used to achieve high levels of stable gene expression (See Sambrook et al., 1989, supra).

A unicellular host into which the recombinant vector or vectors comprising the nucleic acid encoding TRANCE is cultured in an appropriate cell culture medium under conditions that provide for expression of the TRANCE by the cell. In one embodiment of the present invention, a nucleic acid encoding a TRANCE fusion gene is expressed in a baculovirus expression system as a fusion protein, wherein the extracellular domain of murine TRANCE (amino acid residues 245-316 of FIG. 4 (SEQ ID NO:4)) was fused to human CD8α.

Any of the methods for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

Expression of a TRANCE protein, fragment thereof, conservative variant thereof, or analog or derivative thereof of the invention may be controlled by promoter/enhancer elements disclosed herein, but these regulatory elements must be functional in the unicellular host selected for expression. Promoters which may be used to control gene expression include, but are not limited to, the SV40 early promoter region (Benoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); prokaryotic expression vectors such as the β-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25); see also "Useful proteins from recombinant bacteria" in Scientific American, 1980, 242:74-94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58), alpha 1-antitrypsin gene control region which is active in the liver (Kelsey et. al., 1987, Genes and Devel. 1:161-171), beta-globin gene control region which is active in myeloid cells (Mogram et al., 1985, Nature 315:338-340; Kollias et al., 1986, Cell 46:89-94), myelin basic protein gene control region which is active in oligodendrocyte cells in the brain (Readhead et al., 1987, Cell 48:703-712), myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, *Current Protocols in Molecular Biology*, 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible metallothionein IIa gene promoter, hygromycin selectable marker; Invitrogen), pREP8 (BamH1, XhoI, NotI, HindIII, NheI, and KpnI cloning site, RSV-LTR promoter, histidinol selectable marker; Invitrogen), pREP9 (KpmI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindII, SbaI, BamHI, and Hpa cloning site, TK or XPRT selection).

Once a particular recombinant DNA molecule is identified and isolated, several methods known in the art may be used to propagate it. Moreover, once a suitable host system and growth conditions are established, recombinant expression vectors of the present invention can be propagated and prepared in quantity. As previously explained, the expression vectors which can be used include, but are not limited to, the following vectors or their derivatives: human or animal viruses such as vaccinia virus or adenovirus; and plasmid and cosmid DNA vectors, to name but a few.

In addition, a unicellular host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage [e.g., of signal sequence]) of proteins. Unicellular host cells of the present invention, include, but are not limited to *E. coli, Pseudonomas, Bacillus, Strepomyces*, yeast, CHO, R1.1. B-W, L-M, COS1, COS7, BSC1, BSC40, BMT10 and Sf9 cells.

Appropriate cell lines or host systems can be chosen to ensure the desired modification and processing of the foreign protein expressed. Expression in eukaryotic cells can increase the likelihood of "native" glycosylation and folding of a heterologous protein. Moreover, expression in mammalian cells can provide a tool for reconstituting, or constituting, TRANCE activity. Furthermore, different vector/host expression systems may affect processing reactions, such as proteolytic cleavages, to a different extent.

Vectors are introduced into desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al, 1992, J. Biol. Chem. 267:963-967; Wu and Wu, 1988, J. Biol. Chem. 263:14621-14624; Hartmut et al., Canadian Patent Application No. 2,012,311, filed Mar. 15, 1990).

A method for producing TRANCE a conservative variant thereof, a fragment thereof or analog or derivative thereof, wherein the method is included in the present invention, comprises culturing a transfected or transformed unicellular host described above under conditions that provide for expression of TRANCE, and recovering TRANCE from the unicellular host and the culture.

A Modulator of Immune Response

Also disclosed herein is a modulator of immune response in a mammal, wherein the modulator comprises a polypeptide having an amino acid sequence as set forth in FIG. 2 (SEQ ID NO:2), FIG. 4 (SEQ ID NO:4), conservative variants thereof, or a fragment thereof, an analog or derivative of a polypeptide having an amino acid as set forth in FIG. 2 (SEQ ID NO:2), FIG. 4 (SEQ ID NO:4), conservative variants thereof, or a fragment thereof, a fusion protein wherein its amino acid sequence comprises the amino acid sequence of FIG. 2 (SEQ ID NO:2), FIG. 4 (SEQ ID NO:4), conservative variants thereof or a fragment thereof, an antibody having an immunogen selected from the group consisting of a polypeptide having an amino acid sequence as set forth in FIG. 2 (SEQ ID NO:2), FIG. 4 (SEQ ID NO:4), conservative variants thereof, or a fragment thereof, an analog or derivative of a polypeptide having an amino acid as set forth in FIG. 2 (SEQ ID NO:2), FIG. 4 (SEQ ID NO:4), conservative variants thereof, or a fragment thereof, a fusion protein wherein its amino acid sequence comprises the amino acid sequence of FIG. 2 (SEQ ID NO:2), FIG. 4 (SEQ ID NO:4), conservative variants thereof or a fragment thereof, or an anti-sense TRANCE nucleic acid comprising at least one phosphodiester analog bond.

There are two types of modulators disclosed herein. One type is an agonist of TRANCE, which increases the active life of mature dendritic cells relative to the life of mature dendritic cells not exposed to this modulator, and hence increases T cell activation and overall immune response in the mammal. This type of modulator is selected from the group consisting of a polypeptide having an amino acid sequence as set forth in FIG. 2 (SEQ ID NO:2), FIG. 4 (SEQ ID NO:4), conservative variants thereof, or a fragment thereof, an analog or derivative of a polypeptide having an amino acid as set forth in FIG. 2 (SEQ ID NO:2), FIG. 4 (SEQ ID NO:4), conservative variants thereof, or a fragment thereof, a fusion protein wherein its amino acid sequence comprises the amino acid sequence of FIG. 2 (SEQ ID NO:2), FIG. 4 (SEQ ID NO:4), conservative variants thereof or a fragment thereof.

The other type of modulator is an antagonist of TRANCE. A TRANCE antagonist prevents the interaction of TRANCE with TRANCE-R and decrease the active life of mature dendritic cells relative to the life of mature dendritic cells which can interact with TRANCE. Hence, a TRANCE antagonist modulator decreases T cell activation and overall immune response in the mammal. This type of modulator comprises an anti-sense TRANCE nucleic acid comprising at least one phosphodiester analog bond, or an antibody having an immunogen selected from the group consisting of a polypeptide having an amino acid sequence as set forth in FIG. 2 (SEQ ID NO:2), FIG. 4 (SEQ ID NO:4), conservative variants thereof, or a fragment thereof, an analog or derivative of a polypeptide having an amino acid as set forth in FIG. 2 (SEQ ID NO:2), FIG. 4 (SEQ ID NO:4), conservative variants thereof, or a fragment thereof, a fusion protein wherein its amino acid sequence comprises the amino acid sequence of FIG. 2 (SEQ ID NO:2), FIG. 4 (SEQ ID NO:4), conservative variants thereof or a fragment thereof.

The modulator of present invention also relates to genes encoding analogs or derivatives of TRANCE, that have the same or homologous functional activity as the native TRANCE and homologs thereof from other species. The production and use of derivatives and analogs or derivatives related to TRANCE are within the scope of the present invention. In one embodiment, the derivative or analog is functionally active, i.e., capable of exhibiting one or more functional activities associated with a wild-type TRANCE of the invention. In another embodiment, the modulator is an analog or derivative of a TRANCE fusion protein, which comprises protein domains from at least one specific protein in a construct.

Conservative variants, analogs or derivatives of TRANCE can be made by altering encoding nucleic acid sequences which encode TRANCE, by substitutions, additions or deletions that provide for functionally equivalent molecules. Preferably, derivatives are made that have enhanced or increased functional activity relative to that of native TRANCE.

Due to the degeneracy of nucleotide coding sequences, other DNA sequences which encode substantially the same amino acid sequence as genomic or cDNA TRANCE can be used in the practice of the present invention. These include but are not limited to allelic genes, homologous genes from other species, and nucleotide sequences comprising all or portions of the genes which are altered by the substitution of different codons that encode the same amino acid within the sequence, thus producing a silent change. Likewise, the TRANCE analogs or derivatives of the invention include, but are not limited to, those containing, as a primary amino acid sequence, all or part of the amino acid sequence set forth in FIG. 2 (SEQ ID NO:2) or FIG. 4 (SEQ ID NO:4), including altered sequences in which functionally equivalent amino acids are substituted for these sequences resulting in a conservative amino acid substitution. For example, one or more amino acids within these sequences can be substituted by another amino acid of a similar polarity, which acts as a functional equivalent, resulting in a silent alteration. Substitutes for an amino acid within these sequences may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to effect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

The isolated nucleic acid sequence encoding TRANCE, or an analog or derivative thereof can be produced by various methods known in the art. The manipulations which result in their production can occur at the gene or protein level. For example, the cloned gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog, care should be taken to ensure that the modified gene remains within the same translational reading frame as the native gene, uninterrupted by translational stop signals, in the gene region where the desired activity is encoded.

Additionally, a nucleic acid sequence can be mutated in vitro or in vivo, to create and/or destroy translation, initiation, and/or termination sequences, or to create variations in coding regions and/or form new restriction endonuclease sites, or destroy preexisting ones, to facilitate further in vitro modification. Preferably, such mutations enhance the functional activity of the mutated gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479-488; Oliphant et al., 1986, Gene 44:177; Hutchinson et al., 1986, Proc. Natl. Acad. Sci. U.S.A. 83:710), use of "TAB" linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61-70).

Moreover, the present invention also includes derivatives or analogs of TRANCE produced from a chemical modification. The TRANCE protein of the present invention may be derivatized by the attachment of one or more chemical moieties to the protein moiety. The chemically modified derivatives may be further formulated for intraarterial, intraperitoneal, intramuscular, subcutaneous, intravenous, oral, nasal, pulmonary, topical or other routes of administration. Chemical modification of TRANCE may provide additional advantages under certain circumstances, such as increasing the stability and circulation time of the chemically modified TRANCE and decreasing immunogenicity. See U.S. Pat. No. 4,179,337, Davis et al., issued Dec. 18, 1979. For a review, see Abuchowski et al., in *Enzymes as Drugs* (J. S. Holcerberg and J. Roberts, eds. pp. 367-383 (1981)). A review article describing protein modification and fusion proteins is Francis, 1992, *Focus on Growth Factors* 3:4-10, Mediscript: Mountview Court, Friern Barnet Lane, London N20, OLD, UK.

Chemical Moieties For Derivatization. The chemical moieties suitable for derivatization may be selected from among water soluble polymers. The polymer selected should be water soluble so that the TRANCE analog or derivative does not precipitate in an aqueous environment, such as a physiological environment. Preferably, for therapeutic use of the end-product preparation, the polymer will be pharmaceutically acceptable. One skilled in the art will be able to select the desired polymer based on such considerations as whether the polymer/component conjugate will be used therapeutically, and if so, the desired dosage, circulation time, resistance to proteolysis, and other considerations. For TRANCE, these may be ascertained using the assays provided herein.

Examples of water soluble polymers having applications herein include, but are not limited to, polyethylene glycol, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), dextran, poly(n-vinyl pyrrolidone)polyethylene glycol, propropylene glycol homopolymers, polypropylene oxide/ethylene oxide co-polymers, polyoxyethylated polyols or polyvinyl alcohol. Polyethylene glycol propionaldenhyde may have advantages in manufacturing due to its stability in water.

The polymer may be of any molecular weight, and may be branched or unbranched. For polyethylene glycol, the preferred molecular weight is between about 2 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The number of polymer molecules so attached to TRANCE may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules TRANCE molecules will vary, as will their concentrations in the reaction mixture. In general, the optimum ratio (in terms of efficiency of reaction in that there is no excess unreacted component or components and polymer) will be determined by factors such as the desired degree of derivatization (e.g., mono, di-, tri-, etc.), the molecular weight of the polymer selected, whether the polymer is branched or unbranched, and the reaction conditions.

The polyethylene glycol molecules (or other chemical moieties) should be attached to TRANCE with consideration of effects on functional or antigenic domains of TRANCE. There are a number of attachment methods available to those skilled in the art, e.g., EP 0 401 384 herein incorporated by reference (coupling PEG to G-C SF), see also Malik et al., 1992, Exp. Hematol. 20:1028-1035 (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group include lysine residues and the N-terminal amino acid residues; those having a free carboxyl group include aspartic acid residues glutamic acid residues and the C-terminal amino acid residue. Sulfhydryl groups may also be used as a reactive group for attaching the polyethylene glycol molecule(s). Preferred for therapeutic purposes is attachment at an amino group, such as attachment at the N-terminus or lysine group.

One may specifically desire N-terminally chemically modified TRANCE. Using polyethylene glycol as an illustration of the present compositions, one may select from a variety of polyethylene glycol molecules (by molecular weight, branching, etc.), the proportion of polyethylene glycol molecules to TRANCE molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemical modification may be accomplished by reductive alkylation which exploits differential reactivity of different types of primary amino groups (lysine versus the N-terminal) available for derivatization in TRANCE. Under the appropriate reaction conditions, substantially selective derivatization of TRANCE at the N-terminus with a carbonyl group containing polymer is achieved. For example, one may selectively N-terminally pegylate TRANCE by performing the reaction at a pH which allows one to take advantage of the $pK_a$ differences between the e-amino groups of the lysine residues and that of the a-amino group of the N-terminal residue of TRANCE. By such selective derivatization, attachment of a water soluble polymer to TRANCE is controlled: the conjugation with the polymer takes place predominantly at the N-terminus of TRANCE and no significant modification of other reactive groups, such as the lysine side chain amino groups, occurs. Using reductive alkylation, the water soluble polymer may be of the type described above, and should have a single reactive aldehyde for coupling to TRANCE. Polyethylene glycol proprionaldehyde, containing a single reactive aldehyde, may be used.

Also included in the modulator of the present invention is a fusion protein wherein its amino acid sequence comprises an amino acid sequence as set forth in FIG. 2 (SEQ ID NO:2), FIG. 4 (SEQ ID NO:4), conservative variants, or a fragment thereof. Fusion proteins are the product of a nucleic acid created by the fusion of two distinct genes, or isolated nucleotide fragments of such genes. In one embodiment of the present invention, a soluble fusion TRANCE protein is disclosed which is a FLAG-tagged soluble form of TRANCE generated by cloning a PCR product encoding the TRANCE ectodomain (amino acid residues 72-316 of SEQ ID NO:4) into the HindIII-XhoI sites in the pFLAG/CMV-1 vector (Kodak). In another embodiment, a CD8-TRANCE fusion protein was produced, wherein a the extracellular domain of murine TRANCE (amino acid residues 245-316 of FIG. 4 (SEQ ID NO:4)) was fused to human CD8α (amino acid residues 1-82) and produced in a baculovirus expression system.

The modulator of the present invention also can be an anti-sense TRANCE nucleic acid comprising at least one phosphodiester analog bond. An anti-sense molecule is comprised of RNA or DNA, or analogs or derivatives of RNA or DNA, and has a nucleotide sequence that is complementary to a specific RNA transcript of a gene. It is designed to hybridize to the specific RNA to form a duplex and block the function of the specific RNA, i.e., the translation of RNA. The anti-sense molecule of the present invention can prevent the expression of TRANCE in T cells. Hence, no interaction occurs between TRANCE and TRANCE-R on the surface of mature dendritic cells. Signal transduction of TRANCE is thus blocked, and upregulation of the expression of $Bcl-x_L$ in the mature dendritic cell is prevented. As a result, apoptosis is not inhibited, and the life span of mature dendritic cells is decreased relative to the life span of mature dendritic cells wherein the TRANCE signal transduction is not blocked.

Also included in the modulator of the present invention are antibodies having an immunogen comprising a polypeptide having an amino a polypeptide having an amino acid sequence as set forth in FIG. 2 (SEQ ID NO:2), FIG. 4 (SEQ ID NO:4), conservative variants thereof, or a fragment thereof, an analog or derivative of a polypeptide having an amino acid as set forth in FIG. 2 (SEQ ID NO:2), FIG. 4 (SEQ ID NO:4), conservative variants thereof, or a fragment thereof, or a fusion protein wherein its amino acid sequence comprises the amino acid sequence of FIG. 2 (SEQ ID NO:2), FIG. 4 (SEQ ID NO:4), conservative variants thereof or a fragment thereof. Such antibodies include but are not limited to polyclonal, monoclonal, chimeric, single chain, Fab fragments, and an Fab expression library. The antibodies of the invention may be cross reactive, e.g., they may recognize TRANCE from different species. Polyclonal antibodies have greater likelihood of cross reactivity. Alternatively, an antibody of the invention may be specific for a single form of TRANCE, such as human TRANCE having an amino acid sequence as set forth in FIG. 2 (SEQ ID NO:2), or murine TRANCE, having an amino acid sequence as set forth in FIG. 4 (SEQ ID NO:4).

Various procedures known in the art may be used for the production of polyclonal antibodies to TRANCE polypeptide, fragment thereof, conservative variant thereof, or a derivative or analog thereof, or fusion proteins containing TRANCE or a fragment thereof. For the production of an antibody, various host animals can be immunized by injection with the TRANCE polypeptide, or an analog or derivative (e.g., fragment or fusion protein) thereof, including but not limited to rabbits, mice, rats, sheep, goats, etc. In one embodiment, the TRANCE polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guerin*) and *Corynebacterium parvum*.

For preparation of monoclonal antibodies directed toward the TRANCE polypeptide, or fragment, analog or derivative thereof, or fusion protein containing the amino acid residue sequence of TRANCE or a fragment thereof, any technique that provides for the production of antibody molecules by continuous cell lines in culture may be used. These include but are not limited to the hybridoma technique originally developed by Kohler and Milstein [*Nature* 256:495-497 (1975)], as well as the trioma technique, the human B-cell hybridoma technique [Kozbor et al., *Immunology Today* 4:72 1983); Cote et al., *Proc. Natl. Acad. Sci. U.S.A.* 80:2026-2030 (1983)], and the EBV-hybridoma technique to produce human monoclonal antibodies [Cole et al., in *Monoclonal Antibodies and Cancer Therapy*, Alan R. Liss, Inc., pp. 77-96 (1985)]. In an additional embodiment of the invention, monoclonal antibodies can be produced in germ-free animals utilizing recent technology [PCT/US90/02545]. In fact, according to the invention, techniques developed for the production of "chimeric antibodies" [Morrison et al., *J. Bacteriol.* 159: 870 (1984); Neuberger et al., *Nature* 312:604-608 (1984); Takeda et al., *Nature* 314:452-454 (1985)] by splicing the genes from a mouse antibody molecule specific for a polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. No. 4,946, 778] can be adapted to produce TRANCE polypeptide-specific single chain antibodies. An additional embodiment of the invention utilizes the techniques described for the construction of Fab expression libraries [Huse et al., *Science* 246:1275-1281 (1989)] to allow rapid and easy identification of monoclonal Fab fragments with the desired specificity for a TRANCE polypeptide, its derivatives, analogs or fusion proteins.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a TRANCE polypeptide, one may assay generated hybridomas for a product which binds to a TRANCE polypeptide fragment containing such epitope. For selection of an antibody specific to a TRANCE polypeptide from a particular species of animal, one can select on the basis of positive binding with TRANCE polypeptide expressed by or isolated from T cells of that species of animal, and negative binding with TRANCE from other species.

The foregoing antibodies, particularly if they are detectably labeled, can be used in methods known in the art relating to the localization and activity of the TRANCE polypeptide, e.g., for Western blotting, imaging TRANCE polypeptide in situ, measuring levels thereof in appropriate physiological samples, etc., using any of the detection techniques mentioned above or known in the art. Moreover, a detectable label for an antibody of the present invention includes, but is not limited to, conjugation of the antibody to an enzyme such as alkaline phosphatase or peroxidase, or the incorporation of radioactive isotopes into the structure of an antibody of the present invention.

As explained above, a modulator of the present invention modulates the active life of dendritic cells, and hence effects the immune response and T cell activation in a mammal. It is important to note that the present invention includes modulators that are agonists of TRANCE that increase the life span of mature dendritic cells, and modulators that are antagonists of TRANCE that decrease the life span of mature dendritic cells exposed to them relative to the life span of mature dendritic cells not exposed to a such a modulator.

In particular, modulators of the present invention which are agonists of TRANCE and increase the life span of mature dendritic cells, increase T cell activation, and hence increase immune response in a mammal, include a polypeptide having an amino acid sequence as set forth in FIG. 2 (SEQ ID NO:2), FIG. 4 (SEQ ID NO:4), conservative variants thereof, or a fragment thereof, an analog or derivative of a polypeptide having an amino acid as set forth in FIG. 2 (SEQ ID NO:2), FIG. 4 (SEQ ID NO:4), conservative variants thereof, or a fragment thereof, a fusion protein wherein its amino acid sequence comprises the amino acid sequence of FIG. 2 (SEQ ID NO:2), FIG. 4 (SEQ ID NO:4), conservative variants thereof or a fragment thereof.

Modulators of the present invention that are antagonists of TRANCE prevent the upregulation of expression of Bcl-$x_L$ in mature dendritic cells so that apoptosis in those cells is not inhibited, resulting in a decrease of the life span of such mature dendritic cells, a decrease T cell activation, and a decrease in immune response to an antigen. One such TRANCE antagonist modulator of the present invention is an anti-sense TRANCE nucleic acid comprising at least one phosphodiester analog bond. Another TRANCE antagonist modulator of the present invention is an antibody having an immunogen comprising a polypeptide having an amino acid sequence of FIG. 2 (SEQ ID NO:2), FIG. 4 (SEQ ID NO:4), conservative variants thereof, or a fragment thereof, an analog or derivative of a polypeptide having an amino acid as set forth in FIG. 2 (SEQ ID NO:2), FIG. 4 (SEQ ID NO:4), conservative variants thereof, or a fragment thereof, a fusion protein wherein its amino acid sequence comprises the amino acid sequence of FIG. 2 (SEQ ID NO:2), FIG. 4 (SEQ ID NO:4), conservative variants thereof or a fragment thereof.

Pharmaceutical Compositions

Also provided in the present invention are pharmaceutical compositions comprising modulators of the present invention, and a pharmaceutically acceptable carrier thereof. The phrase "pharmaceutically acceptable" refers to molecular entities and compositions that are physiologically tolerable and do not typically produce an allergic or similar untoward reaction, such as gastric upset, dizziness and the like, when administered to a human.

Such pharmaceutical compositions may be for administration for injection, or for oral, pulmonary, nasal or other forms of administration. In general, comprehended by the invention are pharmaceutical compositions comprising effective amounts of a modulator of immune response of the invention with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder, such as lyophilized form.

Oral Delivery

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate a pharmaceutical composition of the invention (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include the modulator of the present invention and inert ingredients which allow for protection against the stomach environment, and release of the biologically active material in the intestine.

Also specifically contemplated are oral dosage forms of the modulator. The modulator may be chemically modified so that oral delivery of a modulator of the invention is efficacious. Generally, the chemical modification contemplated is the attachment of at least one moiety to the modulator, where the moiety permits (a) inhibition of proteolysis, and (b) uptake into the blood stream from the stomach or intestine. Also desired is the increase in overall stability of the modulator and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: *Enzymes as Drugs*, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-trioxocane. Preferred for pharmaceutical usage, as indicated above, are polyethylene glycol moieties.

For the modulator, the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the modulator or by release of the modulator in the pharmaceutical composition beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The pharmaceutical composition can be included in the formulation as fine multi-particulates in the form of granules or pellets of particle size about 1 mm. The formulation of the pharmaceutical composition for capsule administration could also be as a powder, lightly compressed plugs or even as tablets. The pharmaceutical composition could be prepared by compression.

Colorants and flavoring agents may all be included. For example, a modulator of the invention may be formulated (such as by liposome or microsphere encapsulation) and then further contained within an edible product, such as a refrigerated beverage containing colorants and flavoring agents.

One may dilute or increase the volume of the pharmaceutical composition with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the pharmaceutical composition into a solid dosage form. Materials used as disintegrates include but are not limited to starch, including the commercial disintegrant based on starch, "EXPLOTAB." Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the pharmaceutical composition together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of a pharmaceutical composition of the invention to prevent sticking during the formulation process. Lubricants may be used as a layer between the pharmaceutical composition and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the pharmaceutical composition during formulation and to aid rearrangement during compression might be added. The glidants may include starch, talc, pyrogenic silica and hydrated silicoaluminate.

To aid dissolution of a pharmaceutical composition of the invention into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the modulator either alone or as a mixture in different ratios.

Additives which potentially enhance uptake of the modulator are for instance the fatty acids oleic acid, linoleic acid and linolenic acid.

Controlled release oral formulation may be desirable. A pharmaceutical composition of the invention can be incorporated into an inert matrix which permits release by either diffusion or leaching mechanisms, e.g., gums. Slowly degenerating matrices may also be incorporated into the formulation. Some enteric coatings also have a delayed release effect.

Another form of a controlled release of a pharmaceutical composition of the invention is by a method based on the "OROS" therapeutic system (Alza Corp.), i.e. the pharmaceutical composition is enclosed in a semipermeable membrane which allows water to enter and push the modulator of the composition through a single small opening due to osmotic effects, thus delivering the modulator in vivo.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid.

A mix of materials might be used to provide the optimum film coating. Film coating may be carried out in a pan-coater or in a fluidized bed or by compression coating.

Pulmonary Delivery. Also contemplated herein is pulmonary delivery of a modulator of the present invention. The pharmaceutical composition is delivered to the lungs of a mammal while inhaling and traverses across the lung epithelial lining to the blood stream. Other reports of this include Adjei et al., 1990, Pharmaceutical Research, 7:565-569; Adjei et al., 1990, International Journal of Pharmaceutics, 63:135-144 (leuprolide acetate); Braquet et al., 1989, Journal of Cardiovascular Pharmacology, 13(suppl. 5):143-146 (endothelin-1); Hubbard et al., 1989, Annals of Internal Medicine, Vol. III, pp. 206-212 (a1-antitrypsin); Smith et al., 1989, J. Clin. Invest. 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-γ and tumor necrosis factor α) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the "ULTRAVENT" nebulizer, manufactured by Mallinckrodt, Inc., St. Louis, Mo.; the "ACORN II" nebulizer, manufactured by Marquest Medical Products, Englewood, Colo.; the "VENTOLIN" metered dose inhaler, manufactured by Glaxo Inc., Research Triangle Park, N.C.; and the "SPINHALER" powder inhaler, manufactured by Fisons Corp., Bedford, Mass.

All such devices require the use of formulations suitable for the dispensing of the modulator. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified modulator may also be prepared in different formulations depending on the type of chemical modification or the type of device employed.

Formulations suitable for use with a nebulizer, either jet or ultrasonic, will typically comprise the modulator of the present invention dissolved in water at a concentration of about 0.1 to 25 mg of modulator per mL of solution. The formulation may also include a buffer and a simple sugar (e.g., for protein stabilization and regulation of osmotic pressure). The nebulizer formulation may also contain a surfactant, to reduce or prevent surface induced aggregation of the modulator caused by atomization of the solution in forming the aerosol.

Formulations for use with a metered-dose inhaler device will generally comprise a finely divided powder containing the modulator suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the modulator and may also include a bulking agent, such as lactose, sorbitol, sucrose, or mannitol in amounts which facilitate dispersal of the powder from the device, e.g., 50 to 90% by weight of the formulation. The modulator should most advantageously be prepared in particulate form with an average particle size of less than 10 mm (or microns), most preferably 0.5 to 5 mm, for most effective delivery to the distal lung.

Nasal Delivery. Nasal delivery of a pharmaceutical composition of the invention is also contemplated. Nasal delivery allows the passage of the modulator to the blood stream directly after administering the pharmaceutical composition to the nose, without the necessity for deposition of the product in the lung. Formulations for nasal delivery include those with dextran or cyclodextran.

As explained above, the present invention discloses a TRANCE agonist pharmaceutical composition comprising a modulator which is an agonist of TRANCE comprising a polypeptide having an amino acid sequence as set forth in FIG. 2 (SEQ ID NO:2) or a fragment thereof, a polypeptide having an amino acid sequence as set forth in FIG. 4 (SEQ ID NO:4) or a fragment thereof, the analog or derivative a polypeptide having an amino acid as set forth in FIG. 4 (SEQ ID NO:4) or a fragment thereof, the fusion protein containing the amino acid sequence of FIG. 2 (SEQ ID NO:2) or a fragment thereof, and the fusion protein containing the amino acid sequence of FIG. 4 (SEQ ID NO:4) or a fragment thereof, along with a pharmaceutically acceptable carrier thereof.

Moreover, the present invention discloses a TRANCE antagonist pharmaceutical composition comprising an antagonist of TRANCE comprising an anti-sense TRANCE nucleic acid comprising at least one phosphodiester analog bond, or an antibody having an immunogen selected from the group consisting of the polypeptide having an amino acid sequence as set forth in FIG. 2 (SEQ ID NO:2) or a fragment thereof, the polypeptide having an amino acid sequence as set forth in FIG. 4 (SEQ ID NO:4) or a fragment thereof, the analog or derivative of the polypeptide having an amino acid sequence as set forth in FIG. 2 (SEQ ID NO:2) or a fragment thereof, the analog or derivative of the polypeptide having an amino acid sequence as set forth in FIG. 4 (SEQ ID NO:4) or a fragment thereof, the fusion protein containing the amino acid sequence of FIG. 2 (SEQ ID NO:2), or a fragment thereof, and the fusion protein containing the amino acid sequence of FIG. 4 (SEQ ID NO:4), or a fragment thereof, and a pharmaceutically acceptable carrier thereof.

Methods for Treating Immune System Related Conditions with the Present Invention Pharmaceutical compositions of the present invention discussed above can be used to treat immune system related conditions in a mammal. In particular, included in the present invention is a method to treat an immune system related condition in a mammal with a TRANCE agonist pharmaceutical composition, comprising the steps of exposing at least one mature dendritic cell of the mammal to an antigen so that the at least one mature dendritic cell can present the antigen on its surface, and administering to the mammal a therapeutically effective amount of the TRANCE agonist pharmaceutical composition. In this method, the antigen can include, but is not limited to, a pathogen or a fragment thereof, a virus or a fragment thereof, or a tumor, or a fragment thereof. Hence, the immune system related condition which can be treated with the present invention includes, but is not limited to viruses, such as HIV or cancer.

As explained above, two costimulatory signals are necessary to activate T cells against a particular antigen presented on the surface of a mature dendritic cell. One signal is from the antigen bound to an MHC molecule on the surface of the mature dendritic cell. This complex interacts with the T cell receptor complex on the surface of the T cell. The other signal results from molecules produced by the mature dendritic cell that bind to receptors on the T cell. The T cell becomes activated upon receiving both signals, and undergoes an autocrine process wherein it separates from the dendritic cell and simultaneously secretes a growth factor, such as IL-2, along with cell-surface receptors that bind to it. The binding of IL-2 to its receptor stimulates the T cell to proliferate, so long as it has already encountered its specific antigen. After receiving these signals, the activated T cell departs and the antigen presenting mature dendritic cell is available to activate another T cell. Hence, TRANCE agonist modulators of the present invention mimic TRANCE, and induce upregulation of expression of Bcl-$x_L$ in mature dendritic cells, which inhibits apoptosis of mature dendritic cells. As a result, the life span of the mature dendritic cell exposed to the TRANCE agonist modulator is increased relative to the life span of mature dendritic cells which are not exposed to the TRANCE agonist modulator. This life span increase permits the mature dendritic cells presenting antigens to activate a greater number of T cells than mature dendritic cells not exposed to TRANCE or a TRANCE agonist modulator. Hence, the immune response of the mammal is ultimately increased, since T cell activation contributes to the response. Consequently, this method of the present invention modulates T cell activation in the mammal and permits the treatment of an immune system related condition. The antigen may be a pathogen, or a fragment thereof, a virus, or a fragment thereof, or an antigen from a tumor.

The exposure of the mature dendritic cell to the antigen can occur in vivo or in vitro. If it occurs in vivo, the antigen is administered to the mammal so that mature dendritic cells of the mammal can interact with the antigen and present it on their surfaces. If the exposure occurs ex vivo, then at least one mature dendritic cell is removed from the mammal, exposed to the antigen ex vivo so that the antigen can be presented on its surface, and then reintroduced into the mammal prior to administering the TRANCE agonist pharmaceutical composition.

Moreover, the TRANCE antagonist pharmaceutical composition can also be used in a method to treat immune system related conditions. In particular, disclosed herein is a method for treating an immune system related condition in a mammal comprising administering to the mammal a therapeutically effective amount of a TRANCE antagonist pharmaceutical composition. In this embodiment, the immune system related condition is related to over-expression of TRANCE in the mammal. Autoimmune disease is an example of an immune system related condition involving overexpression of a protein receptor of the TNF superfamily. Since TRANCE is a member of the TNF superfamily, its over expression can also result in an immune system related condition. As a result, this method can be used to treat such a condition. Moreover, this method can be used to treat hypersensitivity in a mammal towards an allergen. Since the TRANCE antagonist pharmaceutical composition decreases immune response, this method can be used to induce anergy in a mammal and decrease the mammal's immune response towards an allergen.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a host cellular mass, or other feature of pathology such as for example, elevated blood pressure, fever, or white cell count as may attend its presence and activity.

Dosages. For all of the above pharmaceutical compositions, as further studies are conducted, information will emerge regarding appropriate dosage levels for treatment of various conditions in various patients, and the ordinary skilled worker, considering the therapeutic context, age and general health of the recipient, will be able to ascertain proper dosing.

Gene Therapy

Also disclosed herein is a method for modifying levels of expression of a TRANCE protein in a mammal, comprising the steps of removing at least one hematopoietic stem cell from the mammal, destroying remaining hematopoietic stem cells in the mammal, transfecting the at least one hematopoietic stem cell with an expression vector comprising an isolated nucleic acid molecule which encodes a TRANCE protein such that the nucleic acid molecule becomes incorporated into the genome of the hematopoietic stem cell, forming a transfected hematopoietic stem cell, and introducing the transfected hematopoietic stem into the mammal so that the transfected hematopoietic stem cell can self replicate and differentiate within the mammal. Such a method can be used to treat a mammal in which TRANCE is not expressed.

The method for removing of a stem cell from a mammal is well known in the art. Moreover, transfecting such a cell with an expression vector of the present invention such that a gene expressing TRANCE operatively associated with a promoter is incorporated into the genome of the stem cell is also included in the present invention. Destruction of remaining stem cells in the mammal can be done with numerous protocols, such as for example, radiation treatments. It is important however, that the mammal be kept in a germ free environment as its immune system will be unable to protect it from foreign viruses, bacteria and pathogens.

After all remaining stem cells of the mammal have been destroyed, the transfected stem cell can be reintroduced into the mammal, wherein it replicates and differentiates. As a result, the immune system is repopulated with T cells that can express TRANCE.

In one embodiment of the present invention, this method is used to modify TRANCE expression in a human, and the expression vector used to transfect the stem cell comprises the isolated nucleic acid sequence of FIG. 1 (SEQ ID NO:1) operatively associated with a promoter.

Diagnostics

The antibodies or isolated nucleic acids of the invention can be used in diagnosis of diseases or disorders associated with apparent defects in TRANCE activity by evaluating the level of expression of a functional TRANCE in a bodily sample. In particular, nucleic acid probes or PCR primers can be used to verify expression of mRNA coding for TRANCE in standard protocols, such as Northern blots, Southern blots, and RT-PCR followed by a Southern blot. Moreover, anti-TRANCE antibodies of the present invention can be used in numerous immunoassays known in the art to detect the expression of TRANCE in a bodily sample. In particular, the antibodies of the present invention can be used to detect expression of TRANCE in cells, and in some instances, to localize its expression on the surface of T cells.

In specific embodiments, a deficiency in TRANCE activity may be evaluated in the context of a disease or disorder associated with a deficiency of a TNF protein. For example, a deficiency of the TNF superfamily protein CD40L results in an immune system related condition called Hyper IGM syndrome. In another example Autoimmune Human Lymphoproliferative Syndrome (ALPS) is a condition caused by a mutation in the TNF superfamily protein Fas, such that the protein is not expressed, or is expressed in a mutated form with either no activity or decreased activity relative to the wildtype Fas protein. Consequently, a deficiency of TRANCE expression in an appropriate bodily sample of a mammal is indicative of the presence of an immune system related condition in the mammal. Appropriate bodily samples include, but are not limited to, blood and lymphoid tissue such as lymph node tissue, spleen tissue, or thymus tissue.

Screening a bodily sample as described above for expression of TRANCE can be accomplished with antibodies of the present invention (including antibodies which are TRANCE antagonist modulators) by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, an anti-TRANCE antibody binding to TRANCE or a fragment thereof is detected by detecting a label conjugated to the TRANCE antibody. In another embodiment, the TRANCE antibody binding is detected by detecting binding of a secondary antibody or reagent to the primary antibody. In a further embodiment, the secondary antibody is labeled. Many means are known in the art for detecting binding in an immunoassay and are within the scope of the present invention.

Moreover, the isolated nucleic acid sequences of the present invention can be used to screen for the expression of TRANCE in a bodily sample. For example, The mRNA from a bodily sample can be isolated, and immobilized on a solid support, such as nitrocellulose or polyvinylidene difluoride (PVDF). This support can then be incubated with the isolated nucleic acid molecule of FIG. 1 (SEQ ID 1) or a fragment thereof conjugated to a label to form a "probe". Numerous methods of labeling DNA are known in the art, including, but not limited to the incorporation of radioactive isotopes into the DNA. This probe is complementary to TRANCE mRNA in a sample and will form a duplex with it. Hence, the detection of this duplex on the solid support indicates that the TRANCE gene in the sample is being transcribed into mRNA, which, in turn, should be translated into a protein.

However, if no such duplex is detected, it is probable that the TRANCE is not being expressed, and hence the mammal lacks functional TRANCE.

Methods of Modulating Immune Response to an Antigen in an Animal

As explained above, Applicants have discovered that the interaction of TRANCE with its receptor on the surface of mature dendritic cells causes the cell's upregulation of expression of apoptosis suppressing $Bcl-x_L$. Hence, the cell's survivability upon exposure to TRANCE is increased.

The present invention further extends to a method for modulating immune response to a particular antigen in an animal, which exploits this property of TRANCE. In particular, the method comprises the steps of:
a) pulsing immature dendritic cells from an animal with an antigen ex vivo so that the immature dendritic cells present the antigen on their surfaces;
b) inducing maturation of the dendritic cells ex vivo;
c) pulsing the mature dendritic cells with a modulator of immune response ex vivo; and
d) introducing the mature dendritic cells into the animal.

In another embodiment, the present invention extends to a method for increasing immune response to a particular antigen in an animal, comprising the steps of:
a) removing the immature dendritic cell from the animal;
a) pulsing immature dendritic cells with TRANCE, a fragment thereof, a conservative variant thereof, or analog or derivative thereof;
b) pulsing the immature dendritic cell with the particular antigen;
c) pulsing the immature dendritic cell with a protein which is a member of the TNF-superfamily;
d) inducing the immature dendritic cell to mature; and
e) reintroducing the mature dendritic cell into the animal.

Contacting, or pulsing dendritic cells presenting the antigen on their surfaces with TRANCE or agonists thereof, increases the viability, e.g., the life span, of the dendritic cells in vivo. As a result, the mature dendritic cells presenting the antigen on their surfaces interact with a greater number of T cells in vivo than they would have interacted with had their survivability not been increased. Consequently, the immune response in the animal towards the antigen presented on the surface of the dendritic cells is increased.

Any type of dendritic cell has applications in this method. Preferably, immature dendritic cells used in a method of the present invention are derived from bone marrow.

Moreover, the present invention extends to modulating immune response towards numerous types of antigens. Examples of antigens toward which immune response can be increased comprise pathogens, or fragments thereof, viruses or fragments thereof, or tumors, or fragments thereof.

Also, numerous methods of interacting the antigen with immature dendritic cells ex vivo are encompassed by the present invention. For example, immature dendritic cells can be pulsed ex vivo with the antigen. In this method, the antigen is taken up by the cell, processed, and then presented on the cell's surface.

Another method of interacting immature dendritic cells with an antigen ex vivo involves transfecting immature dendritic cells with an expression vector comprising a nucleic acid which encodes the antigen, operatively associated with a promoter. In this method, expression of the expression vector within transfected ex vivo immature cells results in the production of the antigen, which is processed, and then presented on the surface of the transfected immature dendritic cells.

Modulators of immune response described infra have applications in a method of modulating immune response involving exposure to dendritic cells ex vivo. In particular, such modulators are TRANCE agonists, and comprise:
a) a polypeptide having an amino acid sequence of FIG. 2 (SEQ ID NO:2), FIG. 4 (SEQ ID NO:4), conservative variants thereof, or fragments thereof;
b) an analog or derivative of a polypeptide having an amino acid sequence set forth in FIG. 2 (SEQ ID NO:2), FIG. 4 (SEQ ID NO:4), conservative variants thereof, or fragments thereof; or
c) a fusion protein having an amino acid sequence comprising an amino acid sequence set forth in FIG. 2 (SEQ ID NO:2), FIG. 4 (SEQ ID NO:4), conservative variants thereof, or fragments thereof.

The present invention may be better understood by reference to the following non-limiting Examples, which are provided as exemplary of the invention.

EXAMPLES

Example 1

TRANCE is a Novel Ligand of the Tumor Necrosis Factor Superfamily that Activates c-Jun N-terminal Kinase in T Cells A novel member of the tumor necrosis factor (TNF) superfamily, designated TRANCE, was cloned during a search for apoptosis-regulatory genes using a somatic cell genetic approach in T cell hybridomas. The TRANCE gene encodes a type II membrane protein of 316 amino acids with a predicted molecular weight of 35 kD. Its extracellular domain is most closely related to TRAIL, FasL and TNF. TRANCE is an immediate early gene upregulated by TCR stimulation and is controlled by calcineurin-regulated transcription factors. TRANCE is most highly expressed in thymus and lymph nodes but not in non-lymphoid tissues and is abundantly expressed in T cells but not in B cells. Cross-hybridization of the mouse cDNA to a human thymus library yielded the human homolog, which encodes a protein 83% identical to the mouse ectodomain. Human TRANCE was mapped to chromosome 13q14 while mouse Trance was located to the portion of mouse chromosome 14 syntenic with human chromosome 13q14. A recombinant soluble form of TRANCE protein composed of the entire ectodomain induced c-Jun N-terminal kinase (JNK) activation in T cells but not in splenic B cells or in bone-marrow-derived dendritic cells. These results suggest a role for this TNF-related ligand in the regulation of the T cell dependent immune response.

The TNF superfamily currently includes TNF, LT-α, LT-β, FasL, CD40L, CD30L, CD27L, 4-1BBL, OX40L (1) and TRAIL/APO-2L (2, 3) which exhibit the highest homology between their C-terminal, receptor binding domains. The family members are type II membrane proteins that act in an autocrine, paracrine or endocrine manner either as integral membrane proteins or as proteolytically processed soluble effectors. Binding to their cognate receptors leads to the activation of several signal transduction pathways: the cascade of caspase/ICE-like proteases, the nuclear factor-κB (NF-κB) family of transcription factors and the mitogen-activated protein kinases including the c-Jun N-terminal protein kinases (JNK), and the extracellularly-regulated kinases (ERK) (4-6).

The biochemical pathways activated by the TNF-related ligands are coordinated to effect a diverse set of biological responses including apoptosis, differentiation, proliferation, and survival (1). Caspases execute the biochemical events leading to apoptosis (4) whereas NF-κB appears to inhibit cell death (7). In addition to its anti-apoptotic role, NF-κB regulates numerous genes, such as cytokines and adhesion molecules, that are critical in triggering and maintaining immune-mediated inflammatory responses (8). TNFR1, TNFR2, CD30, CD40, DR3/wsl-1/TRAMP/Apo-3, and the TRAIL receptor, when stimulated or over expressed, recruit TRAF2, a signal transducing protein that activates JNK in vitro (9). Fas can activate JNK by recruiting the protein Daxx to its death domain (10). Thus, JNK activation appears to be a common signaling event downstream of TNF-related ligand/receptor binding. JNK is linked to lymphocyte activation and proliferation since it can activate c-Jun, a component of the nuclear factor of activated T cells (NFAT) and activator protein-1 (AP-1) (11). Emerging evidence suggests that JNK is also critical in mediating apoptosis in non-lymphoid cells in response to some (10, 12-14), but not all physiologic agonists, e.g., TNFR1 mediated cell death (9, 15).

The expression of TNF-related ligands on T cells are regulated by signaling from the T cell receptor (TCR) and mediate many of its biological effects. FasL, TNF and CD30L are responsible for TCR-mediated apoptosis of T cells and immature thymocytes (16, 17). Seven of the TNF superfamily members, in conjunction with TCR-stimulation, can enhance T cell proliferation (1). Therefore, upregulation of TNF cytokine members and their receptors by the TCR may provide an autocrine costimulatory mechanism to enhance the cells' own proliferation after stimulation with antigen (1). The TCR also upregulates TNF-related ligands for the purposes of B cell co-stimulation, protection against Ig antigen-receptor induced apoptosis and antibody isotype switching (18-20), dendritic cell activation and differentiation (21), and of inducing apoptosis in virally infected cells or transformed cells (22).

To investigate the molecular regulation of TCR-mediated apoptosis a cloning strategy based on somatic cell genetics (23) was used, in which gene expression in mutant T cell hybridomas, resistant to TCR-mediated cell death yet capable of other receptor-associated functions (e.g. IL-2 secretion), is compared with gene expression in wild-type cells sensitive to TCR-mediated cell death. Such a strategy should yield genes associated with apoptosis and not activation although it is possible to obtain genes involved in other processes. This technique was used successfully to clone the gene TDAG51, a gene required for Fas expression and TCR-mediated cell death (24). Using similar methods new member of the TNF superfamily, designated TRANCE (TNF-related activation-induced cytokine) was cloned, which is predominantly expressed on T cells and in lymphoid organs and is controlled by the TCR through a calcineurin-regulated pathway. A soluble form of the ligand consisting only of the extracellular domain can activate c-Jun N-terminal kinase (JNK) specifically in T cells but not in B cells or bone-marrow derived dendritic cells. These results suggest that TRANCE plays a specific role in regulating T cell functions.

Materials and Methods

Subtractive hybridization and differential screening. $1 \times 10^8$ KMls8.3.5.1 or KIT50.1.9.1 T cell hybridomas, were incubated on 15 cm plates coated with 5 μg/mL of H57-597 (α-TCR Ab) as previously described (24). Poly A(+) RNA was extracted using a FastTrack 2.0 mRNA isolation kit (Invitrogen) and 2 μg from TCR-stimulated KMls8.3.5.1 (KMls8.3.5.1+) and TCR-stimulated KIT50.1.9.1 (KIT50.1.9.1+) was used to make tester and driver cDNA, respectively. Suppression subtractive hybridization was performed using the PCR-select cDNA subtraction kit according to the manufacturer's protocol (Clontech). Briefly, tester and driver was digested with RsaI and the tester was ligated to adapter DNA. After two hybridizations with the tester and driver cDNA (20 h and 8 h) the resulting mixture was diluted 1:1000 and amplified by PCR using flanking and nested primers to produce a subtracted and normalized PCR fragment library. The efficiency of subtraction was verified via Southern blot analysis of the unsubtracted and subtracted PCR products using a $^{32}$P-labeled GAPDH cDNA probe. 26 primary cycles and 18 secondary cycles of PCR amplification yielded the greatest signal:noise ratio estimated by comparing the amount of PCR product synthesized to the amount of GAPDH in the subtracted product. Using these conditions, subtracted PCR products were TA cloned into the pCR2.1 plasmid (Invitrogen). To screen differentially expressed products 100 ng of plasmid DNA containing the subtracted fragments were immobilized on duplicate nitrocellulose filters using a slot blot apparatus (Schleicher and Schuell) and hybridized to cDNA probes ($1 \times 10^7$ cpm/mL) derived from either KIT50.1.9.1+ or KMls8.3.5.1+polyA(+) RNA. Signals were quantified using a phosphorimager (Molecular Dynamics).

Full length cloning of murine and human TRANCE cDNA. A subtracted cDNA fragment, designated 8-50.51, which scored positive in the differential screening assay was used to screen a λZAP cDNA library derived from KMls8.3.5.1+ (24). The longest clone (2.2 kb) was sequenced with a Sequenase 2.0 kit (United States Biochemical) over both sense and anti-sense directions using a series of oligonucleotide primers. To clone the human homolog a BamHI-BamHI fragment corresponding to TRANCE (nt 366-1035) was used to screen $1 \times 10^6$ phage from a λgt11 5'-Stretch Plus human leukemia library (Clontech) using low stringency hybridization conditions. A partial human clone was sequenced using the same method described for murine TRANCE.

Mouse cell purification. All cells were harvested from 4-8 week old BALB/c mice (The Jackson Laboratory). T cell enrichment: T cells were purified from $5 \times 10^7$ lymph node cells using a T cell enrichment kit (Biotex). B cell enrichment: $5 \times 10^7$ splenocytes were negatively selected for T cells via magnetic beads conjugated to anti-mouse Thy 1.2 following the manufacturer's protocol (Dynabeads Thy 1.2, Dynal). Bone-marrow derived-dendritic cell enrichment (BMDC): Mature BMDC were isolated as previously described (25). Proliferating and apoptotic lymph node T cells (LNTC): LNTC were harvested and treated with concanavalin A (ConA; 5 μg/mL) plus IL-2 (10 U/mL) for 48 h and then with IL-2 alone (50 U/mL) for 48 h to yield proliferating T cells (17). To induce cell death, the proliferating T cells were incubated on α-CD3ε (145-2C11) coated plates for 6-72 hours as previously described (17). Using these conditions, ~50% of the cells are dead by 48 h versus ~5% cell death in the cells treated with ConA plus IL-2 alone. The purity of T, B and BMDC enriched fractions was tested by FACS and in all cases was greater than 90%.

Northern Analysis and Semi-Quantitative PCR. Expression and regulation of TRANCE in T cell hybridomas was determined by Northern blot analysis of poly A(+) RNA extracted at the indicated time points from the following samples: unstimulated or TCR-stimulated cells either in the presence of media alone, FK506 (10 ng/mL; Fujisawa USA) or cycloheximide (1 μg/mL; Sigma). The 8-50.51 fragment was used as a probe. To determine TRANCE expression in mouse tissues or in stimulated LNTC, total RNA was extracted from various organs or cells as previously described (24) and 20 μg from each sample was analyzed by Northern blot using the TRANCE full length cDNA as a probe. A 28S ribosomal RNA probe or a GAPDH cDNA probe was used to control for RNA loading. For semi-quantitative PCR analysis total RNA was extracted from T or B cell enriched fractions using the RNA Isolation Kit (Stratagene) and first strand cDNA was transcribed from 1 μg of RNA using Superscript RT (Gibco BRL) following the protocol provided by the supplier. The first strand reaction was diluted 1:100, allowing amplification to occur as linear function of starting concentrations, and was subjected to PCR using the following conditions: β-Actin: (sense: 5'-ATG AAG ATC CG ACC GAG CG-3" (SEQ ID NO:9), antisense: 5'-TAC TTG CGC TGA GGA GGA GC-3' (SEQ ID NO: 10), 94° C. 30 sec, 50° C. 1 min, 72° C. 1 min for 30 cycles). TRANCE: sense: 5'-CCT GAG ACT CCA TGA AAA CGC-3' (SEQ ID NO: 11), antisense: 5'-TAA CCC TTA GTT TTC CGT TGC-3' (SEQ ID NO:12), 94° C. 30 sec, 52° C. 1 min, 72° C. 1 min for 30 cycles). The PCR products were analyzed by Southern blot as previously described (24).

Expression and Purification of Soluble TRANCE. A FLAG-tagged soluble form of TRANCE was generated by cloning a PCR product encoding the TRANCE ectodomain (amino acid residues 72-316 of FIG. 2 (SEQ ID NO:2)) into the HindIII-XhoI sites in the pFLAG/CMV-1 vector (Kodak). The open reading frame and FLAG fusion was confirmed by sequencing. 293T cells were transfected with the expression construct (20 μg/10 cm plate) by the calcium phosphate method. Supernatant was harvested 72 h later, passed through a 0.45 μm filter, incubated with the α-FLAG M2 affinity gel (Kodak) and eluted with the FLAG peptide (250 μg/mL; Kodak) as outlined in the manufacturer's protocol. The eluant was dialyzed against PBS, adjusted to 10% glycerol and the protein concentration was ascertained in a BCA protein assay (Pierce).

Chromosomal localization of murine and human TRANCE. Human TRANCE mapping: A Genebridge 4 radiation hybrid mapping panel was obtained from Research Genetics, Inc. (Huntsville, Ala.). Hybrid DNA was subjected to PCR (94° C. 20 sec, 55° C. 15 sec, 72° C. 1 min, for 30 cycles) with primers derived from the 3'-UTR of the human TRANCE mRNA. Analysis of the data was performed using the radiation hybrid mapping server at the Whitehead Institute/MIT Center for Genome Research as previously described (26). Murine TRANCE mapping: Murine TRANCE was mapped using an intersubspecific backcross. A TRANCE specific genomic DNA fragment of 582 bp was amplified by PCR using synthetic oligonucleotide primers (5'-ACC CAG ATG GAC TTC TGT GG-3' (SEQ ID NO: 13), 5'-TTT CCT TCG ACG TGC TAX CG-3' (SEQ ID NO: 14), and a single stranded conformation polymorphism between 57BL/6J and CAST/Ei mice was detected in MDE gels as previously described (27). The polymorphism was mapped on a panel of DNA from 57 C57BL/6J×CAST/Ei)F1× C57BL/6J backcrossed mice, donated by The Jackson Laboratory Mouse Mutant Resource, which contains a large number of previously typed markers on all chromosomes (28).

c-Jun N-terminal kinase assays. $2-5 \times 10^6$ cells were incubated for 1-2 hours at 37° C., 5% $CO_2$ on plates coated with the α-FLAG M2 antibody (10 μg/mL). The cells were treated with either soluble TRANCE in 10% glycerol/PBS solution or an equal volume of 10% glycerol/PBS solution before harvesting at the indicated time points and frozen in a dry ice/ethanol bath. Cells were lysed with Triton Lysis Buffer [20 mM Tris.Cl (pH 7.5), 137 mM NaCl, 1 mM PMSF, 5 mM EDTA, 2 mM EGTA, 1 mM $Na_3VO_4$, 25 mM β-glycerophosphate, 50 mM NaF, 10 mM sodium pyrophosphate, 15% glycerol, 1% Triton X-100], spun down in a microcentrifuge to remove cell debris, and supernatants were incubated with goat α-JNK1 Ab (0.3 μg; Santa Cruz Biotechnology) for 2 h at 4° C. Protein A sepharose was added for 1 h and the beads were washed 2 times with Triton Lysis Buffer then 2 times with JNK Reaction Buffer [25 mM HEPES (pH 7.4), 25 mM β-glycerophosphate, 25 mM $MgCl_2$, 2 mM DTT, 0.1 mM $Na_3VO_4$]. For the kinase reaction, 30 μL of JNK Reaction Buffer containing 1.5-3.0 μg of purified GST-c-Jun(1-79) (generously donated by Dr. H. Hanafusa, The Rockefeller University), 0.5 μCi of $\gamma$-$^{32}$P ATP and ATP (20 μM) was incubated with the immunoprecipitated JNK for 20 min at 30° C. The reactions were stopped with 2× loading buffer, boiled for 5 min and run on a 12% SDS-PAGE gel as previously described. (29)

Results and Discussion

Identification of mouse and human TRANCE. The molecular defects in KIT50.1.9.1, a mutant T cell hybridoma resistant to TCR-mediated apoptosis (23) were investigated by comparing its gene expression with that of KMls8.3.5.1, the parental cell line sensitive to TCR-mediated apoptosis. Differentially expressed genes between TCR-stimulated KIT50.1.9.1 (KIT50.1.9.1+) and TCR-stimulated KMls8.3.5.1 (KMls8.3.5.1+) were isolated using suppression subtractive hybridization, a cDNA subtraction technique based on suppression PCR that is sensitive to rare transcripts (30). After subtracting KIT50.1.9.1+cDNA from KMls8.3.5.1+cDNA a mini-library was generated by randomly subcloning the subtracted PCR products. The plasmid library was then subjected to differential screening using KIT50.1.9.1+cDNA and KMls8.3.5.1+cDNA as probes. Of the 347 plasmids screened, 76 produced a stronger signal with the KMls8.3.5.1+probe than with the KIT50.1.9.1+probe. One positive, designated 8-50.51, is shown in FIG. 5A. In contrast, Nur77, a gene whose expression is induced normally in both cells produced similar signals with both probes indicating that an equivalent amount of labeled probe was used from each cell line. Sequencing of 8-50.51 revealed an 87 bp DNA fragment with no homology to any genes in the Genebank database. To confirm differential expression of 8-50.51, a Northern blot containing unstimulated and TCR-stimulated KMls8.3.5.1 and KIT50.1.9.1 poly A(+) RNA was probed. The probe identified a 2.2-2.3 kB message that was highly induced in TCR-stimulated in KMls8.3.5.1 but only weakly induced in TCR-stimulated KIT50.1.9.1 (FIG. 5B).

Using 8-50.51 as a probe we screened a KMls8.3.5.1+ cDNA library was screened to obtain a full length clone. The full length cDNA (FIG. 6A) is 2237 bp in length with a canonical Kozak consensus sequence starting at 137 bp from the 5' end of the clone. This translation initiation site permits the synthesis of a 316 amino acid protein with a hydrophobic transmembrane domain and no identifiable signal sequence strongly suggesting a type II integral membrane protein topology. A comparison of extracellular domains revealed similarity of the protein with mouse TRAIL (20%), FasL (19%) and TNF (17%). Alignment with selected members of the TNF superfamily demonstrates high identity, especially in regions forming the β strands as estimated from the TNF crystal structure (31) (FIG. 6B). Due to the clear similarity of this gene with the TNF superfamily members, this protein was termed TRANCE. A FLAG-tagged full length protein with an estimated molecular weight of 35 kD was detected by Western blotting as a ~45 kD band suggesting that TRANCE is post-translationally modified. Putative N-linked glycosylation sites are indicated (FIG. 6A). The FLAG-tagged TRANCE could not be immunoprecipitated with Fas, DR3/wsl-1/TRAMP/Apo-3, CD30, TNFR2, or HVEW/ATAR immunoadhesins suggesting that TRANCE does not bind to these receptors. A partial human TRANCE cDNA, cloned from a human thymus cDNA library, is 83% identical to the mouse TRANCE ectodomain suggesting that the function of this gene is highly conservative between mouse and human.

Figure 7:
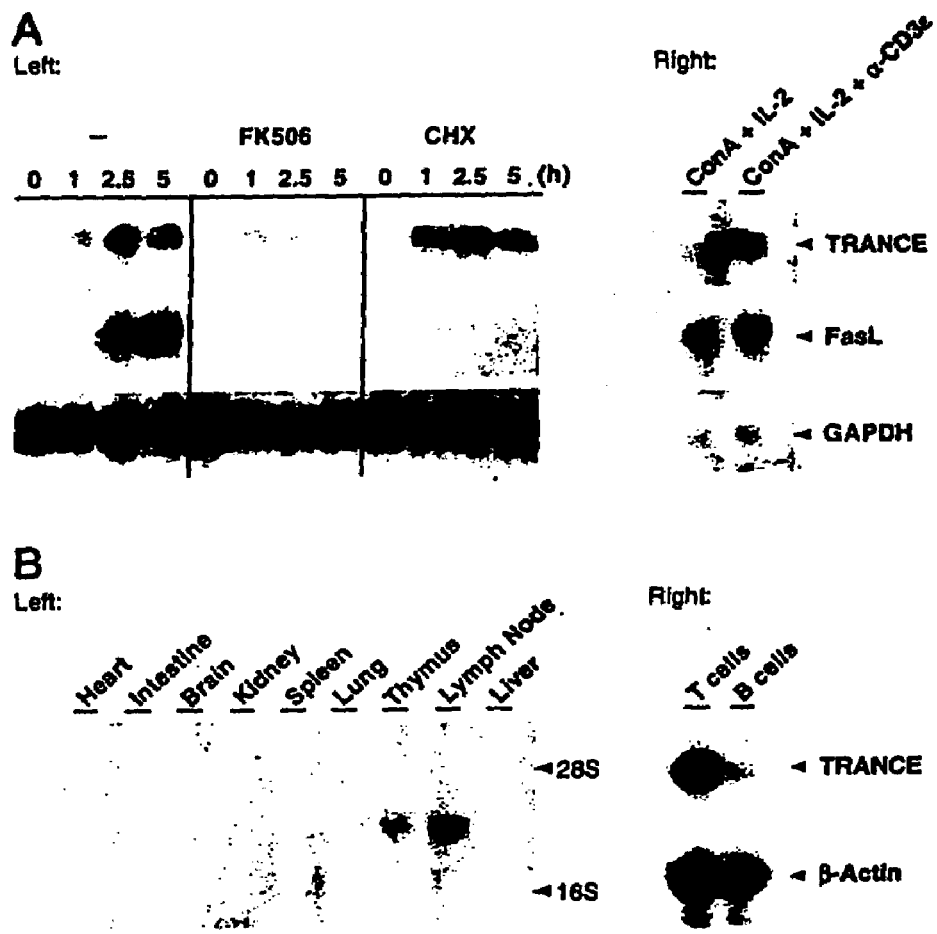
FIG. 7A. Left: Effect of FK506 and cycloheximide (CHX) on TCR-induced upregulation of TRANCE and FasL by Northern analysis. T cell hybridomas were stimulated on α-TCR Ab coated plates for the indicated amount of time in the presence of media alone (−), FK506 (10 ng/mL) or CHX (1 μg/mL). Right: Northern of TRANCE and FasL expression in LNTC stimulated with ConA+IL-2 or ConA+IL-2+α-CD3ε. The blots were stripped and reprobed with GAPDH to normalize for the amount of loaded RNA.
FIG. 7B. Left: Northern analysis of TRANCE in various mouse tissues. 28S and 16S ribosomal RNA is indicated. Equal amounts of RNA were loaded as determined with a 28S ribosomal RNA probe. Right: RT-PCR and Southern blot analysis of TRANCE in T and B cell enriched populations. Amplification of β-actin was used to control for the amount of RNA template used in the PCR reaction.

Regulation and tissue distribution of TRANCE. The signaling capabilities and biological functions of the TNF superfamily appear redundant. Yet specificity clearly exists, as shown by gene-knockout studies, in which the deletion of one superfamily member cannot be fully compensated by the others. Specificity may be achieved by restricting the expression of these genes to particular cells and tissues and or by linking their induction to different regulatory pathways. Temporal regulation of the TNF superfamily members may also be important in properly coordinating their biological effects in vivo (1). The regulation of TRANCE induction by the TCR was studied in T cell hybridomas with cycloheximide (CHX), an inhibitor of translation, and FK506, a FKBP ligand that inhibits calcineurin (PP-2B) (FIG. 7A, Left). Without inhibitors, TRANCE expression began 1 h after TCR-stimulation and reached a maximal level at 2.5 h. FasL was also highly induced by TCR-stimulation, however, its expression began at a later time point. CHX failed to inhibit the induction of TRANCE by the TCR indicating that TRANCE is an immediate early gene. In contrast, CHX completely abrogated the induction of FasL by the TCR. Thus, TRANCE, like TNF (32), is an immediate early gene with a relatively rapid onset of expression after TCR stimulation whereas FasL induction is delayed and requires de novo protein expression for its synthesis. Cyclosporin A, and FK506, both inhibitors of calcineurin, repress TCR-mediated TNT induction (32) and NFATp deficient mice fail to upregulate FasL, CD40L and TNF expression in response to TCR stimulation (33). Therefore, FasL, CD40L and TNF appear to be regulated by calcineurin-dependent signaling pathways involving the NFAT family of transcription factors. In the presence of FK506, the induction of TRANCE and FasL is blocked (FIG. 7A, Left) suggesting that TRANCE, like several other TNF-related ligands, is controlled by NFAT proteins.

To examine TRANCE regulation in non-transformed cells, Northern analysis was performed on concanavalin A (ConA) and IL-2 stimulated LNTC, a model of antigen-mediated T cell proliferation and on proliferating LNTC re-stimulated with α-CD3ε Ab, a model of peripheral T cell clonal deletion (17). ConA and IL-2 stimulated T cells express relatively low amounts of TRANCE message whereas FasL expression is high (FIG. 7A, Right). However, after re-stimulation with an α-CD3ε Ab TRANCE was significantly upregulated suggesting that TRANCE may play a role in antigen-induced T cell death.

Northern blot analysis revealed that TRANCE expression is restricted to the thymus and lymph node (FIG. 7B, Left). This pattern of expression differs from the pattern exhibited by TRAIL/Apo-2L and FasL, which are expressed in both lymphoid and non-lymphoid organs, but is similar to the pattern exhibited by lymphotoxin-β, which is restricted to spleen. In addition, TRANCE is abundant in lymph node-derived T cells (LNTC) but not in splenic B cells (FIG. 7B, Right). Thus, TRANCE is expressed specifically in T cells and in T cell rich organs, although its expression in other cell-types cannot be ruled out.

Chromosomal Mapping of TRANCE. The murine TRANCE locus was mapped to mouse chromosome 14 by use of an intersubspecific backcross (27, 28). In 57 backcross mice TRANCE showed two recombinants with the Rb1 locus (Lod 13.4) and nine recombinants with Rps10-rs4 (Lod>>6.4). After inferring marker genotypes from recombinant mice, incorporating other markers and minimizing double crossovers, the gene order and map distances (cM±SE) were: Rb1–(1.5±1.0)–TRANCE–(1.5±1.1)–Rps10-rs4–(3.7±1.6)–Rpl36-rs2–(6.4±2.1)–Rpl7-rs2–(4.2±1.7)–Dct. TRANCE is located on mouse chromosome 14 near a non-MHC locus suggestively linked to autoimmune nephritis in NZB mice (34), implicating TRANCE in the regulation of immune-tolerance. Human TRANCE was localized by radiation hybrid mapping at 3.98 cR (approximately 800 kB) from the marker, CHLC.GATA6B07 (D13S325), located at 117 cR on the WI radiation hybrid framework of chromosome 13. Superposition of this map with the cytogenetic map of human chromosome 13 allowed the assignment of TRANCE to chromosomal band 13q14.

Biochemical function of TRANCE. A soluble fusion protein comprising the entire ectodomain of TRANCE fused to an N-terminal FLAG epitope (TRANCE-Ecto) was constructed to examine the biochemical function of TRANCE and to identify the cellular targets that respond to this protein. TRANCE-Ecto, when expressed in 293T cells and purified to homogeneity, has an apparent molecular weight of ~37 kD by SDS-PAGE analysis (FIG. 8A). Since its calculated molecular weight is 27.5 kD, this data suggests that the TRANCE-Ecto protein is post-translationally modified similarly to the FLAG-tagged membrane bound protein. JNK is a signal transducing molecule commonly activated by TNF-related ligands. Therefore, JNK activation was assessed by the soluble TRANCE protein in thymocytes, LNTC, purified splenic B cells and bone-marrow-derived dendritic cells (BMDC). JNK is rapidly activated in thymocytes (3-fold induction at 10 min), LNTC (2-fold induction at 5 min) (FIG. 4B) and T cell hybridomas (2-fold at 10 min). In contrast, no effect was observed in B cells, or in BMDC (FIG. 4B). B cells and BMDC may not be sensitive to soluble TRANCE at the concentration used in this assay due to the lack of an adequate number of cell surface receptors. Another possibility is that only certain cell types express JNK-activating signal transducing molecules. These results suggest that the TRANCE recombinant protein is biologically active and appears to stimulate JNK specifically in cells of the T cell lineage.

Described herein is the cloning of a novel member of the TNF cytokine gene family whose expression is restricted to T cells and lymphoid organs and can participate in signaling to T cells implicating TRANCE in the regulation of T cell dependent immune responses. TRANCE was obtained through a genetic screen and it appears associated with cell death and not cell survival or proliferation (FIG. 5B and FIG.

7A, Right). Due to the multi-functional role other TNF-related molecules exhibit it is likely that TRANCE plays a role in cell activation, proliferation, survival or death depending on the context in which it is expressed and the nature of the target cell. In support of this, TRANCE activates JNK, a kinase with pleiotropic biological effects.

Example II

TRANCE, a New TNF SuperFamily Member Predominantly Expressed in T Cells is a Dendritic Cell Specific Survival Factor TRANCE is a new member of the TNF family that is induced upon T cell receptor engagement and activates c-Jun N-terminal kinase (JNK) following interaction with its putative receptor (TRANCE-R) (Wong, et al., *J. Biol. Chem.*, 272;25190-25194). TRANCE expression is restricted to lymphoid organs and to T cells. Disclosed herein is a showing that high levels of TRANCE-R are detected on mature dendritic cells (DC) but not on freshly isolated B cells, T cells or macrophages. Signaling by TRANCE-R appears dependent on TNF receptor-associated factor 2 (TRAF2), since JNK induction is impaired in cells from transgenic mice over expressing a dominant negative TRAF2 protein. TRANCE inhibits apoptosis of mouse bone-marrow derived DC and human monocyte-derived DC in vitro. The resulting increase in DC survival is accompanied by a proportional increase in DC-mediated T cell proliferation in an MLR. TRANCE upregulates $Bcl-x_L$ expression thus enhancing DC survival. TRANCE does not induce the proliferation of B cells or increase the survival of T or B cells. Therefore, TRANCE is a new DC restricted survival factor that mediates T cell-DC communication and provides a tool to modulate DC activity, and hence immune response.

Apoptosis plays a critical role in the development and maintenance of the immune system (35-37). Members of the tumor necrosis factor (TNF) family can regulate apoptosis in addition to an array of other biological effects such as cell proliferation and differentiation (38). Despite the functional redundancy of this family, specificity may be accomplished by coordinating the spatial and temporal expression of TNF-related ligands and their receptors and by restricting the expression of signal transduction molecules to specific cell types. TNF receptors interact with a family of molecules called TRAFs (TNF receptor-associated factors)[1] that act as adaptors for downstream signaling events (39). For example, TRAF2 activates NF-κB (40) and also c-Jun N-terminal kinase (JNK) (41-43). The biochemical events leading to apoptosis involve the caspase family of cysteine proteases (44), whereas NF-κB appears to inhibit cell death (45). The TNF receptor family can also regulate apoptosis by modulating the expression of Bcl-2 and Bcl-2-related proteins (46, 47). Recent data indicates that the Bcl family controls apoptosis by altering transmembrane conductance in mitochondria and by preventing the activation of caspases (48-50).

An important role of TNF members in dendritic cells (DC) biology has recently emerged. DCs have several specializations that lead to the stimulation of naive T cells and play a role in the initiation of the immune response (51). TNF-α and CD40L are molecules involved in the differentiation of DC from $CD34^+$ bone-marrow or cord blood progenitors (52-54). Moreover, CD40L increases DC survival, upregulates MHC and costimulatory molecule expression and induces the expression of a variety of cytokines (e.g., IL-12) in DC (55). Both CD40 and TNFR interact with TRAF2, suggesting that TRAF2 plays a role in DC function.

Recently, TRANCE (TNF-related activation-induced cytokine), a novel ligand of the TNF family was cloned during a search for apoptosis regulatory genes. Remarkably, and unexpectedly, TRANCE expression is restricted to lymphoid specific organs and is selectively expressed in T cells (56). Disclosed herein is the discovery that TRANCE-R signals via TRAF2 in thymocytes and increases DC survival by upregulating $Bcl-x_L$ expression, a property shared with CD40L. However, unlike CD40L, TRANCE selectively acts on mature DC but not on B cells. In addition, high levels of the TRANCE-R are only detected on DC suggesting that a major function of TRANCE in vivo is to modulate DC activity. Hence, TRANCE can also modulate T cell activation and immune response to an antigen.

Materials and Methods

Expression and Purification of Soluble TRANCE. A FLAG epitope-tagged TRANCE molecule (FLAG-TRANCE) was expressed in 293T cells and purified as described (56). To create a human CD8-TRANCE recombinant molecule (hCD8-TRANCE), the extracellular domain of murine TRANCE (a.a. 245-316 of FIG. 4 (SEQ ID NO:4)) was fused to human CD8α (a.a. 1-182) and produced in a baculovirus expression system according to the manufacturer's instructions (BaculoGold, Pharmingen, Dan Diego. CA). hCD8-TRANCE was purified on CNBR-activated Sepharaose gel conjugated to OKT8 following the manufacturer's protocol (Pharmacia Biotech, Piscataway, N.J.). mCD8-CD40L in insect cell culture supernatant was kindly provided by Dr. Randolph J. Noelle (Dartmouth Medical School, Hanover, N.H.).

Mice. C57BL/6 ($H-2^b$) and BALB/c ($H-2^d$) mice were from Taconic Farms (Germantown, N.Y.). Transgenic mice expressing a dominant negative form of TRAF2 (TRAF2.DN) were engineered as described (57).

Cells. Bone-marrow derived DC (BMDC) were generated as described (58) and were used on day 8 of culture. Enriched populations of fresh lymph node or splenic DC were prepared by digesting organs with collagenase then selecting for low density cells via centrifugation on a Nycodenz column (14.5% w/v in PBS+5 mM EDTA; Nycomed, Oslo, Norway) for 15 min. at 4° C. Mature spleen DC were prepared by culturing freshly isolated spleen DC overnight as described (59). The cytokine-induced generation of human DC from PBMCs was performed as described (60). After 2 days in monocyte conditioned medium (MCM), TRANCE or PBS was added to the DCs. Lymph node T cells (99% $CD3^+$ as assessed by flow cytometry) were prepared by magnetic bead depletion (Dynal, Oslo, Norway) of class II, B220, NK1.1, and F4/80 positive cells. B cells were prepared by magnetic depletion of Thy1.2 positive cells (Dynal). Cell viability was assayed by trypan blue exclusion or by propidium iodide uptake.

Flow cytometry. DC phenotype was assessed by flow cytometry as described (61) using the following FITC or PE-conjugated mAbs: $H-2 K^b$, $I-A^b$, ICAM-1, CD11b, CD11c, CD80, CD86, CD25, CD40 (PharMingen). Other mAbs used were biotinylated α-Fas, CD3-FITC, B220-FITC (PharMingen) and NLDC-145-FITC. The expression of TRANCE-R was assessed using the hCD8-TRANCE fusion molecule at 10 μg/mL at 4° C. followed by biotinylated OKT8 mAb and then streptavidin-PE (BioSource International, Camarillo, Calif.). Negative controls were performed by omitting hCD8-TRANCE. For analysis of TRANCE-R expression on resting B cells and fresh DC, low density cells were stained with FITC-B220 or FITC-CD11c, respectively and analyzed on a "FACSCAN" (Becton Dickinson, Mountain View, Calif.).

Mixed leukocyte reaction. BMDC treated for 48 hours in the presence or absence of recombinant TRANCE were cultured with $1 \times 10^5$ purified allogeneic T-cells in flat bottom 96 well plates in a final volume of 200 µl for 3 days and then pulsed for eight hours with 0.5 µCi of $^3$[H]-Thymidine (Dupont NEN®, Boston, Mass.). The cells were then harvested on glass fiber filters and $^3$[H]-Thymidine incorporation was measured using a standard scintillation-detection procedure.

c-Jun N-Terminal Kinase Assays. $2-5\times10^6$ cells from TRAF2.DN transgenic mice or from control littermates were incubated 1-2 hours at 37° C. on plates coated with OKT8 antibody (10 µg/mL). The cells were treated with either soluble TRANCE or an equal volume of PBS before harvesting at the indicated time points and frozen in a dry ice/ethanol bath. JNK was immunoprecipitated with α-JNK1 antibody (Santa Cruz Biotechnology, Santa Cruz, Calif.) and kinase activity assessed as described (56).

Western and RT-PCR analysis of Bcl-$x_L$ and Bcl-2. BMDC ($8\times10^6$/well) were cultured in RPMI in six well plates and treated with PBS, FLAG-TRANCE (1 µg/mL) or soluble CD40L for 0 or 24 hours. The cells were lysed, and 50 µg of protein from each sample were resolved on a 12% SDS-PAGE gel and transferred to Immobilon-P membranes (Millipore, Bedford, Mass.). The blots were blocked in 5% skim milk, probed with α-Bcl-2 (4C11) or α-Bcl-$x_L$ (236) [Kindly provided by Dr. Gabriel Nunez, Univ. of Michigan] and detected with the appropriate HRP-conjugated secondary antibodies and enhanced chemiluminesence substrate (ECL, Amersham Corp., Arlington Heights, Ill.). For RT-PCR analysis of bcl-$x_L$ mRNA expression, BMDC ($2\times10^6$ cells/well) were cultured in 24 well plates, treated with the appropriate reagents and quickly frozen in a cry ice/ethanol bath at the various time points. Total RNA was extracted (RNEasy, Qiagen Inc., Chatsworth, Calif.) and cDNA was diluted to allow PCR amplification to occur as a linear function of starting concentrations. PCR was performed using the conditions and primers as described (47).

Results and Discussion

TRANCE-R is expressed at high levels in dendritic cells. To identify cells that express TRANCE-R, hCD8-TRANCE was used as a molecular probe for FACS analysis.

TRANCE-R was detected on mature BMDC, freshly isolated lymph node DC and freshly isolated spleen DC (FIG. 5). TRANCE-R was greatly upregulated upon the maturation of spleen DC induced by overnight culture. No expression could be detected on freshly isolated lymph node B cells, lymph node T cells, thymocytes or peritoneal macrophages. Therefore, the highest levels of TRANCE-R expression are found on mature DC and suggest that the major role of TRANCE is restricted to DCs.

Figure 10:
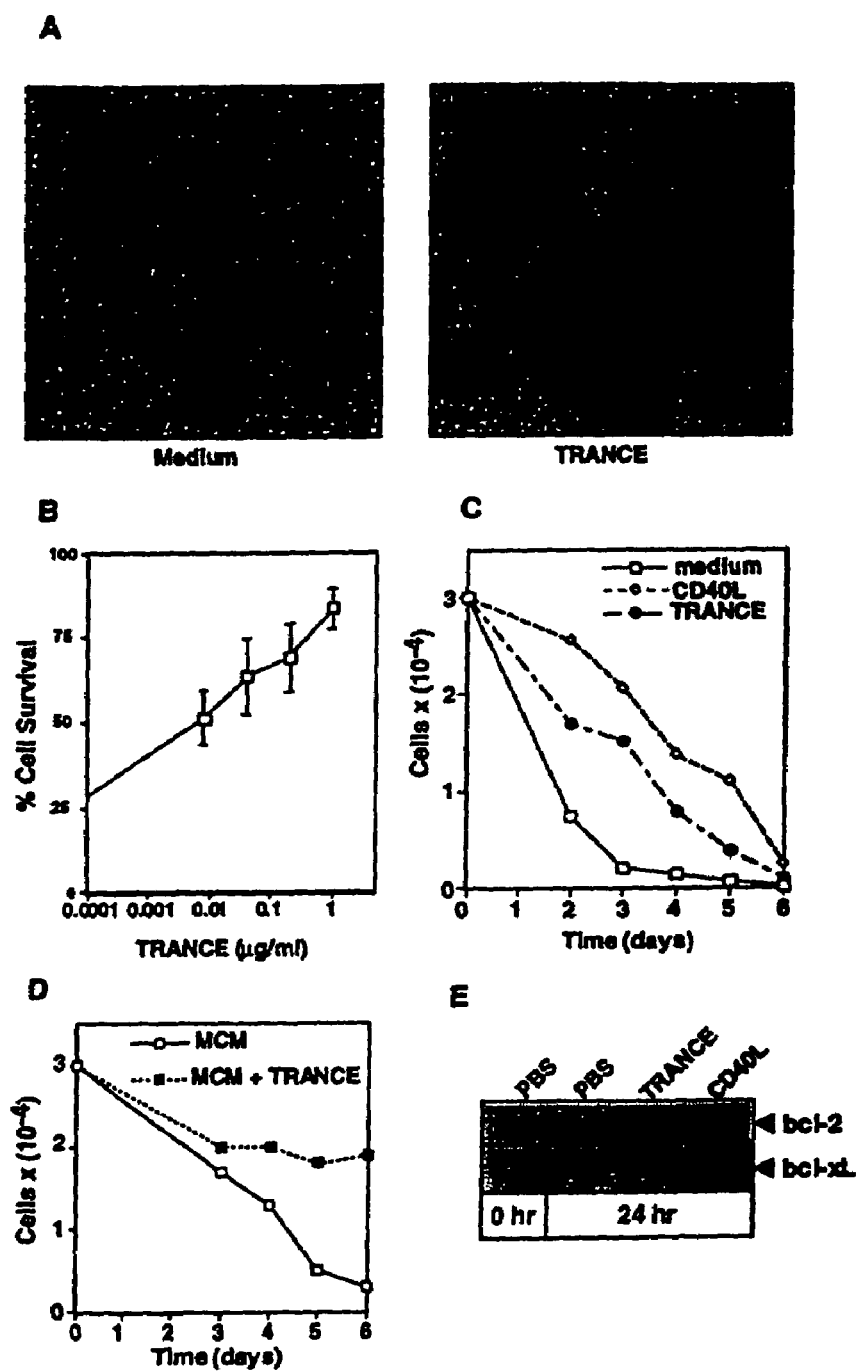
FIG. 10. TRANCE is a DC survival factor that upregulates Bcl-$x_L$.

TRANCE is a dendritic cell survival factor. The biological effects of TRANCE were further studied on mature DCs. TRANCE-treated DCs formed densely packed clusters while control, untreated cells exhibited relatively sparse aggregates (FIG. 10A). In addition, mature BMDC treated with FLAG-TRANCE were significantly protected from spontaneous cell death compared to untreated cells. This effect was dependent on the dose of TRANCE (FIG. 10B). hCD8-TRANCE elicited similar results. This effect was not due to increased cell proliferation since the total number of cells remained the same over time. TRANCE significantly prevented DC cell death until day 6, whereas untreated cells were almost completely dead by day 3 (FIG. 10C). A similar effect on DC survival was observed with human monocyte-derived DC (FIG. 10D). Confirming previous data CD40 ligand (CD40L) also induced the clustering of DC (62, 63) and enhanced DC survival comparably to TRANCE (FIG. 10C).

CD40L upregulates the anti-apoptotic molecule, Bcl-$x_L$, in B cells and protects them from Ig-receptor mediated cell death (47). In addition, CD40L upregulates Bcl-2 in human DC derived from CD34$^+$ progenitor cells, a phenomenon which was correlated with a resistance to Fas mediated apoptosis (46). To determine whether TRANCE can influence Bcl-2 or Bcl-$x_L$ their expression in DC stimulated with TRANCE or CD40L was measured by Western analysis. BMDC expressed relatively high levels of Bcl-2 and relatively low levels of Bcl-$x_L$ after reaching maturity in GM-CSF (FIG. 10E, 0 hr). FLAG-TRANCE and CD40L stimulation lead to increased Bcl-$x_L$ expression by 24 hours. Bcl-$x_L$ expression was nearly absent in cells treated with medium alone bcl-$x_L$ mRNA was upregulated in TRANCE-treated DCs suggesting a transcriptional as opposed to post-transcriptional regulation. In contrast Bcl-2 levels were decreased in both the TRANCE-treated and untreated cells (FIG. 10E). These results suggest that TRANCE, in addition to CD40L, upregulates Bcl-$x_L$ in DC which enhances their viability in vitro.

Figure 11:
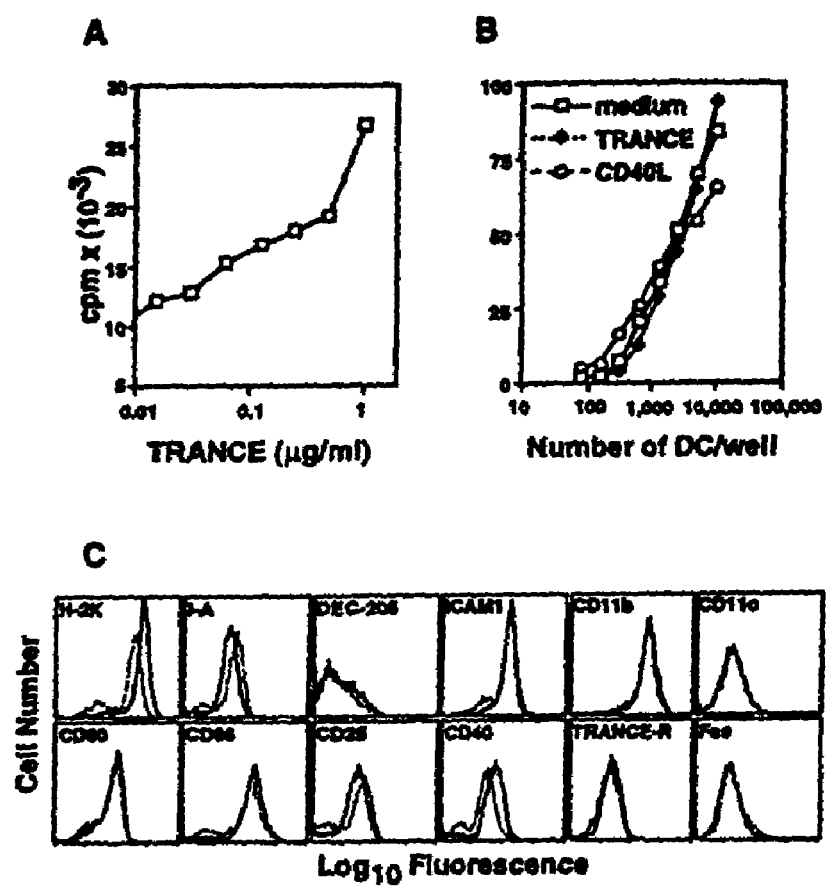
FIG. 11. Cell surface marker expression and T cell stimulatory function of TRANCE treated BMDC.

TRANCE enhances DC-mediated T cell proliferation. To examine the functional consequences of TRANCE on DCs the MLR stimulating ability of DC treated with TRANCE was measured. Increasing doses of FLAG-TRANCE enhanced DC survival at 48 hours which, in turn, led to a proportional increase in the stimulation of T cell proliferation (FIG. 11A). When equivalent numbers of viable TRANCE-treated or untreated DC were used in an MLR, there were no differences in T cell proliferation, suggesting that changes in the expression of costimulatory and antigen presenting molecules did not account for the enhanced T cell proliferation (FIG. 11B). To verify this, the levels of several surface markers were tested by FACS to evaluate any TRANCE-mediated changes to the DC phenotype. There was a slight but reproducible downregulation of MHC II expression and a slight upregulation of MHC I expression (FIG. 11C). There were no TRANCE-mediated perturbations in the expression of the costimulatory molecules CD80 (B7-1) or CD86 (B7-2), and no changes in the expression of the adhesion molecules ICAM1, CD11b and CD11c. Interestingly, CD40 expression increased but Fas or TRANCE-R did not. In sum, TRANCE enhances DC mediated T cell proliferation by increasing the survival of DCs.

Figure 12:
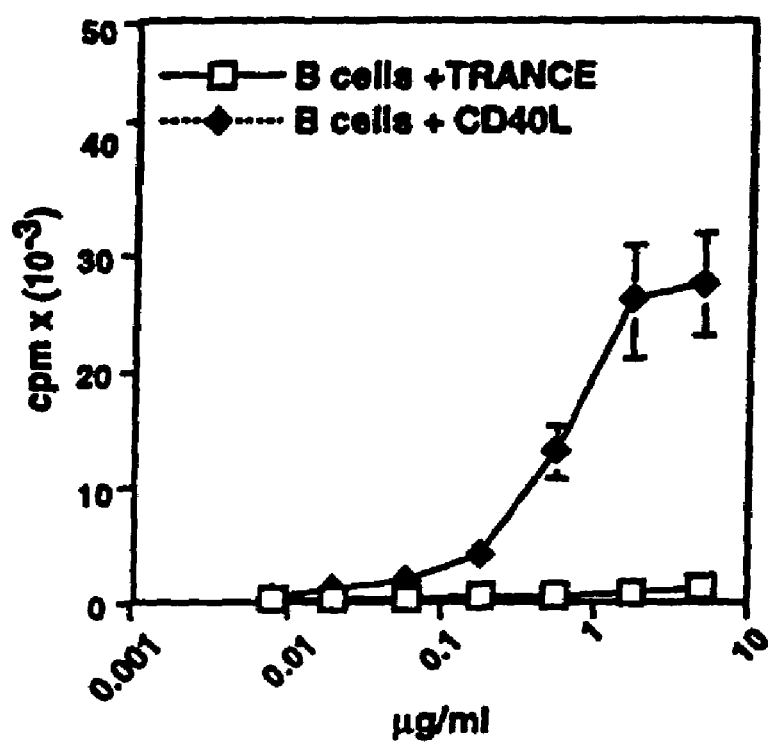
FIG. 12. TRANCE does not induce the proliferation of B Cells. Triplicate wells of 2×10$^4$ purified B cells were cultured in complete medium in the presence of increasing doses of soluble TRANCE or CD40L in flat-bottom 96 well plates. $^3$[H]-Thymidine incorporation was assessed after 2 days of culture.
Figure 13:
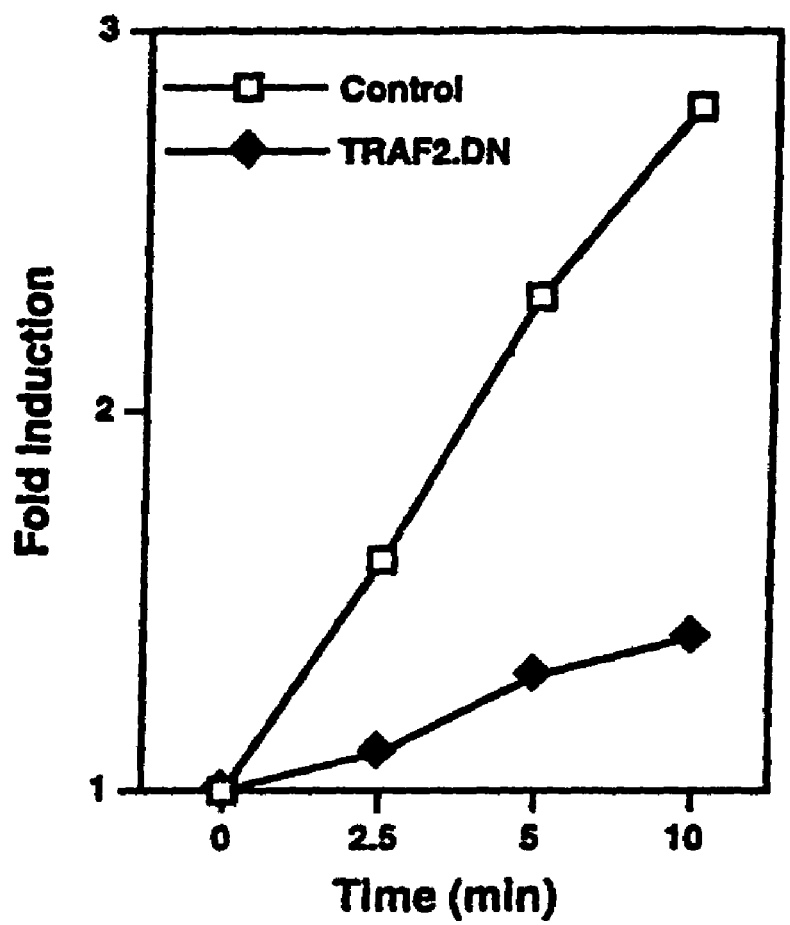
FIG. 13. TRANCE-R signaling is dependent on TRAF2. Thymocytes from transgenic ice expressing TRAF2.DN or control litter mates were stimulated with hCD8-TRANCE (1 μg/mL) on OKT8 (10 μg/mL) coated plates for the indicated amount of time then assayed for JNK activity. The degree JNK activation was analyzed on a phosphorimager (Molecular Imager System, Bio-Rad Laboratories, Hercules, Calif.) and plotted as fold induction over time 0. Representative results of three independent experiments are shown.

TRANCE does not affect B cell proliferation. Expression of high levels of the TRANCE-R appeared restricted to DC by FACS analysis. However, it was found that TRANCE could activate JNK in thymocytes (56) suggesting that FACS analysis might lack the sensitivity to detect low levels of receptor. To further examine the specificity of TRANCE for DCs, its ability to induce B cell proliferation or survival was tested, two functions mediated by CD40L. Recombinant hCD8-TRANCE, tested for its anti-apoptotic function in BMDC, could not stimulate B cell proliferation (FIG. 12) nor could it activate JNK activation (56). In contrast, CD40L efficiently stimulated B cell proliferation in a dose dependent manner (FIG. 13). Finally, TRANCE could not prevent the spontaneous apoptosis of B cells and T cells as assessed by propidium iodide uptake. Therefore, functionally, TRANCE appears to exhibit different cellular specificities and functions when compared to CD40L.

Figure 9:
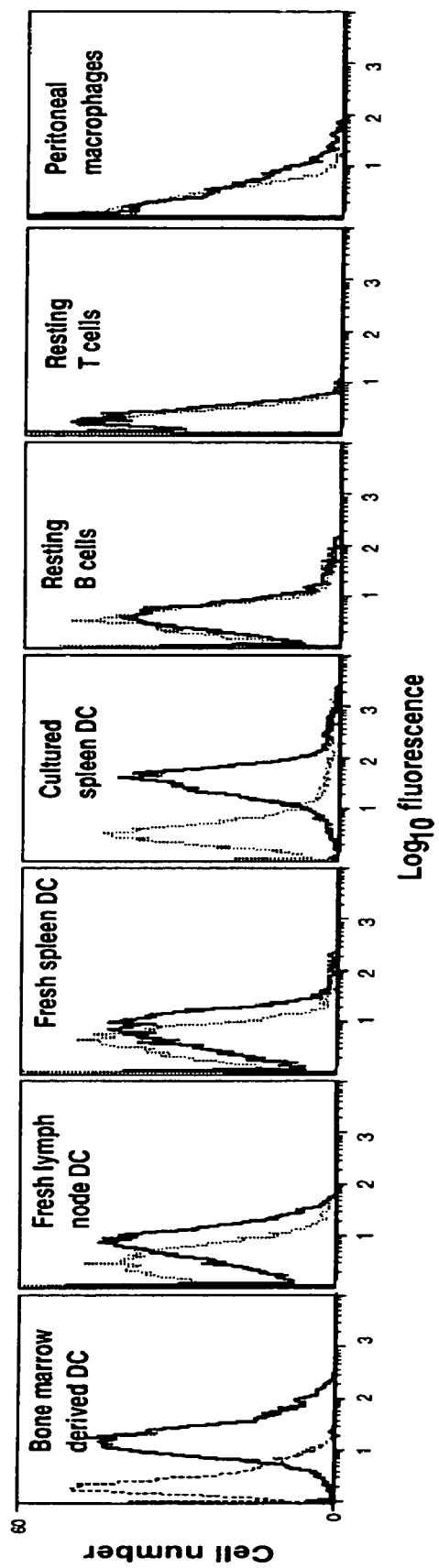
FIG. 9. TRANCE-R expression in various cell-types. Cells were prepared as described in the Materials and Methods section of Example II, infra., and stained with 10 μm of the hCD8-TRANCE recombinant protein (solid lines) or with secondary reagents alone (dotted line). Only viable cells as determined by PI exclusion were gated and analyzed for TRANCE-R expression. Fresh DC were analyzed by two-color staining after gating on CD11c$^{high}$ cells. Each staining was reproduced at least twice.

TRANCE-mediated JNK induction requires functional TRAF2. Recruitment of TRAF2 to the TNFR complex or the CD40 receptor complex is necessary for JNK activation (41-43, 57). To test the possibility that TRANCE-R also signals via TRAF2, TRANCE-mediated JNK activation was analyzed in thymocytes from transgenic mice over expressing a dominant negative form of TRAF2 (TRAF2.DN) (57). JNK activity peaked 2.5 fold over unstimulated cells at 5 minutes in control littermates whereas JNK induction was significantly reduced in TRAF2.DN thymocytes (FIG. 9). These results suggest that signaling from the TRANCE-R requires TRAF2. TRANCE-mediated JNK induction in DC could not be assayed since TRAF2.DN expression has been restricted to lymphocytes in the TRAF2.DN transgenic mice. In addition, JNK activity was constitutively high in mature DC (56), which are also known to have high levels of activated NF-κB (64), thus confounding detection of increased JNK activity.

It has been demonstrated that TRANCE, in addition to CD40L, is a modulator of DC function. Similar to CD40L, TRANCE modulates the survival of mature DC by regulating the expression of Bcl-$x_L$. In contrast to CD40L, however, TRANCE does not act on other APC such as B cells. The signal transduction pathways downstream of TRANCE-R that regulate DC activities remain unknown. TRANCE appears to signal via TRAF2, at least in thymocytes, suggesting that TRAF2 may play a critical role in mediating signals for differentiation, activation and survival in DC.

These findings complement the description of the selective expression of this new TNF family member in T cells. The high level of expression of TRANCE-R on DC suggests a specific role for TRANCE in T cell-DC communication during the primary immune response. Rapid upregulation of TRANCE upon TCR engagement on T cells (56) could specifically enhance the survival of DC during antigen presentation. Both antigen-specific T cells and the antigen presenting DC would therefore depend on each other for activation and survival, respectively. Mature DC which fail to present antigen to T cells would not receive T cell help and thereby die of neglect. This T cell-DC interaction is likely to occur in the T cell area of lymphoid organs which contain DC of mature phenotypes (65). DC can only be detected in afferent lymph not efferent lymph suggesting that DCs are destined to die when they migrate to the lymph node. Thus, TRANCE is important to maintain DC survival. Furthermore, DC pulsed ex vivo with an antigen and TRANCE, and then reintroduced into an animal can be used to induce immunity to tumor or viral antigens in vivo (66). Consequently, TRANCE is a tool to specifically enhance DC function by enhancing their survival in vivo.

Example III

Methods for Modulating Immune Response to an Antigen in an Animal

Dendritic cells are a specialized class of leukocytes found in many tissues and most abundantly in the T-dependent areas of lymphoid organs. As explained above, they play a fundamental role in antigen presentation to T-cells, being very potent since only small numbers of dendritic cells are sufficient to induce T-cell responses. Dendritic cells can prime naive T-cells (CD4 and CD8) both in vitro and in vivo. The antigen presenting function of dendritic cells is related to their high expression of both class I and class II MHC products, as well as different costimulatory and adhesion molecules. Moreover, dendritic cells have special antigen handling mechanisms, including the lectin-type DEC-205 in mice and the mannose receptor in human and abundant MHC class II rich vacuoles. Mature dendritic cells are short-lived in vitro. Different TNF family members appear to promote dendritic cell survival. This is the case for CD40L, TNFα and more recently TRANCE, all products of activated T-cells. However, heretofore, the effect of increasing dendritic survival on in vivo immune response is not known. Set forth herein are experiments designed to determine the effect of immune response to an antigen in vivo wherein dendritic cells are pulsed ex viva with TRANCE, conservative variants or fragments thereof, analogs or derivatives thereof, or fusion proteins comprising TRANCE, conservative variants thereof or fragments thereof, and an antigen, and then are reintroduced into an animal. Also set forth herein are the results of such experiments.

Methods

Animals: C57BL/6 (H-$2^b$) female mice 6-8 weeks old were used in this study and were from Taconic Farms (Germantown, N.Y.).

Dendritic cells: Bone marrow derived dendritic cells were prepared as previously described by Inaba et al. On day 6 of culture immature dendritic cells were pulsed for 6 hours with Purified Protein Derivative (PPD) of Mycobacterium Tuberculosa at 10 mg/ml and the replated in 100 mm culture dishes in order to induce maturation. On day 7 dendritic cells were pulsed with fusion protein mTRANCE-hCD8 (1 mg/ml) or an equivalent volume of PBS. On day 8 mature dendritic cells were washed 4 times in Hank's buffer and resuspended at $4 \times 10^6$/ml in the same buffer.

Priming with antigen-pulsed Dendritic Cells: $2 \times 10^5$ (50 µl) dendritic cells were injected in the hind foot pad of C57Bl/6 mice.

Proliferation assays: Draining lymph nodes (popliteal, inguinal), mesenteric lymph node, and spleen were harvested from immunized mice and cell suspensions were prepared. Cells were cultured in flat-bottomed 96-well plated, $3 \times 10^5$ cells/well in 200 µl in the presence of increasing amount of PPD. Culture medium consisted of Click's medium supplemented with 0.5% heat inactivated normal mouse serum, 10 mM Hepes, 2 mM L-glutamine, 100 U/ml penicillin, 0.1 mg/ml streptomycin and $5 \times 10^{-5}$ M 2-ME. On day 3, cells were pulsed for eight hours with 0.5 µCi of $^3$[H]-Thymidine, then harvested on glass fiber filters and $^3$[H]-Thymidine incorporation was measured using a standard scintillation-detection procedure.

Results

Figure 14:
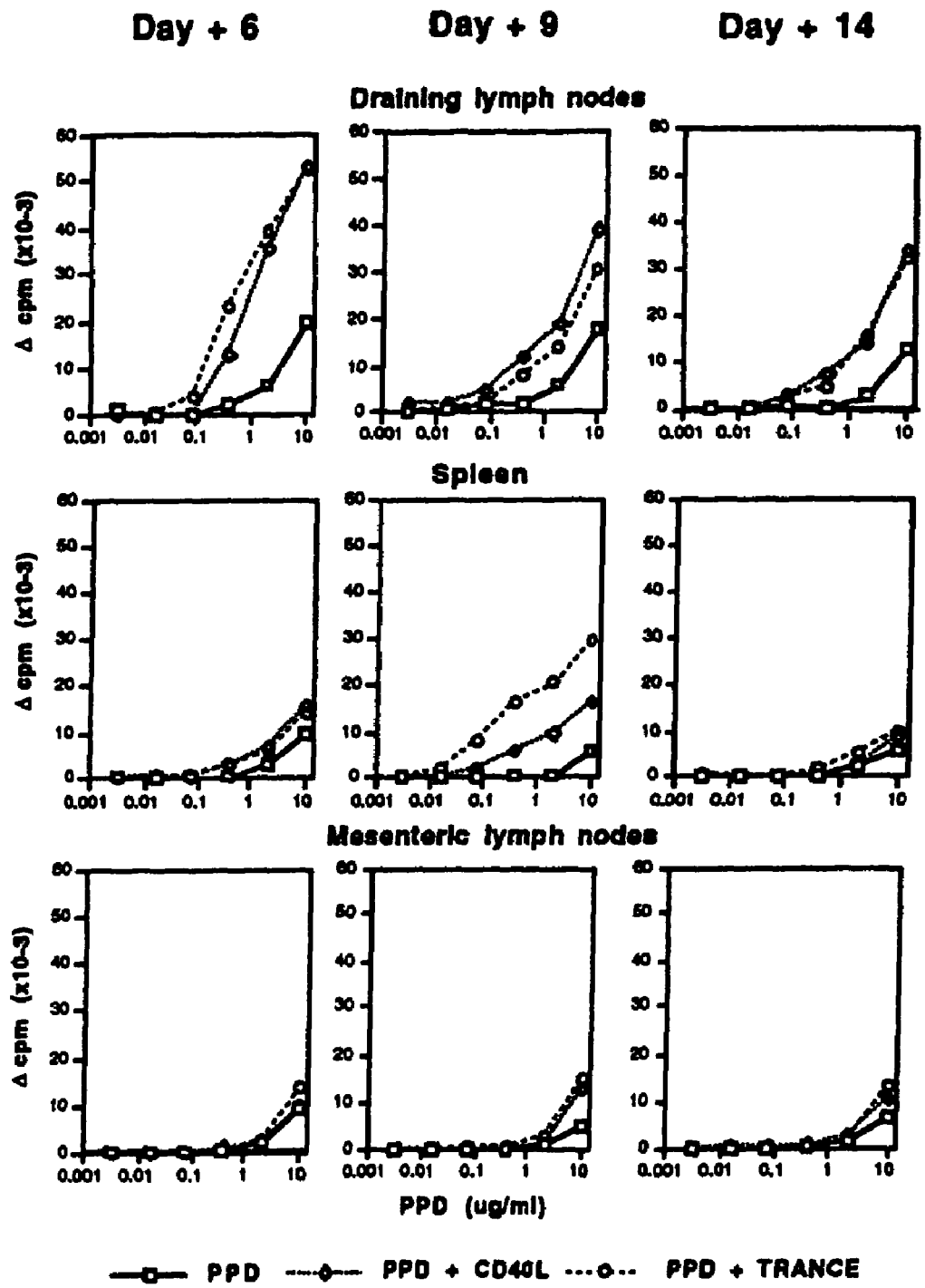
FIG. 14. Proliferative response of T cells to the antigen PPD taken from the Draining Lymph nodes, the Mesenteric Lymph nodes, and the Spleen. Immature BMDC were pulsed on day 6 for 6 hr with 10 μg/ml PPD and then replated in 100 mm dishes to induce maturation. On day 7, DC are further cultured for 24 hr in the absence or the presence of TRANCE-hCD8 (1 μg/ml) or CD40L (1/1000 viral sup). Cells were then extensively washed, counted, and resuspended in PBS. 200,000 cells in 50 μl PBS were then injected in left hind footpad of syngeneic female mice. On day 6, 9 and 14, draining LN (popliteal+inguinal), spleen and mesenteric LN cells were restimulated in vitro with PPD and proliferation was assessed after 3 days of culture. Each point represents the mean of 3 mice.
Figure 15:
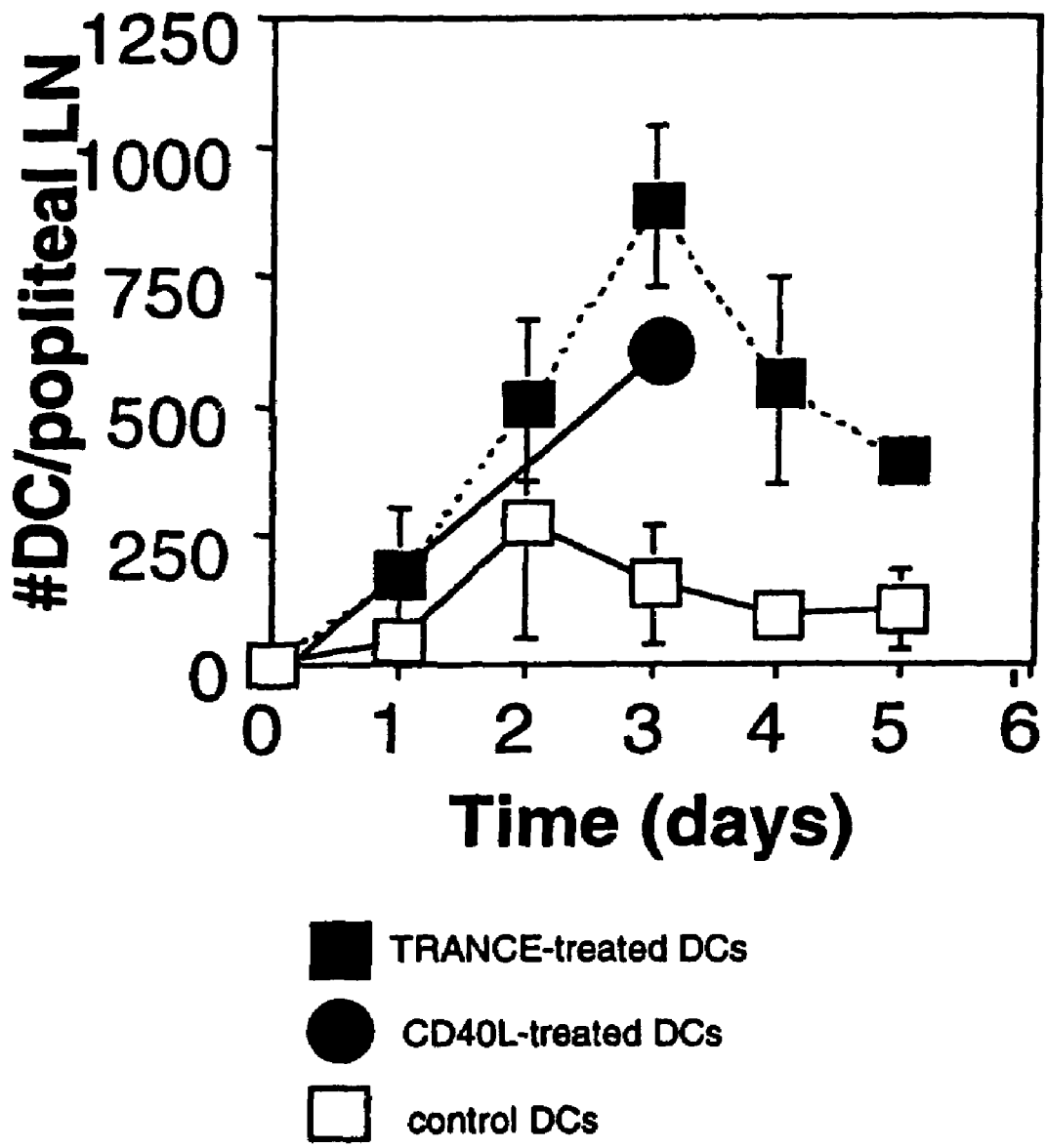
FIG. 15. TRANCE enhances recovering of migrating DCs in the lymph node draining site of injection. Unpulsed and TRANCE or CD40L-pulsed, mature, bone marrow derived DCs were labeled mice. Popliteal LNs were harvested daily and digested with collagenase. The LN cells were counted, stained with PE-conjugated CD11c, and analyzed on a FACScan. The absolute number of injected DCs in each draining LN (CD11c+ve and FL-1 high) was calculated. Each point represents the mean±SD of three mice in each group and at each point. Similar results were obtained in three experiments.

As shown in FIG. 14, the proliferative response to PPD is surprisingly 5-8 times higher in draining lymph nodes of mice which have received PPD+TRANCE pulsed dendritic cells, than of mice which have received PPD-pulsed dendritic cells. Similar enhancement was achieved when DCs were treated with agonistic CD40L. The major difference was on day 6, which has been shown to correspond to the peak of proliferative response after priming with ex vivo antigen pulsed dendritic cells. However, a significant increase in in vitro response to PPD was still observed 2 weeks after the injection, which indicates the secondary response is also increased. As expected, no significant proliferative response was observed in mesenteric lymph node. A significant response to PPD was observed in spleen of injected with PPD-+ TRANCE pulsed dendritic cells, but not with PPD-pulsed dendritic cells. Although Applicants are under no obligation to explain such results, and do not intend to be bound by such an explanation, Applicants have postulated that this result is related to the recirculation of PPD-specific memory T-cells through the spleen at that time.

As shown in FIG. 14, treatment of DCs ex vivo with TRANCE or CD40L enhances the longevity of DCs in vivo as well as in vitro, which leads to the enhanced immunogenicity of antigens (e.g., PPD) delivered by the treated DCs.

CONCLUSION

Increasing survival of dendritic cells ex vivo before injection by pulsing them with TRANCE, conservative variants thereof, fragments thereof, analogs or derivatives thereof, or fusion proteins comprising TRANCE, conservative variants thereof, or fragments thereof can dramatically improve the adjuvant effect of dendritic cells in vivo regarding a particular antigen, which was also used to pulse the dendritic cells were ex vivo. In addition to the survival effect of TRANCE on the dendritic cells, ex vivo exposure of the cells to TRANCE also stimulates their production of cytokines, such as IL-12, for example. Hence, dendritic cells treated in accordance with the method of the invention can be used as "natural adjuvant" in vivo for inducing efficient immune response to a bacterial, viral or tumor antigen in rodents, e.g., such dendritic cells have applications in humans to induce immune response to viral or tumor antigens. Indeed, large numbers of human dendritic cells can now be generated from peripheral blood or bone marrow progenitors using cytokines cocktails. Furthermore, fragments of TRANCE, conserved variants thereof, and even fusion proteins comprising TRANCE, such as mTRANCE-hCD8 described herein, increase in vitro survival of monocyte-derived human dendritic cells. As result, TRANCE or CD40L have applications in immunotherapy as a specific tool to increase in vivo dendritic survival in humans.

Example IV

The TNF-SuperFamily Member TRANCE is Differentially Expressed on T Cell Subsets and Induces Cytokine Production in Dendritic Cells As explained in the above Examples, TNF and TNF receptor family of proteins play critical roles in the initiation and regulation of the immune response. These proteins enable complex dialogue to occur between cells within the immune system and with cells of other tissues. Despite the apparent redundancy of the TNF/TNFR family as evidenced by the continually growing number of discovered ligand/receptor pairs and by the common signaling transducers utilized by the receptors, the specific function of members of this family clearly exists as shown by gene-knockout studies, in which the deletion of one family member cannot by fully compensated by the others. Specificity may be achieved by restricting their expression to particular cells and/or by linking their signal transducing effectors to cell-specific signaling pathways.

T-cells can modulate the function of dendritic cells (DC), antigen-presenting cells specialized in the activation of naive T-cells (67), via TNF-related molecules. CD40L, a CD4$^+$ T-cell restricted molecule, has been shown to induce differentiation, cytokine production (TNF-α, IL-8, IL-12 and MIPα) and protection from spontaneous apoptosis in DC. TNF was also shown to enhance dendritic cell survival in vitro (63). IL-12-producing DC were shown to skew the response of T-cells towards the Th1 phenotype (70, 71) suggesting that CD4$^+$ T-cells express CD40L to adjust the type of response (Th1 vs. Th2) by controlling DC function.

Further, Applicants have discovered and set forth in the above Examples that unexpectedly, TRANCE (TNF-related activation induced cytokine), a member of the TNF family (56) also called RANK-L (Receptor activating NF-kB-ligand (72)) is a DC survival factor that regulates the expression of the anti-apoptotic molecule, Bcl-$x_L$ (73). TRANCE expression appears restricted to T-cells whereas high levels of TRANCE-R are expressed on mature DC. Hence, TRANCE/TRANCE-R interactions are involved with T-cell-DC communication (56, 72, 73). Furthermore, Applicants have discovered that TRANCE expression has also been detected on osteoblasts and was shown to be required for osteoclast differentiation from myeloid progenitors (74, 75). In addition, a soluble decoy receptor (OPG/OCIF) for TRANCE can block TRANCE-mediated osteoclast differentiation, and thus modulate T-cell-DC interactions (76).

Applicants set forth herein the discovery that CD4+ and CD8+ T-cells, when activated through the TCR/CD3 complex, express high level of TRANCE and its expression is strongly enhanced by CD28-mediated costimulation on CD4+ T-cells. In addition, Applicants have discovered that TRANCE has no significant effects on activated T and B cells although they can express low level of TRANCE-R when activated. TRANCE can upregulate both proinflammatory cytokines and factors in DCs that mediate T-cell growth and differentiation, a property shared with CD40L. Moreover, Applicants have discovered that, surprisingly and unexpectedly, TRANCE cooperates with a protein of the TNF family, such as CD40L or TNF-α to enhance the survival of DCs. Therefore, TRANCE plays an important role in the regulation of T cell responses by controlling the lymphocyte-stimulatory capacity of DC.

Materials and Methods

Expression and Purification of Soluble TRANCE-R-Fc and hCD8-TRANCE. To create a TRANCE-R-Fc recombinant molecule (TR-Fc), the Fc portion of human IgG1 was fused to the C-terminal end of the extracellular domain of the murine TRANCE-R (also called RANK (11)) and produced in a baculovirus expression system according to the manufacturer's instructions (BaculoGold, Pharmingen, Dan Diego. CA). TR-Fc was purified from the culture supernatants on protein A sepharose bead. (Pharmacia Biotech, Piscataway, N.J.). hCD8-TRANCE was prepared as previously described (73).

Determination of the specificity of hCD8-TRANCE and TR-Fc. 293T cells grown in DMEM 10% FCS were transfected with expression vectors containing mTRANCE cDNA, mTRANCE-R or mFas cDNA by calcium phosphate precipitation. Cells were incubated with 10 mg/ml of hCD8-TRANCE or 5 mg/ml of TR-Fc and binding was revealed by FACS as described below.

Mice. C57BL/6 (H-2b) and BALB/c (H-2$^d$) mice were from Taconic Farms (Germantown, N.Y.).

Medium. The culture medium used was RPMI 1640 supplemented with heat-inactivated 5% FCS, 2 mM L-glutamine, 100 U/ml penicillin, 0.1 mg/ml streptomycin, 10 mM HEPES and 5×10-5 M 2-ME.

Cells. Mature bone-marrow derived DC (BMDC)3 were generated as described and were used on day 8 of culture. Splenic DC were isolated as described (59) and cultured overnight to induce maturation. Lymph node T-cells (≧99% CD3$^+$ as assessed by flow cytometry) were prepared by magnetic bead depletion (Dynal, Oslo, Norway) of class II, B220, NK1.1, and F4/80 positive cells. Th1 and Th2 clones derived from DO11.10 TCR transgenic mice, were tested by intracellular staining of IL-4, IL-10 and IFN-γ. The Th1 clones were IL-4⁻ IL-10⁻ IFNγ⁺ and the Th2 clones were IL-4⁺ IL-10⁺ IFNγ⁻. B cells (≧94% B220⁺) were prepared from spleen cells by magnetic bead depletion of Thy-1.2 positive cells (Dynal). Cell viability was assayed by trypan blue exclusion or by propidium iodide uptake.

Flow cytometry. The expression of TRANCE on activated CD4+ and CD8⁺ T-cells was assessed using the TR-Fc fusion protein at 5 mg/ml followed by FITC-conjugated goat anti-human IgG (Fc specific) F(ab')₂ fragment (Jackson. Laboratories, West Grove, Pa.). The negative control consisted of normal hIgG1 (Sigma, St Louis, Mich.). T-cell and thymocyte subsets were sorted using a FACS "VANTAGE", (Becton Dickinson, Mountain View, Calif.).

RT-PCR analysis. For semi-quantitative PCR analysis total RNA was extracted from FACS sorted T-cell subsets (RNA Isolation Kit, Stratagene, Calif.) cultured in 24 well plates coated with or without anti-CD3 (145-2C11, 10 mg/ml) for 3.5 h and subjected to RT-PCR as previously described (56). HPRT: (sense: 5'-GTA ATG ATC AGT CAA CGG GGG AC-3' (SEQ ID NO:15), antisense: 5'-CCA GCA AGC TTG CAA CCT TAA CCA-3' (SEQ ID NO:16)). TRANCE: (sense: 5'-CCT GAG ACT CCA TGA AAA CGC-3' (SEQ ID NO:11), antisense: 5'-TAA CCC TTA GTT TTC CGT TGC-3' (SEQ ID NO:12)). CD40L: (sense: 5'-GTG GCA ACT GGA CTT CCA GCG-3' (SEQ ID NO:17), antisense: 5'-GCG TTG ACT CGA AGG CTC CCG-3' (SEQ ID NO:18)). The PCR products were analyzed by Southern blot as previously described (56).

Ribonuclease protection assays. Total RNA was obtained from 1×10⁷ BMDC (RNA Isolation Kit; Stratagene, CA) treated for 12 h with hCD8-TRANCE (1-5 mg/ml), a 1:100 dilution of mCD8-CD40L baculoviral supernatants or with an equivalent volume of PBS. 5 mg of RNA from each sample was hybridized to a P³²-labeled antisense RNA probe set (mCK-1, mCK-2, mCK-3, mAPO-2; Pharmingen, Calif.), digested with RNAse+T1 nuclease and the protected probe fragments were resolved on 5% polyacrylamide gels following the manufacturer's protocols. Band intensity was quantified by phosphorimaging (Molecular Imager System; Bio-Rad, Calif.) and normalized to the intensity of the GAPDH probe.

Results

Figure 17:
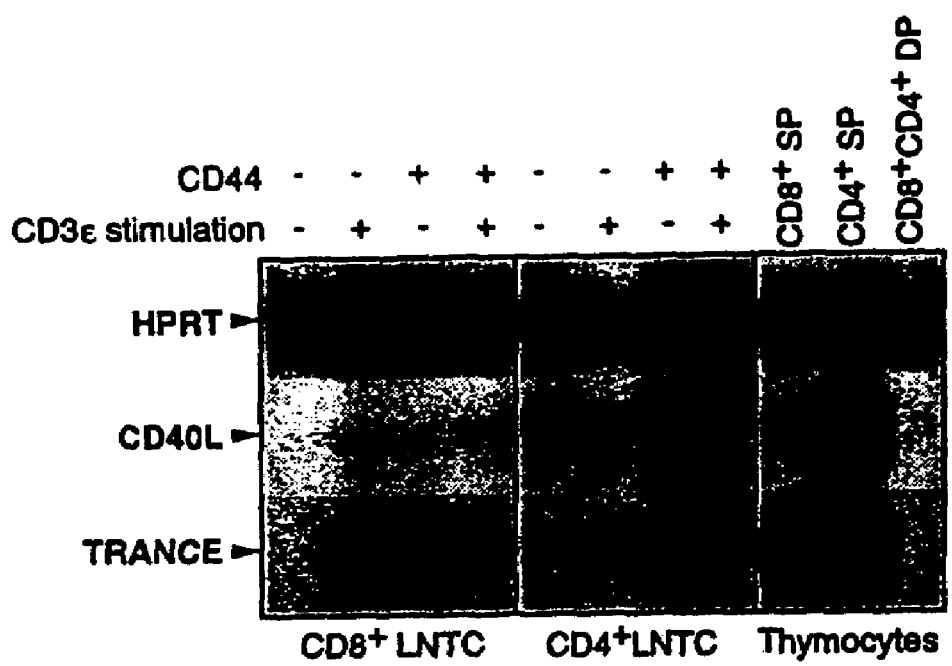
FIG. 17. RT-PCR analysis of TRANCE mRNA expression in thymocytes and peripheral T-cell subsets. Lymph node T-cells (LNTC) were sorted by FACS based on CD4, CD8 or CD44 expression. Naive and memory T cells were identified as CD44$^-$ and CD44$^-$ respectively. Thymocytes were sorted into single positive (SP, CD4$^-$CD8$^-$ and CD4$^-$CD8$^+$) and double positive (DP, CD4$^+$CD8$^+$) populations. The LNTC-sorted populations (1×10$^6$) were stimulated on anti-CD3 mAb coated plates or were left unstimulated for 3.5 h before their RNA was harvested. RT-PCR followed by southern blot analysis with $^{32}$P-labeled cDNA revealed the expression of TRANCE, CD40L and HPRT. HPRT levels normalized the amount of cDNA template used in each PCR reaction.

The regulation of TRANCE mRNA expression in T cells. TRANCE mRNA expression was measured in sorted naive (CD44$^{low}$) and memory (CD44$^{high}$) LN T-cell subsets and in various thymocyte populations (FIG. 17). Purifed T-cells and thymocytes were stimulated with anti-CD3 mAb or left unstimulated for 3.5 hr and levels of TRANCE mRNA were assessed by semi-quantitative RT-PCR analysis (FIG. 17). Resting CD8⁺ and CD4⁺ memory cells expressed high levels of TRANCE whereas resting naive CD8⁺ and CD4⁺ T-cells did not express TRANCE mRNA. Upon CD3-stimulation all T-cell subsets upregulated TRANCE with the highest levels observed in CD3-stimulated memory CD4⁺ and CD8⁺ T-cell subsets. CD40L mRNA expression was also examined and shown to be upregulated in activated CD4⁺ naive and memory T-cells (77). In contrast, CD40L mRNA expression was very weak in CD8⁺ T-cells (FIG. 17).

Although TRANCE was not expressed in resting peripheral T-cells, substantial levels of TRANCE mRNA were detected in SP CD4+ CD8⁻ and CD4⁻CD8⁺ thymocytes. In contrast, CD40L was restricted to CD4⁺CD8⁻ thymocytes (FIG. 17). Hence, TRANCE and CD40L are transiently expressed upon maturation of thymocytes (78).

Figure 18:
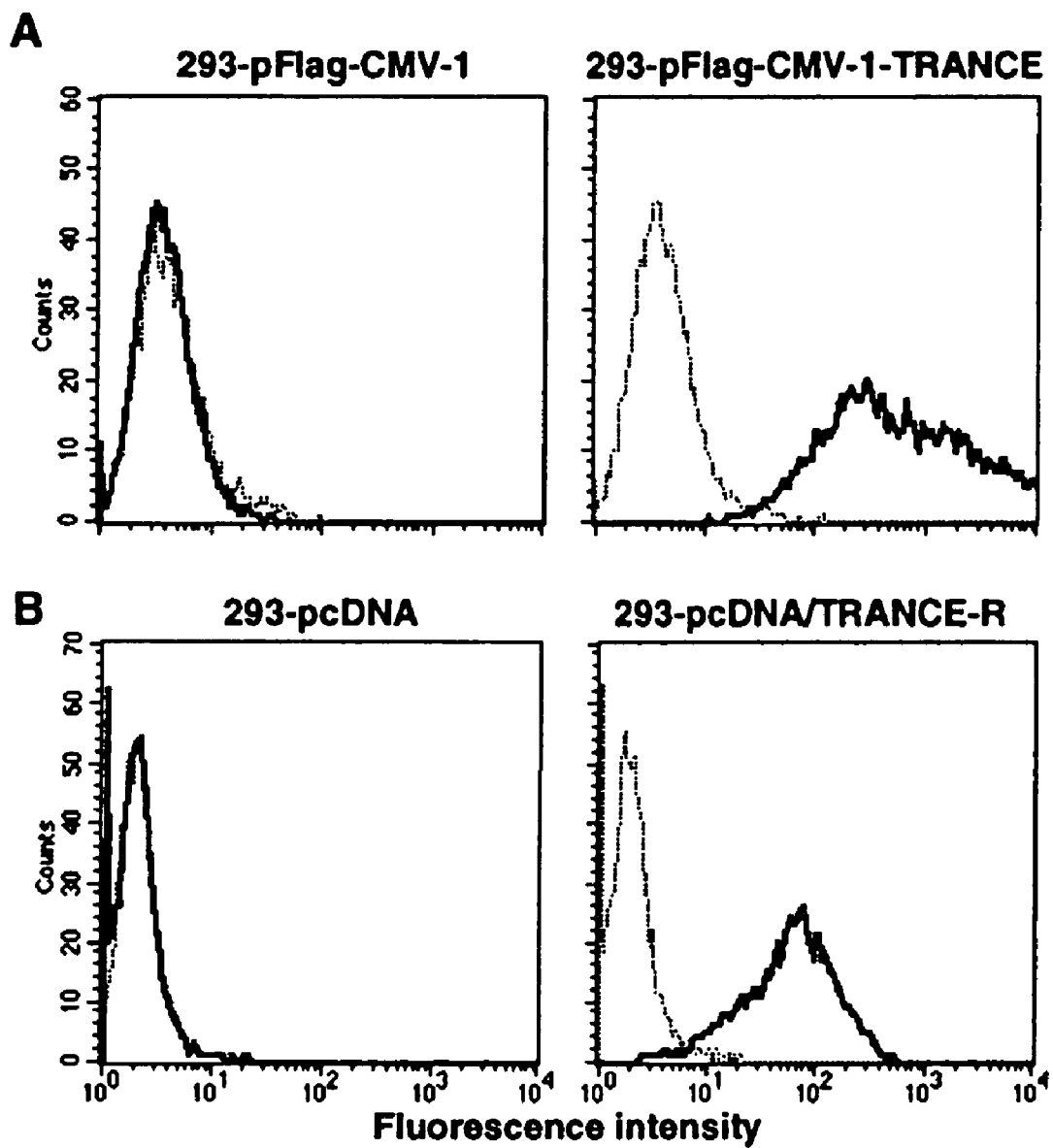
FIG. 18. Specificity of hCD8-mTRANCE and TRANCE-R-Fc fusion molecules 293-T cells transfected with vector alone (pcDNA), vector containing mTRANCE or the extra-cellular domain of TRANCE-R and stable cell lines were cloned by limiting dilution. (A) Cells transfected with pFlag-CMV-1 of pFlag-CMV-1/mTRANCE were incubated with 5 mg/ml of TRANCE.R-Fc (solid line) or normal hIgG1 (dotted line) followed by FITC-conjugated anti-human Fc. (B) Cells transfected with pcDNA or pcDNA/TRANCE-R were incubated with 10 mg/ml hCD8-mTRANCE (solid line) followed by biotinylated anti-human CD8 and St-PE. Negative control cells were incubated with the secondary Ab alone (dotted line). Cells were analyzed on a FACScan.
Figure 19:
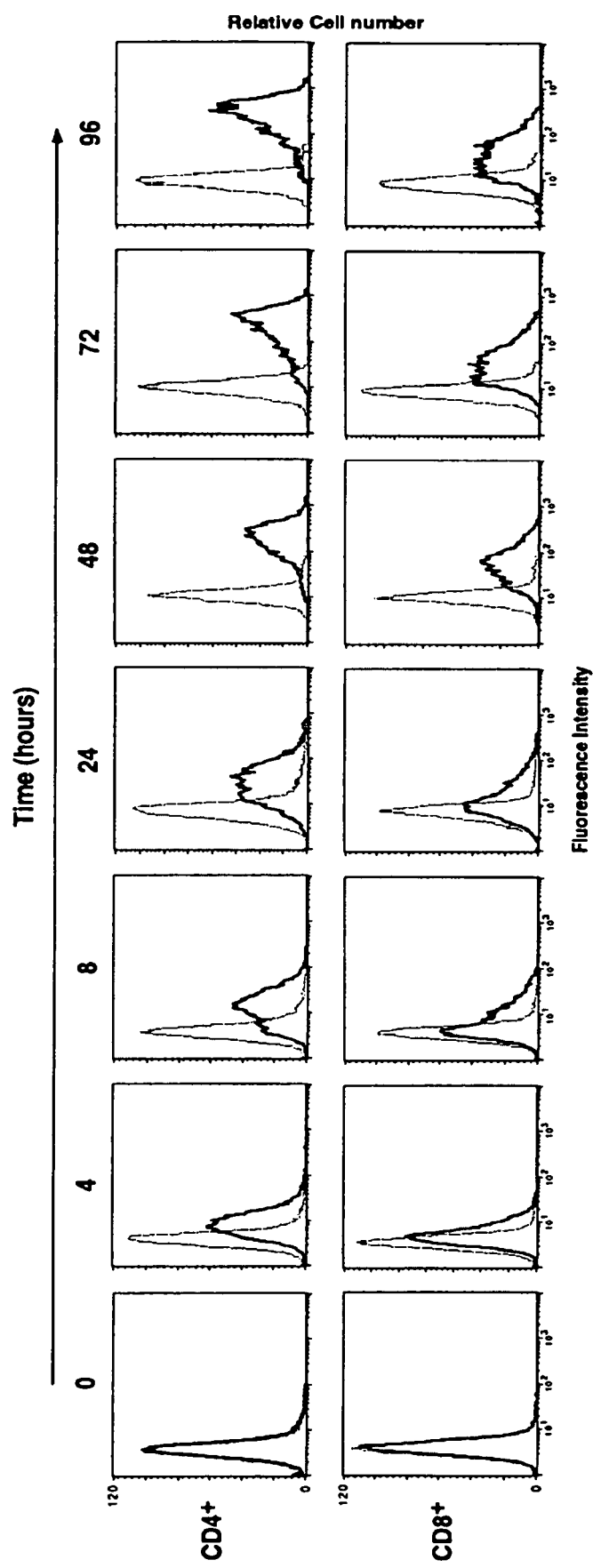
FIG. 19. Kinetics of TRANCE expression on CD4+ and CD8$^-$T-cells activated by anti-CD3 and anti-CD28. Purified lymph node T-cells were cultured in anti-CD3 coated (10 mg/ml) 96-well plates for the indicated amount of time in the presence of 2.5 mg/ml of anti-CD28 mAb. Subsequently, cells were double stained with anti-CD4-PE or CD8-PE, and TR-Fc or control hIgG1 (5 mg/ml) followed by FITC-goat anti human IgG F(ab')2, and binding was analyzed by FACS. Histograms reveal the binding of TR-Fc (solid line) or hIgG1 (dotted line) on CD4$^-$ and CD8$^+$ gated cells. One representative experiment of 4 is shown.
Figure 20:
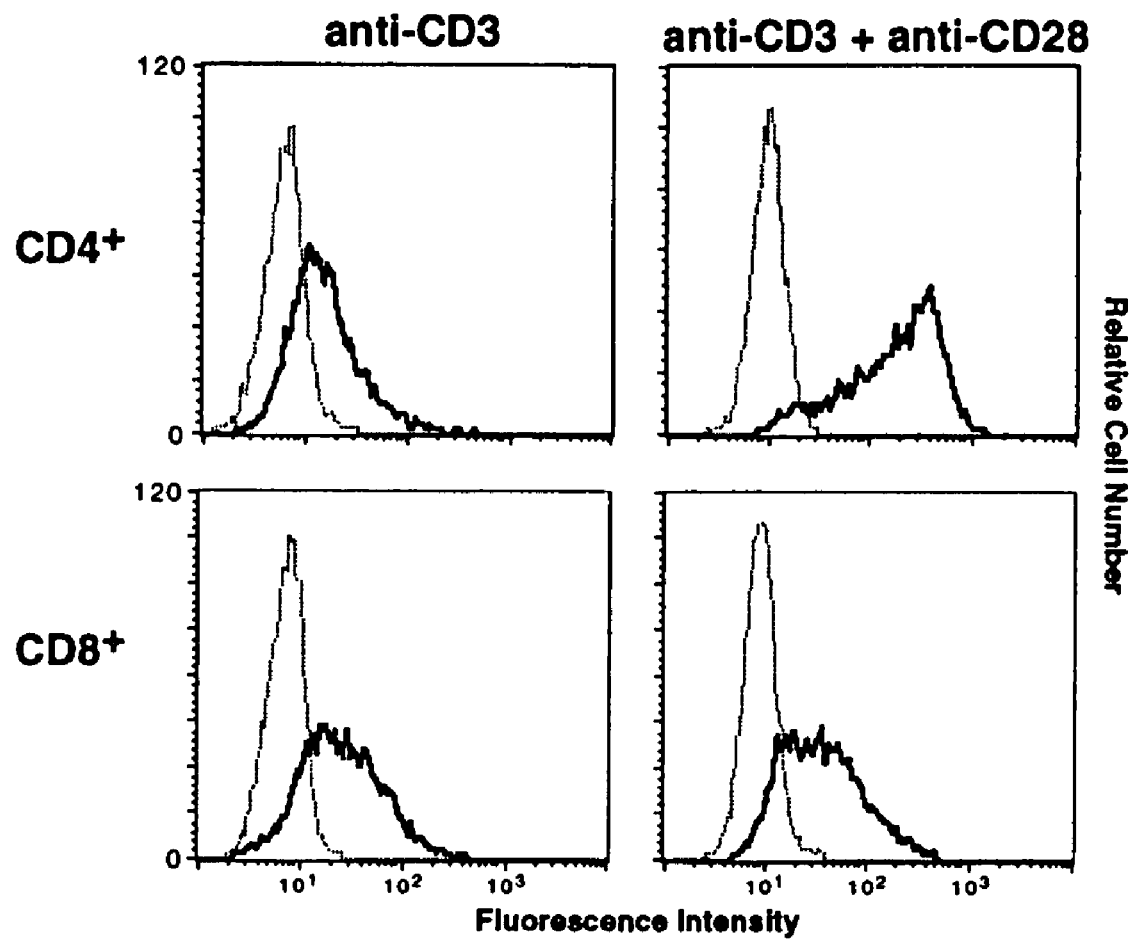
FIG. 20. The effect of CD28 mediated costimulation on TRANCE expression on CD3-activated CD4+ and CD8$^-$ T cells. Purified lymph node T cells were cultured as described in FIG. 19 in the presence or in the absence of anti-CD28 mAb (2.5 mg/ml). TRANCE expression was assessed after 72 h of culture. One representative experiment of 5 is shown.
Figure 21:
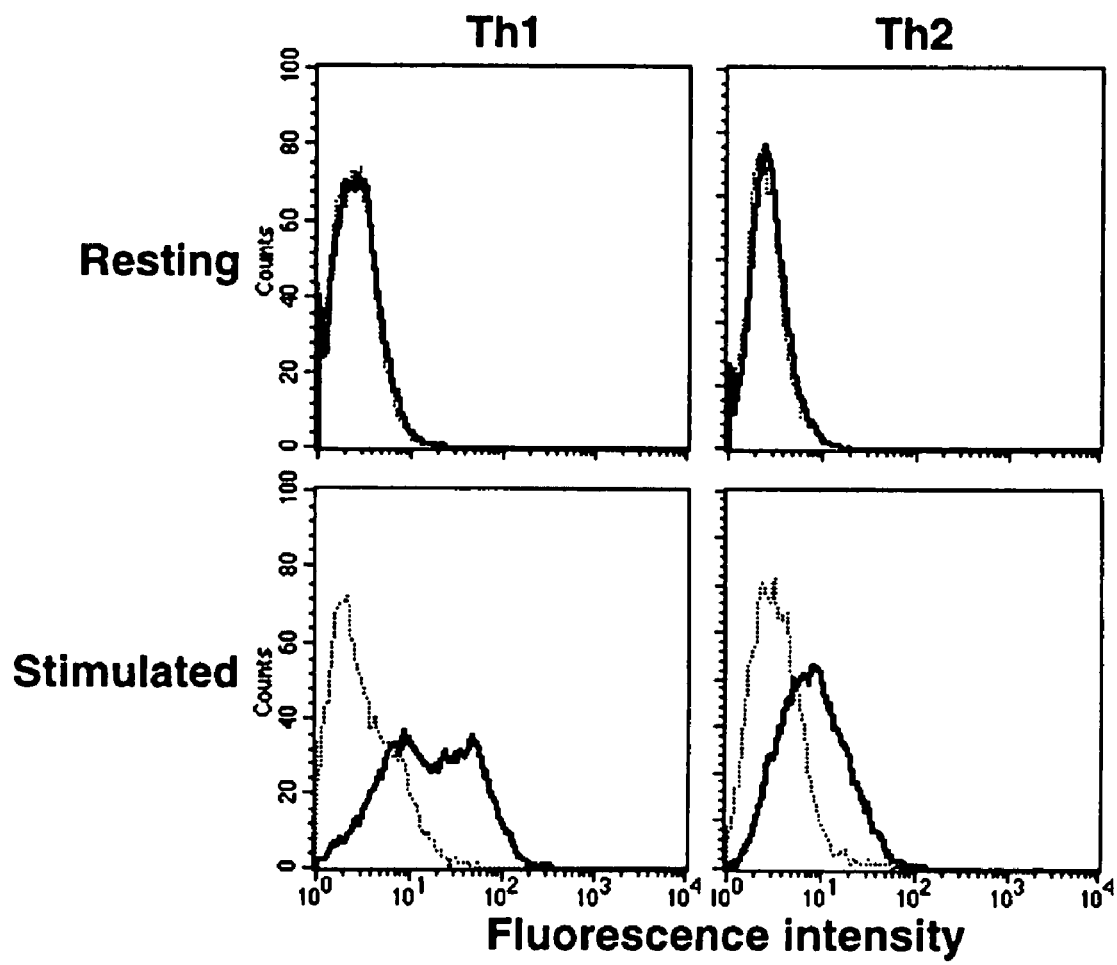
FIG. 21. The expression of TRANCE by Th1 and Th2 clones. Resting or anti-CD3 activated (48 hours) Th1 and Th2 clones derived from DO11.10 transgenic mice were stained with TR.R-Fc as described above. Representative results of two independent experiments are shown.

The regulation of TRANCE protein expression on the surface of T cells. TR-Fc fusion protein that could specifically recognize TRANCE-transfected 293T cells but not 293T cells transfected with vector alone (FIG. 18A) was used to detect surface TRANCE expression on T-cells. TRANCE was not detected on resting CD4+ or CD8⁺ T-cells (FIG. 19). On CD4⁻ T-cells, surface TRANCE expression was detected as soon as 4 h after anti-CD3 and anti-CD28 stimulation, peaked around 48 h and remained high at least until 96 hours (FIG. 19). The kinetics of TRANCE expression on CD8⁺ T-cells were slower than that on CD4⁺ T-cells and CD8⁺ T cells expressed lower levels of TRANCE than CD4⁺ T when stimulated with anti-CD3 and anti-CD28 mAbs (FIGS. 20 and 21). However, CD4⁺ and CD8⁺ T cells stimulated with anti-CD3 in the absence of costimulation expressed similar low levels of TRANCE (FIG. 21). Indeed, anti-CD28 mAb-mediated costimulation greatly enhanced TRANCE expression on CD4⁺ but not significantly on CD8⁺ T cells (FIG. 20). To determine whether TRANCE expression is restricted to T helper subsets, Th1 and Th2 clones derived from DO11.10 TCR transgenic mice were stained with TR-Fc. As shown in FIG. 21, TRANCE was not detected on resting clones but was strongly upregulated on both Th1 and Th2 clones after anti-CD3 stimulation although the Th1 clones consistently expressed higher levels than the Th2 clones.

Figure 22:
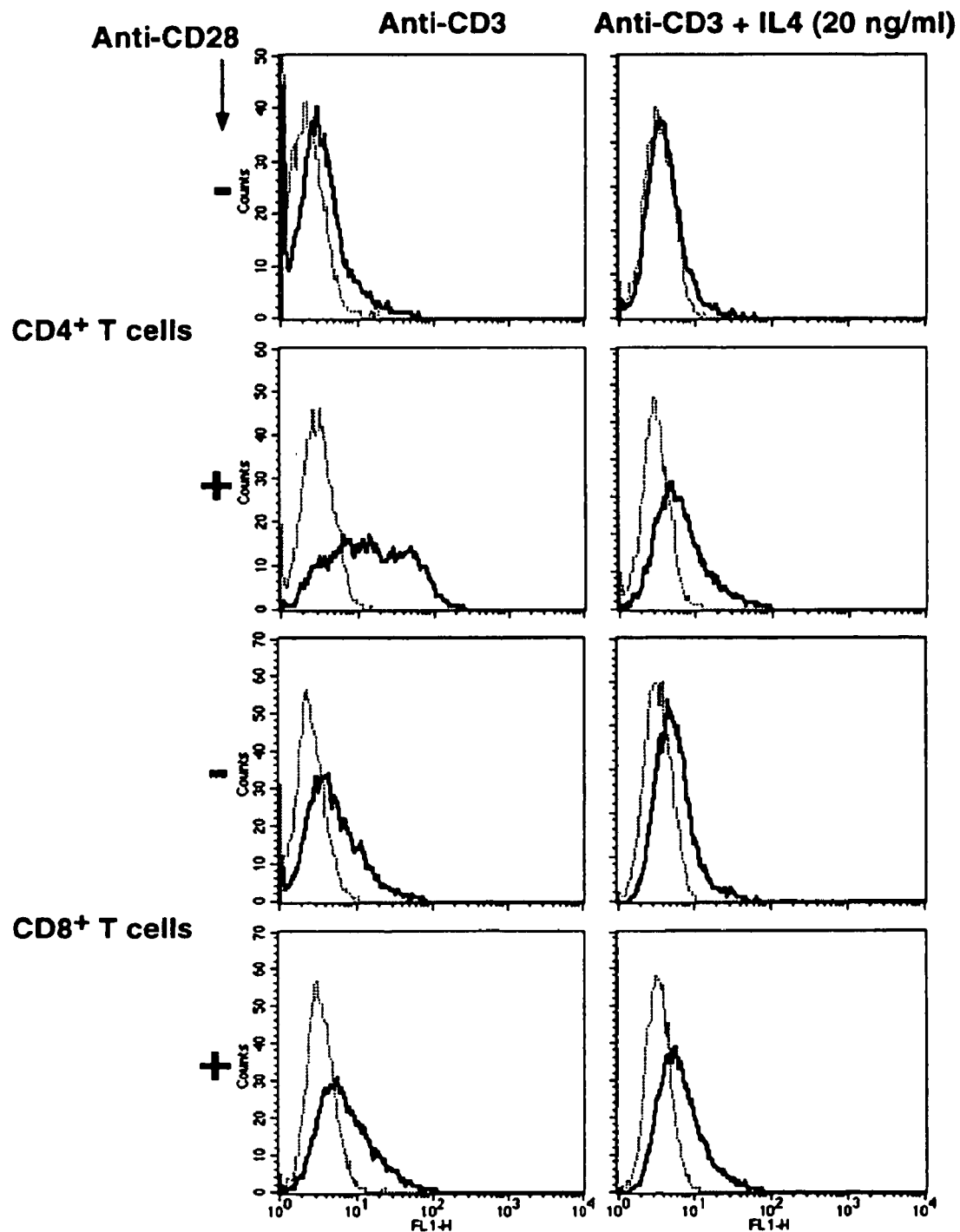
FIG. 22. IL-4 down regulates TRANCE expression on activated CD4− T cells. Purified lymph node T cells were cultured as described above in the presence or the absence of anti-CD28 mAb (2.5 mg/ml) and in the presence or in the absence of murine rIL-4 (20 ng/ml). TRANCE expression was assessed after 72 h of culture. The results of one representative experiment of 4 are shown FIG. 23 Activated T and B cell express low levels of TRANCE-R. (A) Purified lymph node T cells were cultured in anti-CD3 coated (10 mg/ml) 96-well plate in the presence or in the absence of anti-CD28 mAb (2.5 mg/ml), rIL-4 (20 ng/ml) and TGF-b1 (1 ng/ml). TRANCE-R expression was assessed after 60 hours of culture using the hCD8-mTRANCE fusion molecule as described in the Materials and Methods section. TRANCE-R expression was detected only after 48 h of simulation (B) Purified spleen B cells were cultured in 96-well plate in medium alone or in the presence of soluble CD40L (1/100 dilution of insect cell supernatant) or anti-m chain Ab (0.5 mg/ml)+rIL-4 (20 ng/ml). After 48 h of culture cells were stained for CD40, CD95 (Fas), TRANCE-R and B7-2. Maximal levels of expression were detected between 24 and 60 h of stimulation. One representative experiment of 3 is shown FIG. 24. TRANCE induces an array of cytokines in bone-marrow derived dendritic cells (BMDC). (A) RNA was extracted from PBS and hCD8-TRANCE (2.5 mg/ml) treated BMDC and subjected to ribonuclease protection assays as described in the Materials and Methods section to measure levels of IL-1α, IL-1β, IL-1Ra IL-2, IL-4, IL-5, IL-6, IL-9, IL-10, IL-15, IL-1α, MIF, TNF-α, TNF-β (LT-α), LT-β, IFN-γ or IFN-β mRNA. Yeast tRNA controlled for non-specific probe protection.

In order to further analyze the regulation of TRANCE expression on activated T cells, the effects of several cytokines were tested. Purified T cells were stimulated for 60 hours in the presence or in the absence of cytokines. Among the different cytokines tested, it was discovered that IL-4 (20 ng/ml) significantly inhibited the expression of TRANCE on activated CD4+ but not CD8⁺ T cells (FIG. 22). In contrast, TGF-β1 (1 ng/ml), IFN-α (1000 U/ml), IFN-α (100 U/ml), IL-2 (50 U/ml), TNF-α (50 ng/ml) or LT-α (50 ng/ml) had no significant effects on TRANCE expression.

Figure 23:
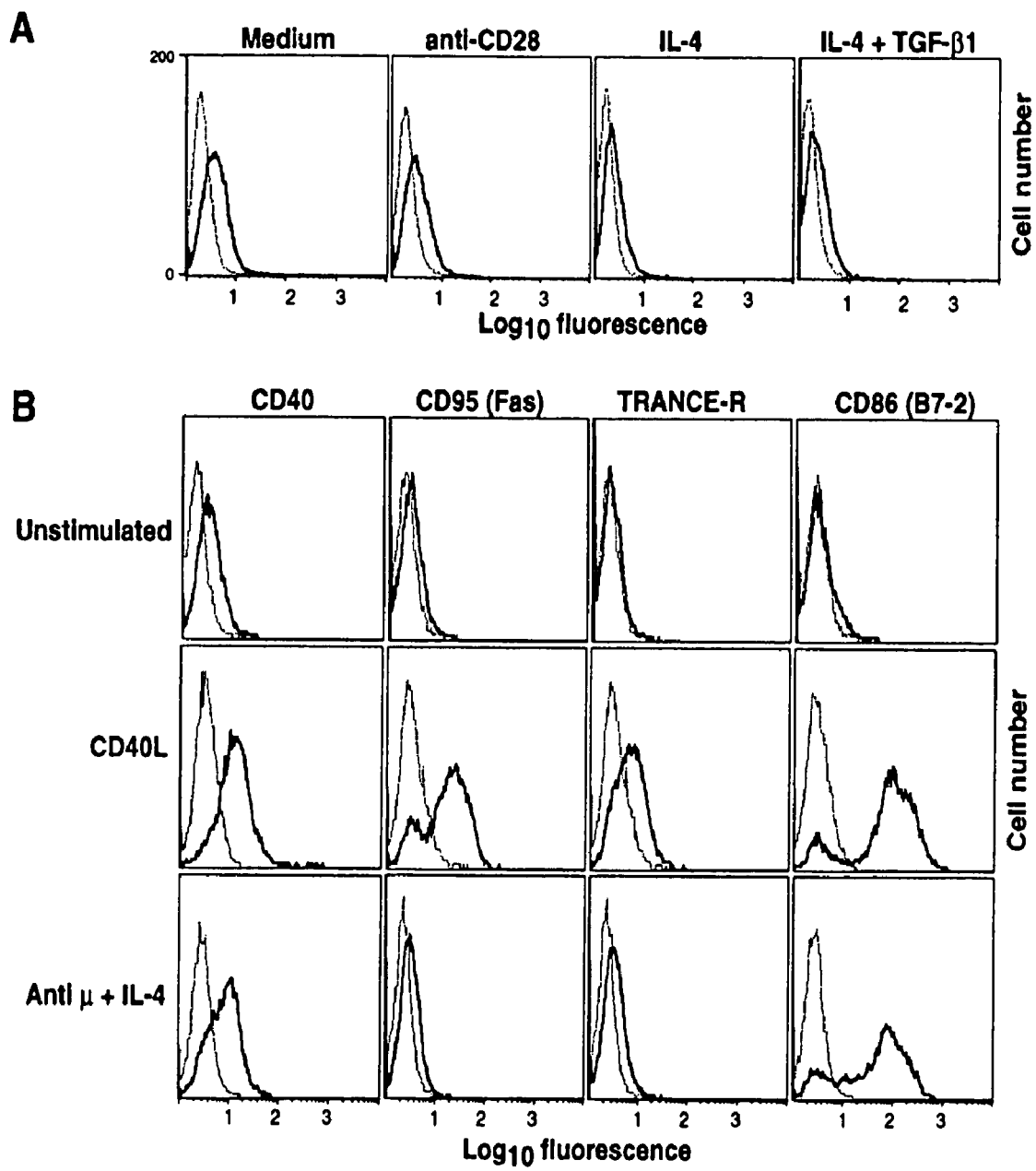

TRANCE-receptor is expressed on activated T and B cells. It has been set forth that levels of TRANCE-R are expressed on mature DC (73). Since TRANCE-R has also been detected on activated human T cells (72) and TRANCE can activate c-Jun N-terminal kinase in thymocytes (73), expression of TRANCE-R was analyzed on murine T cells using the hCD8-mTRANCE fusion molecule (FIG. 18B) and FACS analysis (FIG. 23). As explained in Examples set forth above, resting T-cells did not show any detectable TRANCE-R expression on their-surfaces (FIG. 23A). However, when T cells were stimulated with anti-CD3, low levels of TRANCE-R were detected only after 48 h of simulation and were not further increased by anti-CD28-mediated costimulation. TRANCE-R expression was not enhanced by IL-4 and/or TGF-b1, either (FIG. 23A) despite a previous study showing that these cytokines enhance the expression of TRANCE-R on activated human T cells (72). In addition, Applicants have discovered that TRANCE did not have any effect on the survival or primary or secondary proliferative responses of murine CD4+ or CD8⁺ T cells despite significant TRANCE-R expression on those cells. TRANCE-R expression can be also detected on activated B cells (FIG. 23B). TRANCE-R expression was detected after 24 h of stimulation and peaked at 48 h. Moreover, TRANCE-R expression was significantly enhanced by CD40 cross linking on B cells but only slightly by anti-μ+IL-4. This stimulatory requirements of TRANCE-R expression on B cells was similar to that of Fas expression (FIG. 23B). The level of expression of TRANCE-R on mature DCs was consistently at least 10-fold higher than on activated B cells. TRANCE had no effect on proliferation, the expression of surface activation/adhesion markers or survival of B cells stimulated to express TRANCE-R.

Figure 24:
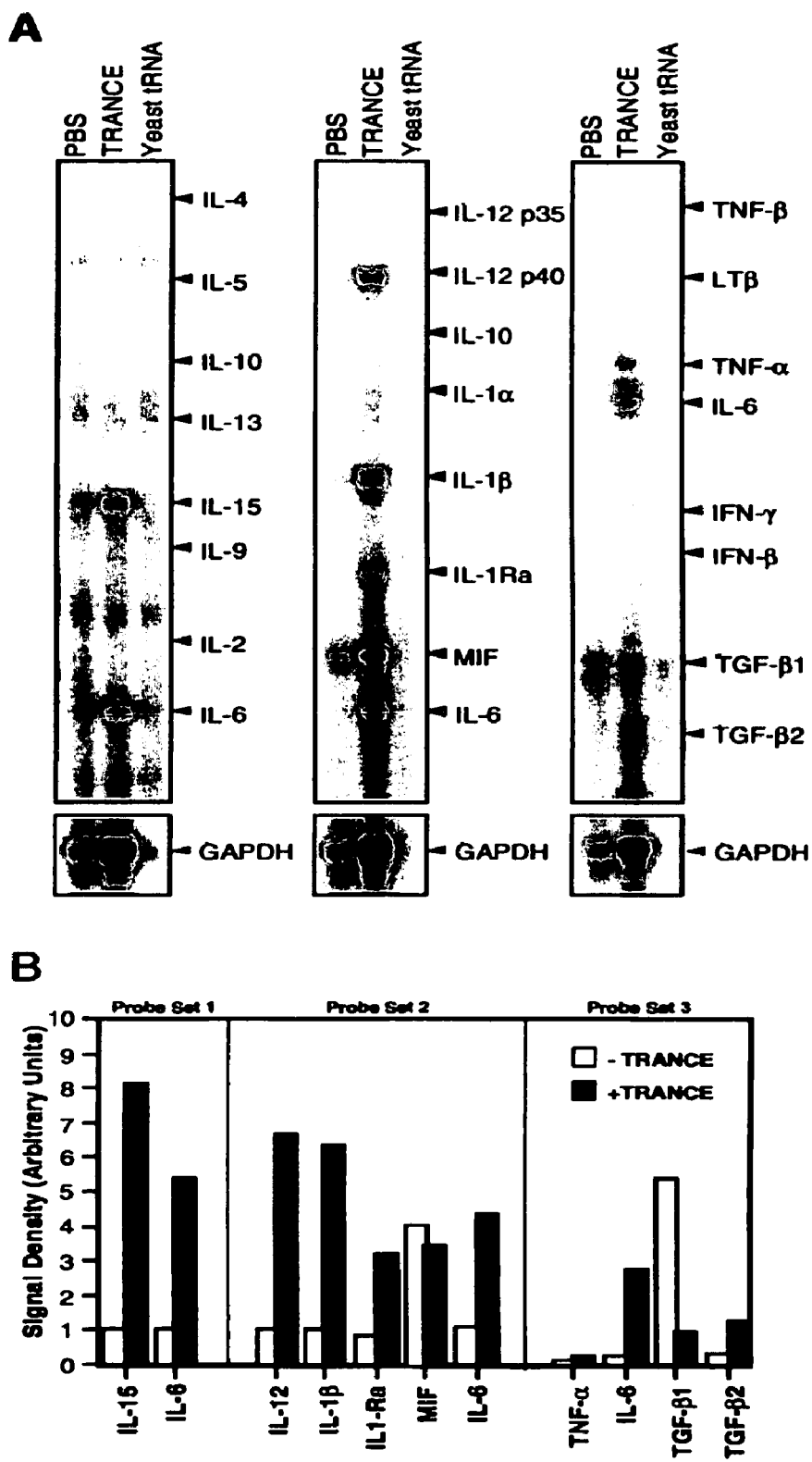

TRANCE induces cytokine production in DC. TRANCE and CD40L can upregulate Bcl-$x_L$ expression and protect DC against spontaneous apoptosis in vitro (73). In addition to its survival-enhancing function in DC, CD40L can induce IL-12 and IL-18 expression (80) which in turn can promote a Th1-mediated immune response, and an array of cytokines involved in T-cell activation (IL-1, IL-6, IL-15, TNF-α) (80-81). To determine if TRANCE plays a similar role in cytokine regulation, TRANCE-treated or PBS-treated DC were subjected to ribonuclease protection assays (RPA) with probes specific for a variety of known cytokines (FIG. 24). Applicants have discovered that TRANCE induces the expression of the proinflammatory cytokines IL-1β, IL-1Ra, IL-6, the T-cell and NK cell activating cytokine, IL-15 (FIG. 24). TRANCE also upregulates the mRNA encoding the p40 subunit of IL-12. In this assay, IL-12 p35 mRNA was not detected. Although under no duty to explain such lack of detection, and certainly not intending to be bound by any hypothesis presented here, it is hypothesized that the lack of detection of IL-12 p35 mRNA was probably because the steady state level of p35 mRNA was below the limit of detection. TRANCE had no apparent effect on the expression of IL-2, IL-4, IL-5, IL-9, IL-10, IL-1α, TNF-α, TNF-β (LT-α), LT-β, IFN-γ or IFN-β (FIG. 24). By the same method, it was shown that CD40L also upregulated the expression of IL-1β, IL-1Ra, IL-6, IL-12 p40 (but not p35), IL-15. However, TRANCE and CD40L differed in the regulation of TGF-β2 expression; TRANCE induced TGF-β2 expression and down-regulated TGF-β1 (FIG. 24) whereas CD40L upregulated both TGF-β1 and TGF-β2.

Figure 16:
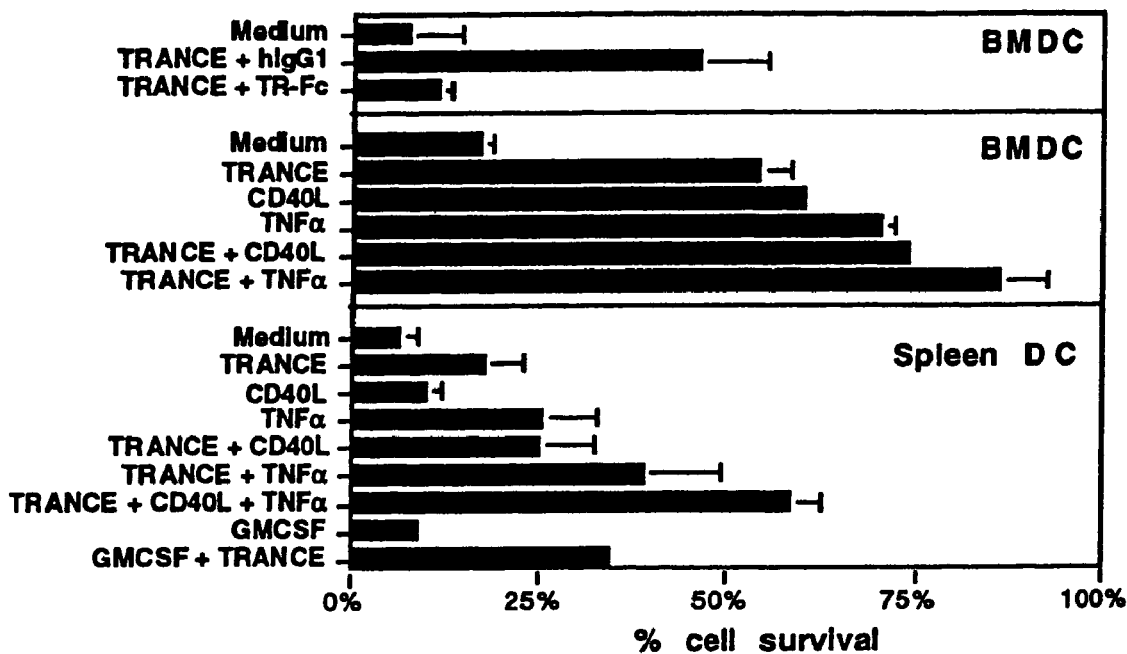
FIG. 16. In vitro survival of mature DC. Mature bone-marrow or splenic DC were incubated in media with combinations of GM-CSF (10 ng/ml), mCD8-CD40L (1:100 dilution), hCD8-TRANCE (1 mg/mL), hIgG1 (10 mg/ml), TR-Fc (10 mg/ml), and mTNFα (50 ng/mL) for 72 h (bone marrow derived DC) or 24 h (spleen DC) and cell viability was measured by trypan blue exclusion. These concentrations of mCD8-CD40L, hCD8-TRANCE and mTNFα were found to be saturating for survival of BMDC. Representative results of 3 independent experiments are shown.

TRANCE cooperates with a protein of the TNF family to enhance the survival of DC. Applicants have discovered that, surprisingly and unexpectedly, during a T-cell-DC interaction both TRANCE and a protein of the TNF family, such as CD40L or TNF-α cooperatively enhance DC survival. As shown in FIG. 16, the addition of both ligands together, inhibited cell death to a greater degree than either ligand alone (FIG. 16). TNF could also prevent spontaneous apoptosis as previously described (82) and also cooperates with TRANCE to enhance splenic DC survival (FIG. 16). GM-CSF, a cytokine required for DC differentiation, had little effect on splenic DC survival, however, its effect was significantly amplified when administered with TRANCE (FIG. 16). The cooperative effect of TRANCE, CD40L and TNFα on DC survival was also observed with BMDC (FIG. 16).

Discussion

The data presented here further uncovers the role of TRANCE/TRANCE-R in the immune system. Previously, TRANCE was shown to enhance the survival of DCs, a property shared with CD40L (21, 73). However, heretofore, the cooperative nature of such proteins in increasing survival of dendritic cells was not known. It has been set forth above that TRANCE is expressed on both activated CD4+ and CD8+ T-cells, with higher levels of expression observed on CD4+ T cells, while CD40L is expressed only in activated CD4− cells. Hence, TRANCE allows CD4+ T-cells to modulate DC function independently of CD40L. TCR stimulation by itself is sufficient to induce TRANCE expression on T cells, which can be further increased by CD28-mediated costimulation on CD4+ T cells but not significantly on CD8+ T cells. In contrast, CD28 costimulation does not modify the level but only the kinetics of expression of CD40L on activated CD4+ T cell (83, 84). Moreover, the kinetics of TRANCE expression during CD4+ T cell activation are different from those described for CD40L (85). Indeed, maximal levels of TRANCE expression are detected at 48 h after stimulation and persist for at least 2 days more whereas CD40L protein has been shown to be rapidly expressed and then to wane within 16-24 h (85). Therefore, TRANCE acts at later time point than CD40L during CD4+ T-cell mediated immune response to regulate the functions of DCs. Interestingly, CD40 is expressed on both immature and mature DC and can signal DC maturation (67), whereas TRANCE-R is only expressed on mature DC (73).

Furthermore, it has been shown that TRANCE-R is not detected on resting T-cells by FACS analysis (73). In addition, just as with human activated T-cells, TRANCE-R can be detected on murine. T-cells when activated. However, TRANCE does not effect proliferation, costimulation, survival or cell death in these cells, contrary to what has been observed in human T cells (72). Although under no duty to explain such a discrepency, and certainly not intending to be bound by any hypothesis for the cause of these discrepencies, these discrepancies could reflect functional differences between the human and mouse TRANCE-R in T-cells and/or to differences in culture and stimulation conditions. Moreover, contrary to previous reports which disclose that a soluble form of TRANCE can be shed from TRANCE-transfected 293 cells, TRANCE was not shed in vitro from activated T cell hybridoma. Hence, the relative low level of TRANCE-R on activated T-cells is not due to the production of soluble TRANCE by those cells.

In addition, set forth herein is a discovery that activated B cells also express low levels of TRANCE-R. Similar to activated T-cells, the proliferation, the survival and the phenotype of activated B cells were not affected by TRANCE. Hence, data set forth herein indicates that the major immune target cells for TRANCE are DCs, which is a significant and important difference with CD40L. This is an important difference with CD40L, which has also a major effect on B cell function.

In addition to its ability to enhance DC survival, TRANCE also promotes the production of various cytokines (e.g., IL-12, IL-15, IL-1 and IL-6) in DCs. CD40L is known to be a major stimulus inducing IL-12 production by DC (25, 69), a critical cytokine involved in Th1 differentiation (71). However, neutralizing antibodies to CD40L fail to completely block IL-12 production in an MLR with T-cells and DC (69) and CD40L knockout mice are still able to produce IL-12 (87). TRANCE also induces IL-12 production in DC. Consequently, as set forth herein, TRANCE complements CD40L in vivo to promote DC-mediated Th1 differentiation. Interestingly, IL-4, which is required for Th-2 cell differentiation (88) substantially inhibits TRANCE expression on activated CD4+ T cells. Thus IL-4 producing cells down regulate TRANCE expression on T cells during T cell priming leading to a decreased IL-12 production by DC and therefore decreased Th1 differentiation. Consistent with the potential role of TRANCE in enhancing Th1 responses and the effect of IL-4 on TRANCE expression are the lower levels of TRANCE on activated Th2 clones as compared to the Th1 clones from DO11.10 mice.

IL-15 is a cytokine that shares functional similarities and receptor chain usage with IL-2 (89). It is a mitogen for NK cells (89) and is a T-cell growth factor (91) and chemoattractant (91). Similar to human CD34+derived DC, resting murine DC expressed very low levels of IL-15 mRNA (80), which were dramatically upregulated upon TRANCE-R or CD40 triggering. In addition, IL-15 can enhance the survival of activated T-cells (92) and specifically activates memory CD8+ T cells (93). Hence, activated/memory Th cells which express high levels of TRANCE promote their own survival by interacting with DC and inducing IL-15 production. Furthermore, just as with CD40L (80), TRANCE unexpectedly can also trigger the production of proinflammatory cytokines such as IL-1 and IL-6 which can amplify the immune response initiated by DC. TRANCE and CD40L therefore behave similarly in their ability to enhance DC-mediated lymphocyte activation.

Furthermore, it is clearly set forth herein that TRANCE and a protein of the TNF family, cooperate to enhance the survival of Dcs, and thus can be used to modulate immune response in an animal, or to treat an immune system related disease or disorder in an animal. In particular, TRANCE and CD40L, both of which are expressed on CD4+ T cells, cooperate to enhance the survival of DCs. Hence, DC survival in vivo utilizes the combined action of several TNF-family members, including TNF-α, which are likely to be provided by activated CD4+ and CD8+ T-cells and those present in the local microenvironment.

REFERENCES

1. Smith, C. A., Farrah, T. and Goodwin, R. G. (1994) *Cell* 76, 959-962
2. Wiley, S. R., Schooley, K., Smolak, P. J., Din, W. S., Huand, C.-P. Nicholl, J. K., Sutherland, G. R., Smith, T. D., Rauch, C., Smith, C. A. and Goodwin, R. G. (1995) *Immunity* 3, 673-682
3. Pitti, R. M., Marsters, S. A., Ruppert, S., Donahue, D. J., Moore, A. and Ashkenazi, A. (1996) *J. Biol. Chem* 271, 12687-12690
4. Darnay, B. G. and Aggarwal, B. B. (1997) *J. Leuk. Biol.* 61, 559-566
5. Van Lint, J., Agostinis, P., Vandevoorde, V., Haegeman, G., Fiers, W., Merlevede, W. and Vandenheede, J. R. (1992) *J. Biol. Chem.* 267, 25916-25921
6. Sutherland, C. L., Heath, A. W., Pelech, S. L., Young, P. R. and Gold, M. R. (1996) *J. Immunol.* 157, 3381-3390
7. Barin, M. (1996) *Science* 274, 724
8. Baldwin, A. S. J. (1996) *Annu. Rev. Immunol.* 14, 649-683
9. Natoli, G., Costanzo, A., Ianni, A., Templeton, D. J., Woodgett, J. R., Balsano, C. and Levrero, M. (1997) *Science* 275, 200-203
10. Yang, X., Khosravi-Far, R., Chang, H. Y. and Baltimore, D. (1997) *Cell* 89, 1067-1076
11. Rao, A. (1995) *J. Leukoc. Biol.* 57, 536-542
12. Verheij, M., Bose, R., Lin, X. H., Yao, B., Jarvis, W. D., Grant, S., Birrer, M. J., Szabo, E., Zon, L. I., Kyriakis, J. M., Haimovitz-Friedman, A., Fuks, Z. and Kolesnick, R. N. (380) *Nature* 380, 75-79
13. Xia, Z., Dickens, M., Raingeaud, J., Davis, R. J. and Greenberg, M. E. (1995) *Science* 270, 1326-1331
14. Goillot, E., Raingeaud, J., Ranger, A., Tepper, R. I., Davis, R. J., Harlow, E. and Sanchez, I. (1997) *Proc. Natl. Acad. Sci.* 94, 3302-3307
15. Liu, Z. G., Hsu, H., Goeddel, D. V. and Karin, M. (1996) *Cell* 87, 565-576
16. Amakawa, R., Hakem, A., Kundig, T. M., Matsuyama, T., Simard, J. J., Timms, E., akeham, A., Mittruecker, H.-W., Griesser, H., Takimoto, H., Schmits, R., Shahinian, A., Ohashi, P. S., Penninger, J. M. and Mak, T. W. (1996) *Cell* 84, 551-562
17. Zheng, L., Fisher, G., Miller, R. E., Peschon, J., Lynch, D. H. and Lenardo, M. J. (1995) *Nature* 377, 348-351
18. Kehrl, J. H., Alvarez-Mon, M., Delsing, G. A. and Fauci, A. S. (1987) *Science* 238, 1144
19. Clark, E. A. and Ledbetter, J. A. (1994) *Nature* 367, 425
20. Smith, C. A., Davis, T., Anderson, D., Solam, L., Beckmann, M. P., Jerzy, R., Dower, S. K., Cosman, D. and Goodwin, R. G. (1990) *Science* 248, 1019-1023
21. Caux, C., Massacrier, C., Vanbervliet, B., Dubois, B., Van Kooten, C., Durand, I. and Banchereau, J. (1994) *J. Exp. Med* 180, 1263-1271
22. Berke, G. (1995) *Cell* 81, 9-12
23. Wong, B., Park, C. G. and Choi, Y. C. (1997) *Semin. Immunol.* 9, 7-16
24. Park, C. G., Lee, S. Y., Kandala, G., Lee, S. Y. and Choi, Y. (1996) *Immunity* 4, 583-591
25. Cella, M., Scheidegger, D., Palmer-Lehmann, K., Lane, P., Lanzavecchia, A. and Alber, G. (1996) *J. Exp. Med* 184, 747-752
26. Walter, M., Spillet, D., Thomas, P., Weissenbach, J. and Goodfellow, P. (1994) *Nat. Genet.* 7, 22-28
27. de Lecea, L., Ruiz-Lozano, P., Danielson, P. E., Peelle-Kirley, J., Foye, P. E., Frankel, W. N. and Sutcliffe, J. G. (1997) *Genomics* 42, 499-506
28. Johnson, K. R., Cook, S. A. and Davisson, M. T. (1995) *Mamm. Genome* 5, 670-687
29. Reinhard, C., Shamoon, B., Shyamala, V. and Williams, L. T. (1997) *EMBO* 16, 1080-1092
30. Diatchenko, L., Lau, Y. F., Campbell, A. P., Chenchik, A., Moqadam, F., Huang, B., Lukyanov, S., Lukyanov, K., Gurskaya, N., Sverdlov, E. D. and Siebert, P. D. (1996) *Proc. Natl. Acad. Sci. USA* 93, 6025-6030
31. Eck, M. J. and Sprang, S. R. (1989) *J. Biol. Chem.* 264, 17595-17605
32. Goldfeld, A. E., McCaffrey, P. G., Strominger, J. L. and Rao, A. (1993) *J. Exp. Med* 178, 1365-1379
33. Hodge, M. R., Ranger, A. M., de la Brousse, F. C., Hoey, T., Grusby, M. J. and Glimcher, L. H. (1996) *Immunity* 4, 397-405
34. Rozzo, S. J., Vyse, T. J., Drake, C. G. and Kotzin, B. L. (1996) *Proc. Natl. Acad. Sci.* 93, 15164-15168
35. Wyllie, A. H. 1992. Apoptosis and the regulation of cell numbers in normal and neoplastic tissues: an overview. *Cancer Metastasis Rev.* 11:95-103.
36. Russell, J. H. 1995. Activation-induced death of mature T cells in the regulation of immune responses. *Curr. Opin. Immunol.* 7:382-388.
37. Lynch, D. H., F. Ramsdell, and M. R. Alderson. 1995. Fas and FasL in the homeostatic regulation of immune responses. *Immunol. Today* 16:569-574.
38. Smith, C. A., T. Farrah, and R. G. Goodwin. 1994. The TNF receptor superfamily of cellular and viral proteins: activation, costimulation, and death. *Cell* 76:959-962.
39. Rothe, M., S. C. Wong, W. J. Henzel, and D. V. Goeddel. 1994. A novel family of putative signal transducers associated with the cytoplasmic domain of the 75 kDa tumor necrosis factor receptor. *Cell* 78:681-692.
40. Rothe, M., V. Sarma, V. M. Dixit, and D. V. Goeddel. 1995. TRAF2-mediated activation of NF-κB by TNF receptor 2 and CD40. *Science* 269:1424-1427.
41. Natoli, G., A. Costanzo, A. Ianni, D. J. Templeton, J. R. Woodgett, C. Balsano, and M. Levrero. 1997. Activation of SAPK/JNK by TNF receptor 1 through a noncytotoxic TRAF2-dependent pathway. *Science* 275:200-203.
42. Reinhard, C., B. Shamoon, V. Shyamala, and L. T. Williams. 1997. Tumor necrosis factor alpha-induced activation of c-jun N-terminal kinase is mediated by TRAF2. *EMBO J.* 16:1080-1092.
43. Liu, Z. G., H. Hsu, D. V. Goeddel, and M. Karin. 1996. Dissection of TNF receptor 1 effector functions: JNK activation is not linked to apoptosis while NF-κB activation prevents cell death. *Cell* 87:565-576.

44. Darnay, B. G., and B. B. Aggarwal. 1997. Early events in TNF signaling: a story of associations and dissociations. *J. Leuk. Biol.* 61:559-566.
45. Barin, M. 1996. Life-death balance within the cell. *Science* 274:724.
46. Bjorck, P., J. Banchereau, and R. L. Flores. 1997. CD40 ligation counteracts Fas-induced apoptosis of human dendritic cells. *Int. Immunol.* 9:365-372.
47. Wang, Z., J. G. Karras, R. G. Howard, and T. L. Rothstein. 1995. Induction of bcl-x by CD40 engagement rescues slg-induced apoptosis in murine B cells. *J. Immunol.* 155:3722-3725.
48. Minn, A. J., P. Velez, S. L. Schendel, H. Liang, S. W. Muchmore, S. W. Fesik, M. Fill, and C. B. Thompson. 1997. Bcl-$x_L$ forms an ion channel in synthetic lipid membranes. *Nature* 385:353-357.
49. Chinnaiyan, A. M., K. O'Rourke, B. R. Lane, and V. M. Dixit. 1997. Interaction of CED-4 with CED-3 and CED-9: a molecular framework for cell death. *Science* 275:1122-5126.
50. Chinnaiyan, A. M., K. Orth, K. O'Rourke, H. Duan, G. G. Poirier, and V. M. Dixit. 1996. Molecular ordering of the cell death pathway. Bcl-2 and Bcl-$x_L$ function upstream of the CED-3-like apoptotic proteases. *J. Biol. Chem.* 271:4573-4576.
51. Steinman, R. M. 1991. The dendritic cell system and its role in immunogenicity. *Annu. Rev. Immunol.* 9:271-296.
52. Flores, R. L., P. Bjorck, V. Duvert, K. C. van, S. Saeland, and J. Banchereau. 1997. CD40 ligation on human cord blood CD34$^+$ hematopoietic progenitors induces their proliferation and differentiation into functional dendritic cells. *J. Exp. Med.* 185:341-349.
53. Caux, C., B. Vanbervliet, C. Massacrier, C. Dezutter Dambuyant, B. de Saint Vis, C. Jacquet, K. Yoneda, S. Imamura, D. Schmitt, and J. Banchereau. 1996. CD34$^-$ hematopoietic progenitors from human cord blood differentiate along two independent dendritic cell pathways in response to GM-CSF+TNF alpha. *J. Exp. Med.* 184:695-706.
54. Young, J. W., P. Szabolcs, and M. A. Moore. 1995. Identification of dendritic cell colony-forming units among normal human CD34$^+$ bone marrow progenitors that are expanded by c-kit-ligand and yield pure dendritic cell colonies in the presence of granulocyte/macrophage colony-stimulating factor and tumor necrosis factor alpha. *J. Exp. Med.* 182:1111-1119.
55. van, K. C., and J. Banchereau. 1997. Functions of CD40 on B cells, dendritic cells and other cells. *Curr. Opin. Immunol.* 3:330-337.
56. Wong, B., J. Rho, J. Arron, E. Robinson, J. Orlinick, M. Chao, S. Kalachikov, E. Cayani, F. S. Bartlett, III, W. Frankel, S. Lee, and Y. Choi. 1997. TRANCE is a novel ligand of the tumor necrosis factor receptor family that activates c-Jun N-terminal kinase in T cells. *J. Biol. Chem.* 372:25190-25194.
57. Lee, S., A. Reichlin, A. Santana, K. Sokol, M. Nussenzweig, and Y. Choi. 1997. TRAF2 is essential for JNK but not NF-κB activation and regulates lymphocyte proliferation and survival. *Immunity, in press*.
58. Inaba, K., M. Inaba, N. Romani, H. Aya, M. Deguchi, S. Ikehara, S. Muramatsu, and R. M. Steinman. 1992. Generation of large numbers of dendritic cells from mouse bone marrow cultures supplemented with granulocyte/macrophage colony-stimulating factor. *J. Exp. Med.* 176:1693-1702.
59. Steinman, R. M., G. Kaplan, M. D. Witmer, and Z. A. Cohn. 1979. Identification of a novel cell type in peripheral lymphoid organs of mice. V. Purification of spleen dendritic cells, new surface markers, and maintenance in vitro. *J. Exp. Med.* 149:1-16.
60. Bender, A., M. Sapp, G. Schuler, R. M. Steinman, and N. Bhardwaj. 1996. Improved methods for the generation of dendritic cells from nonproliferating progenitors in human blood. *J. Immunol. Methods.* 196:121-135.
61. Josien, R., M. Heslan, J. P. Soulillou, and M. C. Cuturi. 1997. Rat spleen dendritic cells express natural killer cell receptor protein 1 (NKR-P1) and have cytotoxic activity to select targets via a Ca$^{2+}$-dependent mechanism. *J. Exp. Med* 186:467-472.
62. Caux, C., C. Massacrier, B. Vanbervliet, B. Dubois, C. Kootan, I. Durand, and J. Banchereau. 1994. Activation of human dendritic cells through CD40 cross-linking. *J. Exp. Med* 180:1263-1272.
63. Ludewig, B., D. Graf, H. Gelderblom, Y. Becker, R. Kroczek, and G. Pauli. 1995. Spontaneous apoptosis of dendritic cells is inhibited by TRAP (CD40-ligand) and TNF-alpha, but strongly enhanced by interleukin-10. *Eur. J. Immunol.* 25:1943-1950.
64. Granelli, P. A., M. Pope, K. Inaba, and R. M. Steinman. 1995. Coexpression of NF-κB/Rel and Sp1 transcription factors in human immunodeficiency virus 1-induced, dendritic cell-T-cell syncytia. *Proc. Natl. Acad. Sci. USA* 92:10944-10948.
65. Steinman, R. M., M. Pack, and K. Inaba. 1997. Dendritic cells in the T-cell areas of lymphoid organs. *Immunol. Rev.* 156:25-37.
66. Young, J. W., and K. Inaba. 1996. Dendritic cells as adjuvants for class I major histocompatibility complex-restricted antitumor immunity. *J. Exp. Med* 183:7-11.
67. Banchereau, J. and R. M. Steinman. 1998. *Nature* 392:245.
68. Flores-Romo, L., P. Bjorck et al. 1997. *J. Exp. Med.* 185:341.
69. Koch, F., U. Stanzl et al. 1996. *J. Exp. Med* 184:741.
70. Heufler, C., F. Koch et al. 1996. *Eur. J. Immunol.* 26:659.
71. Macatonia, s. E., N. A. Hosken et al. 1995. *J. Immunol.* 154:5071.
72. Anderson, D. M., E. Maraskovsky et al. 1997. *Nature* 390:175.
73. Wong, B. R., R. Josien et al 1997. *J. Exp. Med* 186:2075.
74. Yasuda, H., N. Shima et al. 1998. *Proc. Natl. Acad. Sci. USA* 95:3597.
75. Lacey, D. L., E. Timms et al. 1998. *Cell* 93:165.
76. Simonet, W. S., D. L. Lacey, et al 1997. *Cell* 89:309.
77. Foy, T. M., A Aruffo et al 1996. *Annu. Rev. Immunol.* 14:591.
78. Foy, T. M., D. M. Page et al 1995. *J. Exp. Med* 182:1377.
79. Kang, K., M. Kubin et al. 1996. *J. Immunol.* 156:1402.
80. de Saint-Vis, B., I. Fugier-Vivier, et al. 1998. *J. Immunol.* 160:1666.
81. Jonuleit, H. K. Wiedemann et al. 1997. *J. Immunol.* 158:2610.
82. Ludewig, B., V. Henn et al. 1996. *Eur. J. Immunol.* 26:3137.
83. Klaus, S. J., L. M. Pinchuk et al. 1994. *J. Immunol.* 152:5643.
84. Johnson-Leger, C., J. Christensen et al. 1998. *Int. Immunol.* 10:1083.
85. Roy. M., T. Walschmidt et al. 1993. *J. Immunol.* 151:2497.
86. Banchereau, J., F. Bazan, et al. 1994. *Annu. Rev. Immunol.* 12:881.
87. Campos-Neto, A., P. Ovendale et al. 1998. *J. Immunol.* 160:2037.
88. Paul, W., and R. Seder. 1994. *Cell* 76:241.

89. Grabstein, K. H., J. Eisenman, et al. 1994. *Science* 264: 965.
90. Laclercq, G., v. Debacker et al. 1996. *J. Exp. Med* 184: 325.
91. Wilkinson, P. C., and F. Y. Liew. 1995. *J. Exp. Med* 181:1255.
92. Vella, A., S. Dow et al. 1998. *Proc. Natl. Acad. Sci. USA* 95:3810.
93. Zhang, X., S. Sun et al. 1998. *Immunity* 8:591.
94. Grewal, I. S. and R. A. Flavell. 1998. *Annu. Rev. Immunol.* 16:111.

Many other variations and modifications of the invention will be apparent to those skilled in the art without departing from the spirit and scope of the invention. The above embodiments are, therefore, merely exemplary, and all such variations and modifications are intended to be within the scope of the invention as defined in the appended claims.

It is further understood that all base sizes or amino acid sizes, and all molecular weight or molecular weight mass values given for nucleic acids or polypeptides are approximate, and are provided for description.

Various publications are cited herein, the disclosures of which are incorporated by reference in their entireties.

What is claimed is:

1. A method for increasing the viability of a dendritic cell, comprising contacting the dendritic cell with an isolated Tumor Necrosis Factor (TNF)-Related Activation Induced Cytokine (TRANCE) comprising the amino acid sequence of SEQ ID NO:2, wherein said dendritic cell contacted by said isolated TRANCE has an increased viability relative to a control dendritic cell not contacted with said isolated TRANCE.

2. The method of claim 1, wherein the contacting of the dendritic cell with said isolated TRANCE occurs in vitro or in vivo.

3. A method of increasing viability of a dendritic cell, comprising contacting the dendritic cells with an isolated Tumor Necrosis Factor (TNF)-Related Activation Induced Cytokine (TRANCE) comprising the amino acid sequence of SEQ ID NO:2, and contacting the dendritic cell with an isolated protein which is a member of the Tumor Necrosis Factor (TNF) superfamily of proteins, such that the dendritic cell comprises an increased viability relative to a control dendritic cell not pulsed with TRANCE and the protein.

4. The method of claim 3, wherein the contacting steps occur simultaneously.

5. The method of claim 3, wherein the isolated protein which is a member of the TNF superfamily comprises CD40L or TNF-α.

6. A method for increasing viability of a dendritic cell of an animal in vivo, comprising: removing an immature dendritic cell from the animal; pulsing the immature dendritic cell with an isolated Tumor Necrosis Factor (TNF)-Related Activation Induced Cytokine (TRANCE) comprising the amino acid sequence of SEQ ID NO:2; inducing the immature dendritic cell to mature; and reintroducing the mature dendritic cell into the animal.

7. The method of claim 6, further comprising the step of washing the dendritic cell before reintroducing the dendritic cell into the animal.

8. A method for increasing immune response in an animal towards an antigen, comprising the steps of: removing an immature dendritic cell from the animal; pulsing the immature dendritic cell with an isolated Tumor Necrosis Factor (TNF)-Related Activation Induced Cytokine (TRANCE) comprising the amino acid sequence of SEQ ID NO:2; pulsing the immature dendritic cell with the antigen; inducing the immature dendritic cell to mature; and reintroducing the mature dendritic cell into the animal.

9. The method of claim 8, further comprising the step of washing the dendritic cell before reintroducing the dendritic cell into the animal.

10. The method of claim 8, wherein the antigen comprises: b) a pathogen, or a fragment thereof; c) a virus, or a fragment thereof and d) a tumor, or a fragment thereof.

11. A method for increasing immune response in an animal towards an antigen, comprising the steps of: removing an immature dendritic cell from the animal; pulsing the immature dendritic cell with an isolated Tumor Necrosis Factor (TNF)-Related Activation Induced Cytokine (TRANCE) comprising the amino acid sequence of SEQ ID NO:2; pulsing the immature dendritic cell with an isolated protein of the TNF superfamily; pulsing the immature dendritic cell with the antigen; inducing the immature dendritic cell to mature; and reintroducing the dendritic cell into the animal.

12. The method of claim 11, further comprising the step of washing the dendritic cell before reintroducing the dendritic cell into the animal.

13. The method of claim 11, wherein the antigen comprises: a) a pathogen, or a fragment thereof b) a virus, or a fragment thereof and c) a tumor, or a fragment thereof.

14. The method of claim 11, wherein the isolated protein of the TNF superfamily comprises CD40L or TNF-$\alpha$.

15. The method of claim 11, wherein the steps of pulsing the dendritic cell are performed simultaneously.

\* \* \* \* \*